(12) United States Patent
Birikh et al.

(10) Patent No.: US 10,815,472 B2
(45) Date of Patent: Oct. 27, 2020

(54) METHOD FOR OBTAINING ACTIVE INSOLUBLE XYLOSE ISOMERASE

(71) Applicant: METGEN OY, Kaarina (FI)

(72) Inventors: Klara Birikh, Kaarina (FI); Anu Minna Maaret Suonpää, Kaarina (FI)

(73) Assignee: METGEN OY, Kaarina (FI)

(*) Notice: Subject to any disclaimer, the term of this patent is extended or adjusted under 35 U.S.C. 154(b) by 43 days.

(21) Appl. No.: 16/311,611

(22) PCT Filed: Jun. 20, 2017

(86) PCT No.: PCT/EP2017/065045
§ 371 (c)(1),
(2) Date: Dec. 19, 2018

(87) PCT Pub. No.: WO2017/220551
PCT Pub. Date: Dec. 28, 2017

(65) Prior Publication Data
US 2019/0185842 A1  Jun. 20, 2019

(30) Foreign Application Priority Data
Jun. 20, 2016 (EP) .................................. 16175238

(51) Int. Cl.
*C12N 9/90* (2006.01)
*C12N 15/00* (2006.01)
(Continued)

(52) U.S. Cl.
CPC ............... *C12N 9/92* (2013.01); *C12N 9/88* (2013.01); *C12N 9/90* (2013.01); *C12N 9/96* (2013.01);
(Continued)

(58) Field of Classification Search
CPC ......... C12N 9/92; C12N 9/90; C07K 2319/00
(Continued)

(56) References Cited

U.S. PATENT DOCUMENTS

| | | | | |
|---|---|---|---|---|
| 5,656,497 A | * | 8/1997 | Zeikus | ................. C12N 9/92 435/234 |
| 7,244,819 B2 | * | 7/2007 | Scholz | ................. A61P 43/00 530/350 |
| 2019/0185892 A1 | * | 6/2019 | Birikh | ................. C12P 19/24 |

FOREIGN PATENT DOCUMENTS

| | | |
|---|---|---|
| EP | 1780282 A1 | 5/2007 |
| WO | 03000878 A2 | 1/2003 |
| WO | 03062387 A2 | 7/2003 |

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Patent Law Works, LLP

(57) ABSTRACT

The invention is in the field of biotechnology and involves recombinant DNA technology. It provides means and methods for obtaining an insoluble active fusion protein comprising xylose isomerase activity. More in particular, the invention relates to a method for obtaining active insoluble xylose isomerase, comprising the expression in a host organism of a recombinant gene encoding a fusion protein comprising a xylose isomerase in combination with a PPIase, thereby obtaining the active insoluble xylose isomerase. It also provides recombinant fusion proteins comprising xylose isomerase activity as well as their use in converting xylose to xylulose and glucose to fructose.

11 Claims, 4 Drawing Sheets

Figure 1:
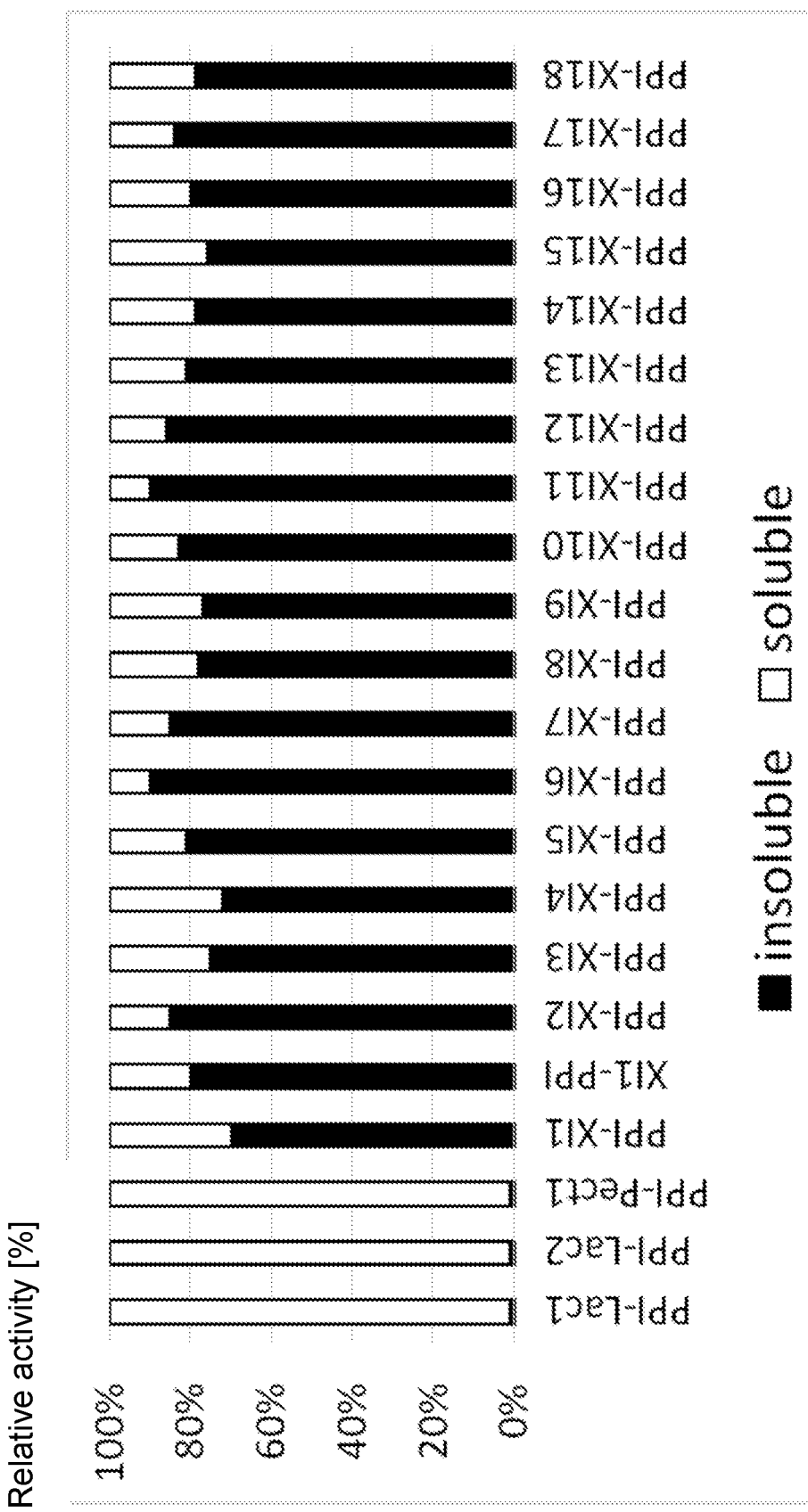

Specification includes a Sequence Listing.

(51) Int. Cl.
  *C12P 19/02* (2006.01)
  *C07H 21/04* (2006.01)
  *C12N 9/92* (2006.01)
  *C12P 19/24* (2006.01)
  *C12N 9/88* (2006.01)
  *C12N 9/96* (2006.01)

(52) U.S. Cl.
  CPC ....... *C12P 19/24* (2013.01); *C12Y 402/02002* (2013.01); *C12Y 502/01008* (2013.01); *C12Y 503/01005* (2013.01); *C07K 2319/00* (2013.01)

(58) Field of Classification Search
  USPC .................................. 435/233, 440; 536/23.4
  See application file for complete search history.

(56) References Cited

OTHER PUBLICATIONS

PPIB_ECOLI (UnitProtKB Database. May 27, 2015.*
PCT International Search Report and Written Opinion, Application No. PCT/EP2017/065045, dated Sep. 18, 2017, 11 pages.

* cited by examiner

SEQUENCE LISTING

<160> NUMBER OF SEQ ID NOS: 44

<210> SEQ ID NO 1
<211> LENGTH: 444
<212> TYPE: PRT
<213> ORGANISM: THERMOTOGA NEAPOLITANA

<400> SEQUENCE: 1

```
Met Ala Glu Phe Phe Pro Glu Ile Pro Lys Val Gln Phe Glu Gly Lys
1               5                   10                  15

Glu Ser Thr Asn Pro Leu Ala Phe Lys Phe Tyr Asp Pro Glu Glu Ile
            20                  25                  30

Ile Asp Gly Lys Pro Leu Lys Asp His Leu Lys Phe Ser Val Ala Phe
        35                  40                  45

Trp His Thr Phe Val Asn Glu Gly Arg Asp Pro Phe Gly Asp Pro Thr
    50                  55                  60

Ala Asp Arg Pro Trp Asn Arg Tyr Thr Asp Pro Met Asp Lys Ala Phe
65                  70                  75                  80

Ala Arg Val Asp Ala Leu Phe Glu Phe Cys Glu Lys Leu Asn Ile Glu
                85                  90                  95
```

```
Tyr Phe Cys Phe His Asp Arg Asp Ile Ala Pro Glu Gly Lys Thr Leu
                100                 105                 110

Arg Glu Thr Asn Lys Ile Leu Asp Lys Val Val Glu Arg Ile Lys Glu
            115                 120                 125

Arg Met Lys Asp Ser Asn Val Lys Leu Leu Trp Gly Thr Ala Asn Leu
        130                 135                 140

Phe Ser His Pro Arg Tyr Met His Gly Ala Thr Thr Cys Ser Ala
145                 150                 155                 160

Asp Val Phe Ala Tyr Ala Ala Gln Val Lys Lys Ala Leu Glu Ile
                165                 170                 175

Thr Lys Glu Leu Gly Gly Glu Gly Tyr Val Phe Trp Gly Gly Arg Glu
            180                 185                 190

Gly Tyr Glu Thr Leu Leu Asn Thr Asp Leu Gly Phe Glu Leu Glu Asn
        195                 200                 205

Leu Ala Arg Phe Leu Arg Met Ala Val Asp Tyr Ala Lys Arg Ile Gly
210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Ser
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Leu Arg Met Ala Arg Ile
        275                 280                 285

Leu Gly Lys Leu Gly Ser Ile Asp Ala Asn Gln Gly Asp Leu Leu Leu
290                 295                 300

Gly Trp Asp Thr Asp Gln Phe Pro Thr Asn Val Tyr Asp Thr Thr Leu
305                 310                 315                 320

Ala Met Tyr Glu Val Ile Lys Ala Gly Gly Phe Thr Lys Gly Gly Leu
                325                 330                 335

Asn Phe Asp Ala Lys Val Arg Arg Ala Ser Tyr Lys Val Glu Asp Leu
            340                 345                 350

Phe Ile Gly His Ile Ala Gly Met Asp Thr Phe Ala Leu Gly Phe Lys
        355                 360                 365

Val Ala Tyr Lys Leu Val Lys Asp Gly Val Leu Asp Lys Phe Ile Glu
370                 375                 380

Glu Lys Tyr Arg Ser Phe Arg Glu Gly Ile Gly Arg Asp Ile Val Glu
385                 390                 395                 400

Gly Lys Val Asp Phe Glu Lys Leu Glu Glu Tyr Ile Ile Asp Lys Glu
                405                 410                 415

Thr Ile Glu Leu Pro Ser Gly Lys Gln Glu Tyr Leu Glu Ser Leu Ile
            420                 425                 430

Asn Ser Tyr Ile Val Lys Thr Ile Leu Glu Leu Arg
        435                 440

<210> SEQ ID NO 2
<211> LENGTH: 388
<212> TYPE: PRT
<213> ORGANISM: STREPTOMYCES MURINUS

<400> SEQUENCE: 2

Met Ser Phe Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30
```

```
Ala Leu Asp Pro Val Glu Thr Val Gln Arg Leu Ala Glu Leu Gly Ala
        35                  40                  45

Tyr Gly Val Thr Phe His Asp Asp Leu Ile Pro Phe Gly Ser Ser
 50                  55                  60

Asp Thr Glu Arg Glu Ser His Ile Lys Arg Phe Arg Gln Ala Leu Asp
 65                  70                  75                  80

Ala Thr Gly Met Thr Val Pro Met Ala Thr Thr Asn Leu Phe Thr His
                 85                  90                  95

Pro Val Phe Lys Asp Gly Gly Phe Thr Ala Asn Asp Arg Asp Val Arg
                100                 105                 110

Arg Tyr Ala Leu Arg Lys Thr Ile Gly Asn Ile Asp Leu Ala Ala Glu
             115                 120                 125

Leu Gly Ala Lys Thr Tyr Val Ala Trp Gly Gly Arg Glu Gly Ala Glu
130                 135                 140

Ser Gly Gly Ala Lys Asp Val Arg Asp Ala Leu Asp Arg Met Lys Glu
145                 150                 155                 160

Ala Phe Asp Leu Leu Gly Glu Tyr Val Thr Ala Gln Gly Tyr Asp Leu
                165                 170                 175

Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
            195                 200                 205

Pro Glu Leu Tyr Gly Val Asn Pro Glu Val Gly His Glu Gln Met Ala
210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Thr Ala Gly Tyr Glu Gly Pro Arg His Phe Asp Phe
            275                 280                 285

Lys Pro Pro Arg Thr Glu Asp Phe Asp Gly Val Trp Ala Ser Ala Ala
290                 295                 300

Gly Cys Met Arg Asn Tyr Leu Ile Leu Lys Asp Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Gln Pro Thr Ala Ala Asp Gly Leu Asp Ala Leu Leu Ala
            340                 345                 350

Asp Arg Ala Ala Phe Asp Phe Asp Val Asp Ala Ala Ala Ala Arg
            355                 360                 365

Gly Met Ala Phe Glu His Leu Asp Gln Leu Ala Met Asp His Leu Leu
370                 375                 380

Gly Ala Arg Gly
385

<210> SEQ ID NO 3
<211> LENGTH: 439
<212> TYPE: PRT
<213> ORGANISM: THERMOANAEROBACTERIUM THERMOSULFURIGENES

<400> SEQUENCE: 3

Met Asn Lys Tyr Phe Glu Asn Val Ser Lys Ile Lys Tyr Glu Gly Pro
```

-continued

```
 1               5                   10                  15
Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
                35                  40                  45

Trp His Thr Phe Thr Ala Asp Gly Thr Asp Gln Phe Gly Lys Ala Thr
 50                  55                  60

Met Gln Arg Pro Trp Asn His Tyr Thr Asp Pro Met Asp Ile Ala Lys
 65                  70                  75                  80

Ala Arg Val Glu Ala Ala Phe Glu Phe Phe Asp Lys Ile Asn Ala Pro
                85                  90                  95

Tyr Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
                115                 120                 125

Tyr Leu Lys Thr Ser Lys Thr Lys Val Leu Trp Gly Thr Ala Asn Leu
                130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Gly Glu Asn Tyr Val Phe Trp Gly Gly Arg Glu
                180                 185                 190

Gly Tyr Glu Thr Leu Leu Asn Thr Asp Met Glu Phe Glu Leu Asp Asn
                195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
                260                 265                 270

Thr Leu Ala Phe His Asp Phe Gln His Glu Leu Arg Tyr Ala Arg Ile
                275                 280                 285

Asn Gly Val Leu Gly Ser Ile Asp Ala Asn Thr Gly Asp Met Leu Leu
                290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
                340                 345                 350

Phe Leu Gly His Ile Ala Gly Met Asp Ala Phe Ala Lys Gly Phe Lys
                355                 360                 365

Val Ala Tyr Lys Leu Val Lys Asp Arg Val Phe Asp Lys Phe Ile Glu
                370                 375                 380

Glu Arg Tyr Ala Ser Tyr Lys Asp Gly Ile Gly Ala Asp Ile Val Ser
385                 390                 395                 400

Gly Lys Ala Asp Phe Arg Ser Leu Glu Lys Tyr Ala Leu Glu Arg Ser
                405                 410                 415

Gln Ile Val Asn Lys Ser Gly Arg Gln Glu Leu Leu Glu Ser Ile Leu
                420                 425                 430
```

Asn Gln Tyr Leu Phe Ala Glu
        435

<210> SEQ ID NO 4
<211> LENGTH: 368
<212> TYPE: PRT
<213> ORGANISM: DICTYOGLOMUS THERMOPHILUM

<400> SEQUENCE: 4

Met Pro Phe Val Asp His Arg Ala Gln Lys Ile Arg Arg Ser Lys Glu
1               5                   10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
        35                  40                  45

Tyr Val Glu Gln Lys Ser Ile Pro Glu Arg Ile Glu Met Ala Ala Glu
    50                  55                  60

Met Ala Lys Phe Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Ala
                85                  90                  95

Gly Ile Arg Leu Val Ala Val Pro Leu Ser Leu Phe Tyr Asp Lys Ile
            100                 105                 110

Phe Glu Phe Gly Ser Leu Ser Asn Pro Tyr Glu Lys Tyr Arg Lys Val
        115                 120                 125

Ala Tyr Glu Arg Leu Val Asn Gly Leu Lys Leu Val Lys Glu Ala Asn
130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
        195                 200                 205

Gly Ile Leu Ala Ala Arg Asp Ile Glu Ala Arg Leu Lys Asn Pro Glu
    210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
        275                 280                 285

Trp Asp Ser Thr Glu Ala Leu Leu Tyr Thr Leu Lys Met Val Gly Tyr
    290                 295                 300

Gln Gly Tyr Phe Gly Ile Asp Ile Asn Pro Glu Arg Met Pro Val Ile
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Lys

```
<210> SEQ ID NO 5
<211> LENGTH: 385
<212> TYPE: PRT
<213> ORGANISM: MARINACTINOSPORA THERMOTOLERANS

<400> SEQUENCE: 5

Met Ser Ser Tyr Arg Pro Glu Pro Glu Asp Lys Phe Ser Phe Gly Leu
1               5                   10                  15

Trp Thr Val Gly Trp Arg Gly Val Asn Thr Phe Gly Asp Ala Val Arg
            20                  25                  30

Pro Pro Leu Asp Pro Ala Glu Ala Val His Arg Leu Ala Gly Leu Gly
        35                  40                  45

Ala Tyr Gly Ile Thr Phe His Asp Asp Leu Ile Pro Pro Gly Ser
    50                  55                  60

Ser Ala Ala Glu Arg Asp Ala Ile Leu Gly Arg Phe Arg Lys Ala Leu
65                  70                  75                  80

Asp Glu Thr Gly Leu Thr Val Pro Met Ala Thr Val Asn Leu Phe Ser
                85                  90                  95

His Pro Val Phe Arg Asp Gly Phe Thr Ser Asn Ser Arg Ala Thr
            100                 105                 110

Arg Arg Tyr Ala Ile Arg Lys Ala Val Arg Ala Ile Asp Leu Ala Ala
            115                 120                 125

Glu Leu Gly Ala Arg Thr Phe Val Cys Trp Gly Gly Gln Asp Gly Ala
130                 135                 140

Glu Thr Glu Ala Gly Lys Asp Asp Arg Ala Ala Leu Glu Arg Leu Arg
145                 150                 155                 160

Glu Ala Phe Asn Leu Met Cys Gly Tyr Val Arg Glu Gln Gly Tyr Asp
                165                 170                 175

Leu Arg Phe Ala Val Glu Pro Lys Pro Asn Glu Pro Arg Gly Asp Val
            180                 185                 190

Leu Leu Pro Thr Val Gly His Ala Leu Ala Phe Ile Gly Glu Leu Glu
        195                 200                 205

His Pro Glu Met Val Gly Val Asn Pro Glu Val Gly His Glu Gln Met
210                 215                 220

Ala Gly Leu Asn Phe Ala His Gly Val Ala Gln Ala Leu Trp His Gly
225                 230                 235                 240

Lys Leu Phe His Ile Asp Leu Asn Gly Gln Arg Gly Val Lys Tyr Asp
                245                 250                 255

Gln Asp Leu Arg Phe Gly Ala Gly Asp Val Lys Glu Ala Phe Phe Leu
            260                 265                 270

Val Asp Leu Leu Glu Arg Ser Gly Tyr Asp Gly Pro Arg His Phe Asp
        275                 280                 285

Phe Lys Pro Pro Arg Thr Glu Asp Val Asp Gly Val Trp Glu Ser Ala
290                 295                 300

Ala Ala Cys Met Arg Asn Tyr Leu Ile Leu Lys Glu Lys Ala Ala Ala
305                 310                 315                 320

Phe Arg Ala Asp Pro Glu Val Ala Asp Ala Leu Ala Ala Ser Arg Val
                325                 330                 335

Ala Glu Leu Ser Glu Pro Thr Leu Gly Thr Gly Glu Ser Leu Ala Asp
            340                 345                 350

Leu Leu Ala Glu Asp Phe Asp Val Asp Ala Ala Gly Glu Arg Gly Tyr
        355                 360                 365
```

```
His Phe Glu Arg Leu Asp Gln Leu Ala Met Asp His Leu Phe Gly Val
    370                 375                 380

Arg
385

<210> SEQ ID NO 6
<211> LENGTH: 441
<212> TYPE: PRT
<213> ORGANISM: BACILLUS STEAROTHERMOPHILUS

<400> SEQUENCE: 6

Met Pro Tyr Phe Asp Asn Ile Ser Thr Ile Ala Tyr Glu Gly Pro Ala
1               5                   10                  15

Ser Lys Asn Pro Leu Ala Phe Lys Phe Tyr Asn Pro Glu Glu Lys Val
            20                  25                  30

Gly Asp Lys Thr Met Glu Glu His Leu Arg Phe Ser Val Ala Tyr Trp
        35                  40                  45

His Thr Phe Thr Gly Asp Gly Ser Asp Pro Phe Gly Ala Gly Asn Met
    50                  55                  60

Ile Arg Pro Trp Asn Lys Tyr Ser Gly Met Asp Leu Ala Lys Ala Arg
65              70                  75                  80

Val Glu Ala Ala Phe Glu Phe Glu Lys Leu Asn Ile Pro Phe Phe
                85                  90                  95

Cys Phe His Asp Val Asp Ile Ala Pro Glu Gly Glu Thr Leu Lys Glu
            100                 105                 110

Thr Tyr Lys Asn Leu Asp Ile Ile Val Asp Met Ile Glu Glu Tyr Met
        115                 120                 125

Lys Thr Ser Lys Thr Lys Leu Leu Trp Asn Thr Ala Asn Leu Phe Thr
    130                 135                 140

His Pro Arg Phe Val His Gly Ala Ala Thr Ser Cys Asn Ala Asp Val
145                 150                 155                 160

Phe Ala Tyr Ala Ala Lys Val Lys Lys Gly Leu Glu Ile Ala Lys
                165                 170                 175

Arg Leu Gly Ala Glu Asn Tyr Val Phe Trp Gly Gly Arg Glu Gly Tyr
            180                 185                 190

Glu Thr Leu Leu Asn Thr Asp Met Lys Leu Glu Leu Asp Asn Leu Ala
        195                 200                 205

Arg Phe Leu His Met Ala Val Asp Tyr Ala Lys Glu Ile Gly Phe Asp
    210                 215                 220

Gly Gln Phe Leu Ile Glu Pro Lys Pro Lys Glu Pro Thr Lys His Gln
225                 230                 235                 240

Tyr Asp Phe Asp Val Ala Thr Ala Leu Ala Phe Leu Gln Thr Tyr Gly
                245                 250                 255

Leu Lys Asp Tyr Phe Lys Phe Asn Ile Glu Ala Asn His Ala Thr Leu
            260                 265                 270

Ala Gly His Thr Phe Glu His Glu Leu Arg Val Ala Arg Ile His Gly
        275                 280                 285

Met Leu Gly Ser Val Asp Ala Asn Gln Gly Asp Met Leu Leu Gly Trp
    290                 295                 300

Asp Thr Asp Glu Phe Pro Thr Leu Tyr Ser Thr Thr Leu Ala Met
305                 310                 315                 320

Tyr Glu Ile Leu Lys Asn Gly Gly Leu Gly Arg Gly Gly Leu Asn Phe
                325                 330                 335

Asp Ala Lys Val Arg Arg Gly Ser Phe Glu Pro Glu Asp Leu Phe Tyr
            340                 345                 350
```

```
Ala His Ile Ala Gly Met Asp Ser Phe Ala Val Gly Leu Lys Val Ala
            355                 360                 365

His Arg Leu Ile Glu Asp Arg Val Phe Asp Glu Phe Ile Glu Glu Arg
    370                 375                 380

Tyr Lys Ser Tyr Thr Glu Gly Ile Gly Arg Glu Ile Val Glu Gly Thr
385                 390                 395                 400

Ala Asp Phe His Lys Leu Glu Ala His Ala Leu Gln Leu Gly Glu Ile
                405                 410                 415

Gln Asn Gln Ser Gly Arg Gln Glu Arg Leu Lys Thr Leu Leu Asn Gln
            420                 425                 430

Tyr Leu Leu Glu Val Cys Ala Ala Arg
            435                 440

<210> SEQ ID NO 7
<211> LENGTH: 387
<212> TYPE: PRT
<213> ORGANISM: THERMUS THERMOPHILUS

<400> SEQUENCE: 7

Met Tyr Glu Pro Lys Pro Glu His Arg Phe Thr Phe Gly Leu Trp Thr
1               5                   10                  15

Val Gly Asn Val Gly Arg Asp Pro Phe Gly Asp Ala Val Arg Glu Arg
            20                  25                  30

Leu Asp Pro Val Tyr Val Val His Lys Leu Ala Glu Leu Gly Ala Tyr
        35                  40                  45

Gly Val Asn Leu His Asp Glu Asp Leu Ile Pro Arg Gly Thr Pro Pro
    50                  55                  60

Gln Glu Arg Asp Gln Ile Val Arg Arg Phe Lys Lys Ala Leu Asp Glu
65                  70                  75                  80

Thr Gly Leu Lys Val Pro Met Val Thr Ala Asn Leu Phe Ser Asp Pro
                85                  90                  95

Ala Phe Lys Asp Gly Ala Phe Thr Ser Pro Asp Pro Trp Val Arg Ala
            100                 105                 110

Tyr Ala Leu Arg Lys Ser Leu Glu Thr Met Asp Leu Gly Ala Glu Leu
        115                 120                 125

Gly Ala Glu Ile Tyr Val Val Trp Pro Gly Arg Glu Gly Ala Glu Val
    130                 135                 140

Glu Ala Thr Gly Lys Ala Arg Lys Val Trp Asp Trp Val Arg Glu Ala
145                 150                 155                 160

Leu Asn Phe Met Ala Ala Tyr Ala Glu Asp Gln Gly Tyr Gly Tyr Arg
                165                 170                 175

Phe Ala Leu Glu Pro Lys Pro Asn Glu Pro Arg Gly Asp Ile Tyr Phe
            180                 185                 190

Ala Thr Val Gly Ser Met Leu Ala Phe Ile His Thr Leu Asp Arg Pro
        195                 200                 205

Glu Arg Phe Gly Leu Asn Pro Glu Phe Ala His Glu Thr Met Ala Gly
    210                 215                 220

Leu Asn Phe Val His Ala Val Ala Gln Ala Leu Asp Ala Gly Lys Leu
225                 230                 235                 240

Phe His Ile Asp Leu Asn Asp Gln Arg Met Ser Arg Phe Asp Gln Asp
                245                 250                 255

Leu Arg Phe Gly Ser Glu Asn Leu Lys Ala Ala Phe Phe Leu Val Asp
            260                 265                 270

Leu Leu Glu Ser Ser Gly Tyr Gln Gly Pro Arg His Phe Asp Ala His
```

```
            275                 280                 285
Ala Leu Arg Thr Glu Asp Glu Gly Val Trp Ala Phe Ala Arg Gly
    290                 295                 300

Cys Met Arg Thr Tyr Leu Ile Leu Lys Glu Arg Ala Glu Ala Phe Arg
305                 310                 315                 320

Glu Asp Pro Glu Val Lys Glu Leu Leu Ala Tyr Tyr Gln Glu Asp
                325                 330                 335

Pro Ala Ala Leu Ala Leu Leu Gly Pro Tyr Ser Arg Glu Lys Ala Glu
            340                 345                 350

Ala Leu Lys Arg Ala Glu Leu Pro Leu Glu Ala Lys Arg Arg Gly
    355                 360                 365

Tyr Ala Leu Glu Arg Leu Asp Gln Leu Ala Val Glu Tyr Leu Leu Gly
370                 375                 380

Val Arg Gly
385

<210> SEQ ID NO 8
<211> LENGTH: 387
<212> TYPE: PRT
<213> ORGANISM: THERMUS CALDOPHILUS

<400> SEQUENCE: 8

Met Tyr Glu Pro Lys Pro Glu His Arg Phe Thr Phe Gly Leu Trp Thr
1               5                   10                  15

Val Gly Asn Val Gly Arg Asp Pro Phe Gly Asp Ala Val Arg Glu Arg
                20                  25                  30

Leu Asp Pro Val Tyr Val Gly His Lys Leu Ala Glu Leu Gly Val His
            35                  40                  45

Gly Val Asn Leu His Asp Glu Asp Leu Ile Pro Arg Gly Thr Pro Pro
    50                  55                  60

Gln Glu Arg Asp Gln Ile Val Arg Arg Phe Lys Arg Ala Leu Asp Glu
65                  70                  75                  80

Thr Gly Leu Lys Val Pro Met Val Thr Gly Asn Leu Phe Ser Asp Pro
                85                  90                  95

Gly Phe Lys Asp Gly Gly Phe Thr Ser Arg Asp Pro Trp Val Arg Ala
            100                 105                 110

Tyr Ala Phe Arg Lys Ser Leu Glu Thr Met Asp Leu Gly Ala Glu Leu
    115                 120                 125

Gly Ala Glu Ile Tyr Val Val Trp Pro Gly Arg Glu Gly Ala Glu Val
130                 135                 140

Glu Ala Thr Gly Lys Ala Arg Lys Val Trp Asp Trp Val Arg Glu Pro
145                 150                 155                 160

Leu Asn Phe Met Ala Ala Tyr Ala Glu Asp Gln Gly Tyr Gly Tyr Arg
                165                 170                 175

Phe Ala Leu Glu Pro Lys Pro Asn Glu Pro Arg Gly Asp Ile Tyr Phe
            180                 185                 190

Ala Thr Val Gly Ser Met Leu Ala Leu Ile His Thr Leu Glu Arg Pro
    195                 200                 205

Glu Arg Phe Gly Leu Asn Pro Glu Phe Ala His Glu Thr Met Ala Gly
210                 215                 220

Leu Asn Phe Val His Ala Val Ala Gln Ala Leu Asp Ala Gly Lys Leu
225                 230                 235                 240

Leu His Ile Asp Leu Asn Gly Gln Arg Met Asn Arg Phe Asp Gln Asp
                245                 250                 255
```

Leu Arg Phe Gly Ser Glu Asn Leu Lys Ala Ala Phe Leu Leu Val Asp
        260                 265                 270

Leu Leu Glu Ser Ser Gly Tyr Gln Gly Pro Arg His Phe Asp Ala His
        275                 280                 285

Ala Leu Arg Thr Glu Asp Glu Gly Val Trp Ala Phe Ala Arg Gly
        290                 295                 300

Cys Met Arg Thr Tyr Leu Ile Leu Lys Glu Arg Ala Glu Ala Phe Arg
305                 310                 315                 320

Glu Asp Pro Glu Val Lys Glu Leu Leu Ala Ala Tyr Tyr Gln Glu Asp
                    325                 330                 335

Pro Ala Ala Leu Pro Leu Met Asp Pro Tyr Ser His Glu Lys Ala Glu
                340                 345                 350

Ala Leu Lys Arg Ala Glu Leu Pro Leu Glu Ala Lys Arg His Arg Gly
            355                 360                 365

Tyr Ala Leu Glu Arg Leu Asp Gln Leu Ala Val Glu Tyr Leu Leu Gly
        370                 375                 380

Val Arg Gly
385

<210> SEQ ID NO 9
<211> LENGTH: 387
<212> TYPE: PRT
<213> ORGANISM: STREPTOMYCES OLIVOCHROMOGENES

<400> SEQUENCE: 9

Met Ser Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Thr Val Gln Arg Leu Ala Glu Leu Gly Ala
        35                  40                  45

His Gly Val Thr Phe His Asp Asp Asp Leu Ile Pro Phe Gly Ser Ser
    50                  55                  60

Asp Thr Glu Arg Glu Ser His Ile Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Gly Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Thr Tyr Val Ala Trp Gly Gly Arg Glu Gly Ala Glu
    130                 135                 140

Ser Gly Ala Ala Lys Asp Val Arg Val Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Tyr Glu Gly Pro Arg His Phe Asp Phe
        275                 280                 285

Lys Pro Pro Arg Thr Glu Asp Ile Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ser Arg Leu Asp
                325                 330                 335

Glu Leu Ala Gln Pro Thr Ala Ala Asp Gly Val Gln Glu Leu Leu Ala
            340                 345                 350

Asp Arg Thr Ala Phe Glu Asp Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg
385

<210> SEQ ID NO 10
<211> LENGTH: 441
<212> TYPE: PRT
<213> ORGANISM: ANOXYBACILLUS GONENSIS

<400> SEQUENCE: 10

Met Ala Tyr Phe Glu Asn Val Asp Lys Val Val Tyr Glu Gly Pro Ala
1               5                   10                  15

Ser Glu Asn Pro Leu Ala Phe Lys Phe Tyr Asn Pro Glu Glu Lys Val
            20                  25                  30

Gly Asp Lys Thr Met Glu Glu His Leu Arg Phe Ser Val Ala Tyr Trp
        35                  40                  45

His Thr Phe Val Gly Asp Gly Ala Asp Pro Phe Gly Val Gly Thr Ala
    50                  55                  60

Ile Arg Pro Trp Asn Arg Tyr Ser Gly Met Asp Leu Ala Lys Ala Arg
65                  70                  75                  80

Val Glu Ala Ala Phe Glu Leu Phe Asp Lys Leu Asn Ile Pro Phe Phe
                85                  90                  95

Cys Phe His Asp Val Asp Ile Ala Pro Glu Gly Ala Thr Leu Lys Glu
            100                 105                 110

Thr Tyr Gln Asn Leu Asp Thr Ile Val Asp Met Ile Glu Glu Tyr Met
        115                 120                 125

Lys Thr Ser Lys Thr Lys Leu Leu Trp Asn Thr Ala Asn Leu Phe Thr
    130                 135                 140

His Pro Arg Phe Val His Gly Ala Ala Thr Ser Cys Asn Ala Asp Val
145                 150                 155                 160

Phe Ala Tyr Ala Ala Ala Lys Val Lys Lys Gly Leu Glu Ile Ala Lys
                165                 170                 175

Arg Leu Gly Ala Glu Asn Tyr Val Phe Trp Gly Gly Arg Glu Gly Tyr
            180                 185                 190

Glu Thr Leu Leu Asn Thr Asn Met Lys Leu Glu Leu Asp Asn Leu Ala
        195                 200                 205

Arg Phe Leu His Met Ala Val Asp Tyr Ala Lys Glu Ile Gly Phe Asp

```
                              210                   215                   220
        Gly Gln Phe Leu Ile Glu Pro Lys Pro Lys Glu Pro Thr Lys His Gln
        225                 230                 235                 240

Tyr Asp Phe Asp Val Ala Thr Ala Leu Ala Phe Leu Gln Thr Tyr Gly
                            245                 250                 255

Leu Lys Asp Tyr Phe Lys Phe Asn Ile Glu Ala Asn His Ala Thr Leu
                        260                 265                 270

Ala Gly His Thr Phe Glu His Glu Leu Arg Val Ala Arg Ile His Gly
                    275                 280                 285

Met Leu Gly Ser Val Asp Ala Asn Gln Gly Asp Pro Leu Leu Gly Trp
        290                 295                 300

Asp Thr Asp Glu Phe Pro Thr Asp Leu Tyr Ser Thr Thr Leu Ala Met
        305                 310                 315                 320

Tyr Glu Ile Leu Gln Asn Gly Gly Leu Gly Lys Gly Gly Leu Asn Phe
                                325                 330                 335

Asp Ala Lys Val Arg Arg Gly Ser Phe Glu Pro Glu Asp Leu Phe Tyr
                        340                 345                 350

Ala His Ile Ala Gly Met Asp Ser Phe Ala Ile Gly Leu Lys Val Ala
                    355                 360                 365

Tyr Arg Leu Ile Glu Asp Arg Val Phe Glu Ser Val Val Glu Glu Arg
        370                 375                 380

Tyr Lys Ser Tyr Thr Glu Gly Ile Gly Arg Asp Ile Ile Asp Gly Lys
        385                 390                 395                 400

Ala Asp Phe His Thr Leu Glu Ala Tyr Ala Leu Asn Leu Arg Asp Ile
                        405                 410                 415

Ser Asn Arg Ser Gly Arg Gln Glu Arg Leu Lys Thr Leu Leu Asn Gln
                    420                 425                 430

Tyr Leu Leu Glu Val Cys Val Ala Arg
                        435                 440

<210> SEQ ID NO 11
<211> LENGTH: 395
<212> TYPE: PRT
<213> ORGANISM: ARTHROBACTER NRRL B3728

<400> SEQUENCE: 11

Met Ser Val Gln Pro Thr Pro Ala Asp His Phe Thr Phe Gly Leu Trp
        1               5                   10                  15

Thr Val Gly Trp Thr Gly Ala Asp Pro Phe Gly Val Ala Thr Arg Lys
                        20                  25                  30

Asn Leu Asp Pro Val Glu Ala Val His Lys Leu Ala Glu Leu Gly Ala
                    35                  40                  45

Tyr Gly Ile Thr Phe His Asp Asn Asp Leu Ile Pro Phe Asp Ala Thr
                50                  55                  60

Glu Ala Glu Arg Glu Lys Ile Leu Gly Asp Phe Asn Gln Ala Leu Lys
        65                  70                  75                  80

Asp Thr Gly Leu Lys Val Pro Met Val Thr Thr Asn Leu Phe Ser His
                        85                  90                  95

Pro Val Phe Lys Asp Gly Gly Phe Thr Ser Asn Asp Arg Ser Ile Arg
                    100                 105                 110

Arg Phe Ala Leu Ala Lys Val Leu His Asn Ile Asp Leu Ala Ala Glu
                115                 120                 125

Met Gly Ala Glu Thr Phe Val Met Trp Gly Gly Arg Glu Gly Ser Glu
            130                 135                 140
```

Tyr Asp Gly Ser Lys Asp Leu Ala Ala Ala Leu Asp Arg Met Arg Glu
145                 150                 155                 160

Gly Val Asp Thr Ala Ala Gly Tyr Ile Lys Asp Lys Gly Tyr Asn Leu
            165                 170                 175

Arg Ile Ala Leu Glu Pro Lys Pro Asn Glu Pro Arg Gly Asp Ile Phe
        180                 185                 190

Leu Pro Thr Val Gly His Gly Leu Ala Phe Ile Glu Gln Leu Glu His
    195                 200                 205

Gly Asp Ile Val Gly Leu Asn Pro Glu Thr Gly His Glu Gln Met Ala
210                 215                 220

Gly Leu Asn Phe Thr His Gly Ile Ala Gln Ala Leu Trp Ala Glu Lys
225                 230                 235                 240

Leu Phe His Ile Asp Leu Asn Gly Gln Arg Gly Ile Lys Tyr Asp Gln
            245                 250                 255

Asp Leu Val Phe Gly His Gly Asp Leu Thr Ser Ala Phe Phe Thr Val
        260                 265                 270

Asp Leu Leu Glu Asn Gly Phe Pro Asn Gly Gly Pro Lys Tyr Thr Gly
    275                 280                 285

Pro Arg His Phe Asp Tyr Lys Pro Ser Arg Thr Asp Gly Tyr Asp Gly
290                 295                 300

Val Trp Asp Ser Ala Lys Ala Asn Met Ser Met Tyr Leu Leu Leu Lys
305                 310                 315                 320

Glu Arg Ala Leu Ala Phe Arg Ala Asp Pro Glu Val Gln Glu Ala Met
            325                 330                 335

Lys Thr Ser Gly Val Phe Glu Leu Gly Glu Thr Thr Leu Asn Ala Gly
        340                 345                 350

Glu Ser Ala Ala Asp Leu Met Asn Asp Ser Ala Ser Phe Ala Gly Phe
    355                 360                 365

Asp Ala Glu Ala Ala Glu Arg Asn Phe Ala Phe Ile Arg Leu Asn
370                 375                 380

Gln Leu Ala Ile Glu His Leu Leu Gly Ser Arg
385                 390                 395

<210> SEQ ID NO 12
<211> LENGTH: 439
<212> TYPE: PRT
<213> ORGANISM: HALOTHERMOTHRIX ORENII

<400> SEQUENCE: 12

Met Glu Val Phe Lys Asn Val Pro Gln Thr Ile Lys Tyr Glu Gly Lys
1               5                   10                  15

Asp Ser Asp Asn Pro Leu Ala Phe Lys Tyr Tyr Asn Pro Glu Glu Lys
            20                  25                  30

Val Gly Gly Lys Thr Met Glu His Leu Arg Phe Ser Val Ala Tyr
        35                  40                  45

Trp His Thr Leu Thr Gly Asp Gly Ser Asp Pro Phe Gly Met Gly Thr
    50                  55                  60

Met Leu Arg Pro Trp Asp Thr Ala Thr Asp Pro Met Glu Leu Ala Lys
65                  70                  75                  80

Ala Arg Val Arg Ala Ala Phe Glu Phe Met Ser Lys Leu Gly Val Lys
            85                  90                  95

Tyr Phe Cys Phe His Asp Arg Asp Ile Ala Pro Glu Gly Arg Thr Leu
        100                 105                 110

Ala Glu Thr Asn Lys Asn Leu Asp Glu Ile Val Ser Leu Ile Lys Glu
    115                 120                 125

```
Leu Met Asp Glu Thr Gly Ile Lys Leu Leu Trp Gly Thr Ala Asn Leu
130                 135                 140

Phe Ser Asn Pro Arg Phe Val His Gly Ala Ala Thr Ser Pro Asn Ala
145                 150                 155                 160

Asp Val Phe Ala Tyr Ala Ala Ala Gln Val Lys Lys Ala Met Glu Ile
                165                 170                 175

Thr Lys Glu Leu Gly Gly Glu Asn Tyr Val Phe Trp Gly Gly Arg Glu
            180                 185                 190

Gly Tyr Glu Thr Leu Leu Asn Thr Asp Met Glu Leu Glu Gln Glu Asn
        195                 200                 205

Phe Ala Arg Phe Leu His Met Ala Val Asp Tyr Ala Arg Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Ala Ala Thr Val Ile Ser Phe Leu Lys Lys
                245                 250                 255

Tyr Asp Leu Asp Lys His Phe Lys Leu Asn Ile Glu Ala Asn His Ala
            260                 265                 270

Thr Leu Ala Gly His Thr Phe Gln His Glu Leu His Val Ser Arg Ile
        275                 280                 285

Asn Gly Met Leu Gly Ser Val Asp Ala Asn Gln Gly Asp Leu Leu Leu
    290                 295                 300

Gly Trp Asp Thr Asp Gln Phe Pro Thr Asn Ile Tyr Glu Thr Thr Leu
305                 310                 315                 320

Ala Met Tyr Glu Ile Leu Lys Asn Gly Gly Leu Glu Pro Gly Gly Leu
                325                 330                 335

Asn Phe Asp Ala Lys Val Arg Arg Ala Ser Phe Glu Pro Val Asp Leu
            340                 345                 350

Phe Tyr Ala His Ile Ala Gly Met Asp Ala Phe Ala Arg Gly Leu Lys
        355                 360                 365

Val Ala His Lys Leu Leu Glu Ser Gly Glu Leu Glu Asp Phe Ile Ser
    370                 375                 380

Glu Arg Tyr Lys Ser Tyr Arg Asn Gly Ile Gly Glu Lys Ile Val Lys
385                 390                 395                 400

Gly Glu Val Gly Phe Lys Glu Leu Glu Asp Tyr Ala Leu Asn Asn Gly
                405                 410                 415

Lys Ile Thr Asn Val Ser Gly Arg Gln Glu Leu Leu Glu Ser Ile Val
            420                 425                 430

Asn Lys Tyr Ile Ile Glu Ala
        435

<210> SEQ ID NO 13
<211> LENGTH: 445
<212> TYPE: PRT
<213> ORGANISM: BACILLUS COAGULANS

<400> SEQUENCE: 13

Met Met Ala Tyr Phe Pro Asn Val Ser Lys Ile Thr Tyr Ser Gly Lys
1               5                   10                  15

Gln Leu Lys Ser Gly Leu Ser Phe Asn His Tyr Asn Pro Lys Glu Leu
            20                  25                  30

Val Gly Gly Lys Thr Met Glu Glu Gln Leu Arg Phe Ser Val Ala Phe
        35                  40                  45

Trp His Thr Phe Thr Glu Ser Gly Thr Asp Pro Phe Gly Ala Gly Ser
```

```
            50                  55                  60
Lys Ile Arg Pro Trp Asp Arg Phe Thr Gly Met Asp Leu Ala Lys Ala
65                  70                  75                  80

Arg Val Glu Ala Ala Phe Glu Phe Glu Lys Leu Gly Asn Pro Tyr
                85                  90                  95

Phe Cys Phe His Asp Arg Asp Ile Ala Pro Glu Gly Asp Thr Leu Arg
                100                 105                 110

Glu Thr Asn Lys Asn Leu Asp Val Ile Val Ala Met Ile Lys Asp Tyr
                115                 120                 125

Met Lys Thr Ser Lys Val Lys Leu Leu Trp Asn Thr Ala Asn Met Phe
130                 135                 140

Thr Asn Pro Arg Phe Val His Gly Ala Ala Ser Ser Cys Asn Ala Asp
145                 150                 155                 160

Val Phe Ala Tyr Ala Ala Ala Gln Val Lys Lys Gly Leu Glu Val Gly
                165                 170                 175

Lys Glu Leu Gly Ala Glu Asn Tyr Val Phe Trp Gly Gly Arg Glu Gly
                180                 185                 190

Tyr Glu Thr Leu Leu Asn Thr Asp Leu Lys Leu Glu Gln Asp Asn Leu
                195                 200                 205

Ala Arg Phe Phe His Met Ala Val Asp Tyr Ala Lys Glu Ile Gly Phe
210                 215                 220

Asp Ala Gln Phe Leu Leu Glu Pro Lys Pro Lys Glu Pro Thr Lys His
225                 230                 235                 240

Gln Tyr Asp Phe Asp Ala Ala Thr Thr Ile Ala Phe Leu Lys Thr Tyr
                245                 250                 255

Asp Leu Asp Gln His Phe Lys Leu Asn Leu Glu Ala Asn His Ala Thr
                260                 265                 270

Leu Ala Gly His Thr Phe Glu His Glu Ile Arg Val Ala Arg Thr His
                275                 280                 285

Gly Leu Leu Gly Ser Leu Asp Ala Asn Gln Gly Asp Pro Leu Leu Gly
290                 295                 300

Trp Asp Thr Asp Glu Phe Pro Thr Asp Leu Tyr Ser Thr Thr Leu Ala
305                 310                 315                 320

Met Tyr Glu Val Leu Lys Asn Gly Gly Leu Gly Arg Gly Gly Leu Asn
                325                 330                 335

Phe Asp Ala Lys Thr Arg Arg Ala Ser Phe Thr Asp Glu Asp Leu Phe
                340                 345                 350

Tyr Ala His Ile Ala Gly Met Asp Ser Phe Ala Leu Gly Leu Lys Val
                355                 360                 365

Ala Asn Arg Leu Ile Glu Asp Arg Val Phe Asp Ala Phe Ile Glu Glu
370                 375                 380

Arg Tyr Ser Ser Tyr Lys Glu Gly Ile Gly Ala Asp Ile Val Ser Gly
385                 390                 395                 400

Lys Ala Asp Phe Lys Ser Leu Glu Asn Tyr Ile Leu Asp Lys Lys Glu
                405                 410                 415

Ile Ile Asn Gln Ser Gly Arg Leu Glu Gln Leu Lys Asn Thr Leu Asn
                420                 425                 430

His Tyr Ile Val Gln Glu Ala Tyr Gln Ser Val Asn Ala
                435                 440                 445

<210> SEQ ID NO 14
<211> LENGTH: 388
<212> TYPE: PRT
<213> ORGANISM: STREPTOMYCES RUBIGINOSUS
```

<400> SEQUENCE: 14

```
Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Arg
            20                  25                  30

Ala Leu Asp Pro Val Glu Ser Val Arg Arg Leu Ala Glu Leu Gly Ala
        35                  40                  45

His Gly Val Thr Phe His Asp Asp Leu Ile Pro Phe Gly Ser Ser
    50                  55                  60

Asp Ser Glu Arg Glu Glu His Val Lys Arg Phe Arg Gln Ala Leu Asp
65                  70                  75                  80

Asp Thr Gly Met Lys Val Pro Met Ala Thr Thr Asn Leu Phe Thr His
                85                  90                  95

Pro Val Phe Lys Asp Gly Gly Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Glu Thr Tyr Val Ala Trp Gly Gly Arg Glu Gly Ala Glu
130                 135                 140

Ser Gly Gly Ala Lys Asp Val Arg Asp Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Tyr Gly Val Asn Pro Glu Val Gly His Glu Gln Met Ala
210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Asn Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Tyr Ser Gly Pro Arg His Phe Asp Phe
        275                 280                 285

Lys Pro Pro Arg Thr Glu Asp Phe Asp Gly Val Trp Ala Ser Ala Ala
290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ser Arg Leu Asp
                325                 330                 335

Glu Leu Ala Arg Pro Thr Ala Ala Asp Gly Leu Gln Ala Leu Leu Asp
            340                 345                 350

Asp Arg Ser Ala Phe Glu Glu Phe Asp Val Asp Ala Ala Ala Ala Arg
        355                 360                 365

Gly Met Ala Phe Glu Arg Leu Asp Gln Leu Ala Met Asp His Leu Leu
370                 375                 380

Gly Ala Arg Gly
385
```

```
<210> SEQ ID NO 15
<211> LENGTH: 440
<212> TYPE: PRT
<213> ORGANISM: ESCHERICHIA COLI

<400> SEQUENCE: 15

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
    290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ala Leu Lys
        355                 360                 365

Ile Ala Ala Arg Met Ile Glu Asp Gly Glu Leu Asp Lys Arg Ile Ala
    370                 375                 380
```

Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His His
            405                 410                 415

Leu Ser Pro Val His Gln Ser Gly Arg Gln Glu Gln Leu Glu Asn Leu
            420                 425                 430

Val Asn His Tyr Leu Phe Asp Lys
        435                 440

<210> SEQ ID NO 16
<211> LENGTH: 439
<212> TYPE: PRT
<213> ORGANISM: CLOSTRIDIUM CELLULOVORANS

<400> SEQUENCE: 16

Met Arg Glu Tyr Phe Ala Asn Val Pro Lys Ile Lys Tyr Glu Gly Lys
1               5                   10                  15

Asp Ser Lys Asn Pro Leu Ala Phe Lys Tyr Tyr Asn Pro Asp Glu Val
            20                  25                  30

Val Gly Gly Lys Thr Met Lys Glu His Leu Arg Phe Thr Leu Ser Tyr
        35                  40                  45

Trp His Thr Leu Thr Gly Ala Gly Ser Asp Pro Phe Gly Val Gly Thr
    50                  55                  60

Met Leu Arg Pro Trp Asp Cys Ala Glu Asp Met Glu Leu Ala Lys
65                  70                  75                  80

Met Arg Met Glu Ala Asn Phe Glu Leu Met Asp Lys Leu Gly Ile Glu
                85                  90                  95

Tyr Phe Ala Phe His Asp Arg Asp Ile Ala Pro Glu Gly Lys Thr Leu
            100                 105                 110

Ala Asp Thr Asn Glu Lys Leu Asp Glu Ile Val Ala Tyr Cys Lys Glu
            115                 120                 125

Leu Met Gln Lys His Gly Lys Lys Leu Leu Trp Gly Thr Ala Asn Met
    130                 135                 140

Phe Gly Asn Pro Arg Phe Val His Gly Ala Ala Thr Thr Cys Asn Ala
145                 150                 155                 160

Asp Val Phe Ala Tyr Ala Ala Ala Gln Thr Lys Lys Ala Met Asp Val
                165                 170                 175

Thr Lys Glu Leu Gly Gly Glu Asn Tyr Val Phe Trp Gly Gly Arg Glu
            180                 185                 190

Gly Tyr Glu Thr Leu Leu Asn Thr Asp Leu Gly Leu Glu Gln Asp Asn
        195                 200                 205

Leu Ala Arg Phe Phe Gln Met Ala Val Asp Tyr Ala Lys Lys Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Val Leu Gly Phe Leu Arg Lys
                245                 250                 255

Tyr Asn Leu Glu Lys Tyr Phe Lys Met Asn Ile Glu Ala Asn His Ala
            260                 265                 270

Thr Leu Ala Gln His Thr Phe Gln His Glu Val Ala Val Ala Arg Val
        275                 280                 285

Asn Gly Val Leu Gly Ser Leu Asp Val Asn Gln Gly Asp Pro Asn Leu
    290                 295                 300

Gly Trp Asp Thr Asp Gln Phe Pro Thr Asn Ile Tyr Asp Ala Thr Met
305                 310                 315                 320

```
Val Met Tyr Glu Val Leu Lys Asn Gly Gly Ile Ala Pro Gly Gly Leu
            325                 330                 335

Asn Phe Asp Ala Lys Thr Arg Arg Ala Ser Phe Glu Pro Glu Asp Leu
            340                 345                 350

Phe Leu Ser Tyr Ile Ala Gly Met Asp Thr Met Ala Lys Gly Leu Arg
            355                 360                 365

Val Ala Tyr Ser Leu Leu Asp Asp Ala Val Leu Glu Asn Asn Thr Ser
        370                 375                 380

Glu Arg Tyr Lys Thr Phe Ser Glu Gly Ile Gly Lys Asp Ile Val Glu
385                 390                 395                 400

Gly Lys Val Asp Phe Glu Ser Leu Glu Lys Tyr Ala Leu Glu Asn Ser
                405                 410                 415

Val Ile Ser Asn Lys Ser Gly Arg Gln Glu Tyr Leu Glu Ser Val Val
            420                 425                 430

Asn Gln Tyr Ile Phe Asn Asp
            435

<210> SEQ ID NO 17
<211> LENGTH: 445
<212> TYPE: PRT
<213> ORGANISM: BACILLUS SUBTILIS

<400> SEQUENCE: 17

Met Ala Gln Ser His Ser Ser Val Asn Tyr Phe Gly Ser Val Asn
1               5                   10                  15

Lys Val Val Phe Glu Gly Lys Ala Ser Thr Asn Pro Leu Ala Phe Lys
            20                  25                  30

Tyr Tyr Asn Pro Gln Glu Val Ile Gly Gly Lys Thr Met Lys Glu His
            35                  40                  45

Leu Arg Phe Ser Ile Ala Tyr Trp His Thr Phe Thr Ala Asp Gly Thr
        50                  55                  60

Asp Val Phe Gly Ala Ala Thr Met Gln Arg Pro Trp Asp His Tyr Lys
65                  70                  75                  80

Gly Met Asp Leu Ala Arg Ala Arg Val Glu Ala Ala Phe Glu Met Phe
                85                  90                  95

Glu Lys Leu Asp Ala Pro Phe Phe Ala Phe His Asp Arg Asp Ile Ala
            100                 105                 110

Pro Glu Gly Ser Thr Leu Lys Glu Thr Asn Gln Asn Leu Asp Ile Ile
            115                 120                 125

Val Gly Met Ile Lys Asp Tyr Met Arg Asp Ser Asn Val Lys Leu Leu
        130                 135                 140

Trp Asn Thr Ala Asn Met Phe Thr Asn Pro Arg Phe Val His Gly Ala
145                 150                 155                 160

Ala Thr Ser Cys Asn Ala Asp Val Phe Ala Tyr Ala Ala Ala Gln Val
                165                 170                 175

Lys Lys Gly Leu Glu Thr Ala Lys Glu Leu Gly Ala Glu Asn Tyr Val
            180                 185                 190

Phe Trp Gly Gly Arg Glu Gly Tyr Glu Thr Leu Leu Asn Thr Asp Leu
        195                 200                 205

Lys Phe Glu Leu Asp Asn Leu Ala Arg Phe Met His Met Ala Val Asp
    210                 215                 220

Tyr Ala Lys Glu Ile Glu Tyr Thr Gly Gln Phe Leu Ile Glu Pro Lys
225                 230                 235                 240

Pro Lys Glu Pro Thr Thr His Gln Tyr Asp Thr Asp Ala Ala Thr Thr
```

```
            245                 250                 255
Ile Ala Phe Leu Lys Gln Tyr Gly Leu Asp Asn His Phe Lys Leu Asn
            260                 265                 270

Leu Glu Ala Asn His Ala Thr Leu Ala Gly His Thr Phe Glu His Glu
        275                 280                 285

Leu Arg Met Ala Arg Val His Gly Leu Leu Gly Ser Val Asp Ala Asn
    290                 295                 300

Gln Gly His Pro Leu Leu Gly Trp Asp Thr Asp Glu Phe Pro Thr Asp
305                 310                 315                 320

Leu Tyr Ser Thr Thr Leu Ala Met Tyr Glu Ile Leu Gln Asn Gly Gly
            325                 330                 335

Leu Gly Ser Gly Gly Leu Asn Phe Asp Ala Lys Val Arg Arg Ser Ser
            340                 345                 350

Phe Glu Pro Asp Asp Leu Val Tyr Ala His Ile Ala Gly Met Asp Ala
            355                 360                 365

Phe Ala Arg Gly Leu Lys Val Ala His Lys Leu Ile Glu Asp Arg Val
        370                 375                 380

Phe Glu Asp Val Ile Gln His Arg Tyr Arg Ser Phe Thr Glu Gly Ile
385                 390                 395                 400

Gly Leu Glu Ile Thr Glu Gly Arg Ala Asn Phe His Thr Leu Glu Gln
            405                 410                 415

Tyr Ala Leu Asn Asn Lys Thr Ile Lys Asn Glu Ser Gly Arg Gln Glu
            420                 425                 430

Arg Leu Lys Ala Ile Leu Asn Gln Tyr Ile Leu Glu Val
        435                 440                 445

<210> SEQ ID NO 18
<211> LENGTH: 448
<212> TYPE: PRT
<213> ORGANISM: BACILLUS LICHENIFORMIS

<400> SEQUENCE: 18

Met Phe Phe Lys Asn Val Gly Met Ile Glu Tyr Glu Gly Ala Asp Ser
1               5                   10                  15

Glu Asn Pro Tyr Ala Phe Lys Tyr Tyr Asn Pro Asp Glu Tyr Val Gly
            20                  25                  30

Gly Lys Thr Met Lys Glu His Leu Arg Phe Ala Val Ala Tyr Trp His
        35                  40                  45

Thr Phe Asp Ala Asp Gly Lys Asp Pro Phe Gly Asp Gly Thr Met Phe
    50                  55                  60

Arg Ala Trp Asn Arg Leu Thr Tyr Pro Leu Asp Lys Ala Lys Ala Arg
65                  70                  75                  80

Ala Glu Ser Ala Phe Glu Phe Phe Glu Lys Leu Gly Val Pro Tyr Phe
                85                  90                  95

Cys Phe His Asp Val Asp Ile Val Asp Glu Gly Ala Thr Leu Arg Glu
            100                 105                 110

Thr Phe Ala Tyr Leu Asp Gln Met Ser Ser Phe Leu Lys Glu Met Met
        115                 120                 125

Glu Thr Ser Arg Val Gln Leu Leu Trp Asn Thr Ala Asn Met Phe Thr
    130                 135                 140

His Pro Arg Tyr Val His Gly Ala Ala Thr Ser Cys Asn Ala Asp Val
145                 150                 155                 160

Tyr Ala Tyr Ala Ala Ala Lys Val Lys Lys Gly Leu Asp Ile Ala Lys
                165                 170                 175
```

Glu Leu Gly Ala Glu Asn Tyr Val Phe Trp Gly Gly Arg Glu Gly Tyr
            180                 185                 190

Glu Thr Leu Leu Asn Thr Asp Met Lys Leu Glu Leu Glu Asn Leu Ala
            195                 200             205

Ser Phe Tyr Arg Met Ala Val Glu Tyr Ala Arg Glu Ile Gly Phe Asp
210                 215                 220

Gly Gln Phe Leu Ile Glu Pro Lys Pro Lys Glu Pro Thr Lys His Gln
225                 230                 235                 240

Tyr Asp Phe Asp Ala Ala Thr Thr Ile Ala Phe Leu Glu Thr Tyr Gly
                245                 250                 255

Leu Lys Asp His Phe Lys Leu Asn Leu Glu Ala Asn His Ala Thr Leu
            260                 265                 270

Ala Gly His Thr Phe Glu His Glu Leu Arg Val Ala Ala Leu His Asp
        275                 280                 285

Met Leu Gly Ser Ile Asp Ala Asn Gln Gly Asp Leu Leu Leu Gly Trp
    290                 295                 300

Asp Thr Asp Glu Phe Pro Thr Asp Leu Tyr Ser Ala Val Leu Ala Met
305                 310                 315                 320

Tyr Glu Ile Leu Lys Ala Gly Gly Phe Lys Thr Gly Gly Ile Asn Phe
                325                 330                 335

Asp Ala Lys Val Arg Arg Pro Ser Phe Ala Asp Glu Asp Leu Phe His
            340                 345                 350

Ala His Ile Ala Gly Met Asp Thr Tyr Ala Val Gly Leu Lys Val Ala
        355                 360                 365

Ser Arg Leu Leu Glu Asp Lys Ala Leu Asp Gln Val Ile Glu Glu Arg
    370                 375                 380

Tyr Glu Ser Tyr Thr Lys Gly Ile Gly Leu Glu Ile Lys Glu Gly Arg
385                 390                 395                 400

Thr Asp Leu Lys Lys Leu Ala Ala Tyr Ala Leu Glu His Asp His Ile
                405                 410                 415

Glu Asn Gln Ser Gly Arg Gln Glu Arg Leu Lys Ala Thr Val Asn Arg
            420                 425                 430

Tyr Leu Leu Asn Ala Leu Arg Glu Ala Pro Arg Gly Lys Glu Thr Arg
        435                 440                 445

<210> SEQ ID NO 19
<211> LENGTH: 513
<212> TYPE: PRT
<213> ORGANISM: BACILLUS SPEC.

<400> SEQUENCE: 19

Met Thr Leu Glu Lys Phe Val Asp Ala Leu Pro Ile Pro Asp Thr Leu
1               5                   10                  15

Lys Pro Val Gln Gln Thr Thr Glu Lys Thr Tyr Tyr Glu Val Thr Met
            20                  25                  30

Glu Glu Cys Ala His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

```
Pro Asp Ser Asp Gly Tyr Pro Glu Ala Trp Phe Ser Lys Asp Phe Glu
            115                 120                 125

Gln Thr Gly Pro Tyr Phe Lys Arg Glu Val Tyr His Tyr Pro Asn Gln
        130                 135                 140

Gln Arg Gly Ala Thr Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Gly Pro Glu Asn Pro Ser Pro Ser Leu Pro Lys Pro Ser Ile
210                 215                 220

Val Pro Ala Phe Cys Gly Asp Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Ala Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
        290                 295                 300

Asp Phe Thr Ala Tyr Glu Gly Glu Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile Gln Asn
        355                 360                 365

Ile Arg Thr Leu Lys Leu Ala Gly Thr Gln Asp Glu Tyr Gly Arg Val
        370                 375                 380

Val Gln Leu Leu Asn Asn Lys Arg Trp His Asp Pro Val Thr Glu Ala
385                 390                 395                 400

Pro Lys Ala Gly Thr Thr Glu Ile Trp Ser Ile Val Asn Pro Thr Gln
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
        435                 440                 445

Tyr Thr Gly Pro Ala Val Pro Pro Pro Ser Glu Lys Gly Trp Lys
        450                 455                 460

Asp Thr Ile Gln Ala His Ala Gly Glu Val Leu Arg Ile Ala Val Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys
```

```
<210> SEQ ID NO 20
<211> LENGTH: 519
<212> TYPE: PRT
<213> ORGANISM: ESCHERICHIA COLI

<400> SEQUENCE: 20
```

| | | | | | | | | | | | | | | |
|---|---|---|---|---|---|---|---|---|---|---|---|---|---|---|
| Met | Gln | Arg | Arg | Asp | Phe | Leu | Lys | Tyr | Ser | Val | Ala | Leu | Gly | Val | Ala |
| 1 | | | | 5 | | | | | 10 | | | | | 15 | |
| Ser | Ala | Leu | Pro | Leu | Trp | Asn | Arg | Ala | Val | Phe | Ala | Ala | Glu | Arg | Pro |
| | | | 20 | | | | | 25 | | | | | 30 | | |
| Thr | Leu | Pro | Ile | Pro | Asp | Leu | Leu | Thr | Thr | Asp | Ala | Arg | Asn | Arg | Ile |
| | | | 35 | | | | | 40 | | | | | 45 | | |
| Gln | Leu | Thr | Ile | Gly | Ala | Gly | Gln | Ser | Thr | Phe | Gly | Gly | Lys | Thr | Ala |
| | 50 | | | | | 55 | | | | | 60 | | | | |
| Thr | Thr | Trp | Gly | Tyr | Asn | Gly | Asn | Leu | Leu | Gly | Pro | Ala | Val | Lys | Leu |
| 65 | | | | | 70 | | | | | 75 | | | | | 80 |
| Gln | Arg | Gly | Lys | Ala | Val | Thr | Val | Asp | Ile | Tyr | Asn | Gln | Leu | Thr | Glu |
| | | | | 85 | | | | | 90 | | | | | 95 | |
| Glu | Thr | Thr | Leu | His | Trp | His | Gly | Leu | Glu | Val | Pro | Gly | Glu | Val | Asp |
| | | | 100 | | | | | 105 | | | | | 110 | | |
| Gly | Gly | Pro | Gln | Gly | Ile | Ile | Pro | Pro | Gly | Gly | Lys | Arg | Ser | Val | Thr |
| | | | 115 | | | | | 120 | | | | | 125 | | |
| Leu | Asn | Val | Asp | Gln | Pro | Ala | Ala | Thr | Cys | Trp | Phe | His | Pro | His | Gln |
| | 130 | | | | | 135 | | | | | 140 | | | | |
| His | Gly | Lys | Thr | Gly | Arg | Gln | Val | Ala | Met | Gly | Leu | Ala | Gly | Leu | Val |
| 145 | | | | | 150 | | | | | 155 | | | | | 160 |
| Val | Ile | Glu | Asp | Asp | Glu | Ile | Leu | Lys | Leu | Met | Leu | Pro | Lys | Gln | Trp |
| | | | | 165 | | | | | 170 | | | | | 175 | |
| Gly | Ile | Asp | Asp | Val | Pro | Val | Ile | Val | Gln | Asp | Lys | Lys | Phe | Ser | Ala |
| | | | 180 | | | | | 185 | | | | | 190 | | |
| Asp | Gly | Gln | Ile | Asp | Tyr | Gln | Leu | Asp | Val | Met | Thr | Ala | Ala | Val | Gly |
| | | | 195 | | | | | 200 | | | | | 205 | | |
| Trp | Phe | Gly | Asp | Thr | Leu | Leu | Thr | Asn | Gly | Ala | Ile | Tyr | Pro | Gln | His |
| | 210 | | | | | 215 | | | | | 220 | | | | |
| Ala | Ala | Pro | Arg | Gly | Trp | Leu | Arg | Leu | Arg | Leu | Leu | Asn | Gly | Cys | Asn |
| 225 | | | | | 230 | | | | | 235 | | | | | 240 |
| Ala | Arg | Ser | Leu | Asn | Phe | Ala | Thr | Ser | Asp | Asn | Arg | Pro | Leu | Tyr | Val |
| | | | | 245 | | | | | 250 | | | | | 255 | |
| Ile | Ala | Ser | Asp | Gly | Gly | Leu | Leu | Pro | Glu | Pro | Val | Lys | Val | Ser | Glu |
| | | | 260 | | | | | 265 | | | | | 270 | | |
| Leu | Pro | Val | Leu | Met | Gly | Glu | Arg | Phe | Glu | Val | Leu | Val | Glu | Val | Asn |
| | | | 275 | | | | | 280 | | | | | 285 | | |
| Asp | Asn | Lys | Pro | Phe | Asp | Leu | Val | Thr | Leu | Pro | Val | Ser | Gln | Met | Gly |
| | 290 | | | | | 295 | | | | | 300 | | | | |
| Met | Ala | Ile | Ala | Pro | Phe | Asp | Lys | Pro | His | Pro | Val | Met | Arg | Ile | Gln |
| 305 | | | | | 310 | | | | | 315 | | | | | 320 |
| Pro | Ile | Ala | Ile | Ser | Ala | Ser | Gly | Ala | Leu | Pro | Asp | Thr | Leu | Ser | Ser |
| | | | | 325 | | | | | 330 | | | | | 335 | |
| Leu | Pro | Ala | Leu | Pro | Ser | Leu | Glu | Gly | Leu | Thr | Val | Arg | Lys | Leu | Gln |
| | | | 340 | | | | | 345 | | | | | 350 | | |
| Leu | Ser | Met | Asp | Pro | Met | Leu | Asp | Met | Met | Gly | Met | Gln | Met | Leu | Met |
| | | | 355 | | | | | 360 | | | | | 365 | | |
| Glu | Lys | Tyr | Gly | Asp | Gln | Ala | Met | Ala | Gly | Met | Asp | His | Ser | Gln | Met |
| | 370 | | | | | 375 | | | | | 380 | | | | |

```
Met Gly His Met Gly His Gly Asn Met Asn His Met Asn His Gly Gly
385                 390                 395                 400

Lys Phe Asp Phe His His Ala Asn Lys Ile Asn Gly Gln Ala Phe Asp
            405                 410                 415

Met Asn Lys Pro Met Phe Ala Ala Ala Lys Gly Gln Tyr Glu Arg Trp
            420                 425                 430

Val Ile Ser Gly Val Gly Asp Met Met Leu His Pro Phe His Ile His
            435                 440                 445

Gly Thr Gln Phe Arg Ile Leu Ser Glu Asn Gly Lys Pro Pro Ala Ala
            450                 455                 460

His Arg Ala Gly Trp Lys Asp Thr Val Lys Val Glu Gly Asn Val Ser
465                 470                 475                 480

Glu Val Leu Val Lys Phe Asn His Asp Ala Pro Lys Glu His Ala Tyr
            485                 490                 495

Met Ala His Cys His Leu Leu Glu His Glu Asp Thr Gly Met Met Leu
            500                 505                 510

Gly Phe Thr Val Ser Asp Pro
            515

<210> SEQ ID NO 21
<211> LENGTH: 417
<212> TYPE: PRT
<213> ORGANISM: Bacillus spec.

<400> SEQUENCE: 21

Met Lys Glu Leu Gly His Glu Val Leu Lys Pro Tyr Asp Gly Trp Ala
1               5                   10                  15

Ala Tyr Gly Glu Gly Thr Thr Gly Gly Ala Met Ala Ser Pro Gln Asn
            20                  25                  30

Val Phe Val Thr Asn Arg Thr Glu Leu Ile Gln Ala Leu Gly Gly
            35                  40                  45

Asn Asn His Thr Asn Gln Tyr Asn Ser Val Pro Lys Ile Ile Tyr Val
50                  55                  60

Lys Gly Thr Ile Asp Leu Asn Val Asp Asp Asn Gln Pro Val Gly
65                  70                  75                  80

Pro Asp Phe Tyr Lys Asp Pro His Phe Asp Phe Glu Ala Tyr Leu Arg
            85                  90                  95

Glu Tyr Asp Pro Ala Thr Trp Gly Lys Lys Glu Val Glu Gly Pro Leu
            100                 105                 110

Glu Glu Ala Arg Val Arg Ser Gln Lys Lys Gln Lys Asp Arg Ile Met
            115                 120                 125

Val Tyr Val Gly Ser Asn Thr Ser Ile Ile Gly Val Gly Lys Asp Ala
130                 135                 140

Lys Ile Lys Gly Gly Phe Leu Ile Lys Asn Val Asp Asn Val Ile
145                 150                 155                 160

Ile Arg Asn Ile Glu Phe Glu Ala Pro Leu Asp Tyr Phe Pro Glu Trp
            165                 170                 175

Asp Pro Thr Asp Gly Thr Leu Gly Glu Trp Asn Ser Glu Tyr Asp Ser
            180                 185                 190

Ile Ser Ile Glu Gly Ser Ser His Ile Trp Ile Asp His Asn Thr Phe
            195                 200                 205

Thr Asp Gly Asp His Pro Asp Arg Ser Leu Gly Thr Tyr Phe Gly Arg
            210                 215                 220

Pro Phe Gln Gln His Asp Gly Ala Leu Asp Ile Lys Asn Ser Ser Asp
225                 230                 235                 240
```

```
Phe Ile Thr Ile Ser Tyr Asn Val Phe Thr Asn His Asp Lys Val Thr
                245                 250                 255

Leu Ile Gly Ala Ser Asp Ser Arg Met Ala Asp Ser Gly His Leu Arg
            260                 265                 270

Val Thr Leu His His Asn Tyr Tyr Lys Asn Val Thr Gln Arg Leu Pro
        275                 280                 285

Arg Val Arg Phe Gly Gln Val His Ile Tyr Asn Asn Tyr Tyr Glu Phe
    290                 295                 300

Ser Asn Leu Ala Asp Tyr Asp Phe Gln Tyr Ala Trp Gly Val Gly Val
305                 310                 315                 320

Phe Ser Gln Ile Tyr Ala Gln Asn Asn Tyr Phe Ser Phe Asp Trp Asp
                325                 330                 335

Ile Asp Pro Ser Leu Ile Ile Lys Val Trp Ser Lys Asn Glu Glu Ser
            340                 345                 350

Met Tyr Glu Thr Gly Thr Ile Val Asp Leu Pro Asn Gly Arg Arg Tyr
        355                 360                 365

Ile Asp Leu Val Ala Ser Tyr Asn Glu Ser Asn Thr Leu Gln Leu Lys
    370                 375                 380

Lys Glu Val Thr Trp Lys Pro Met Phe Tyr His Val Ile His Pro Thr
385                 390                 395                 400

Pro Ser Val Pro Ala Leu Val Lys Ala Lys Ala Gly Ala Gly Asn Leu
                405                 410                 415

His

<210> SEQ ID NO 22
<211> LENGTH: 175
<212> TYPE: PRT
<213> ORGANISM: ESCHERICHIA COLI

<400> SEQUENCE: 22

Met Val Thr Phe His Thr Asn His Gly Asp Ile Val Ile Lys Thr Phe
1               5                   10                  15

Asp Asp Lys Ala Pro Glu Thr Val Lys Asn Phe Leu Asp Tyr Cys Arg
            20                  25                  30

Glu Gly Phe Tyr Asn Asn Thr Ile Phe His Arg Val Ile Asn Gly Phe
        35                  40                  45

Met Ile Gln Gly Gly Gly Phe Glu Pro Gly Met Lys Gln Lys Ala Thr
    50                  55                  60

Lys Glu Pro Ile Lys Asn Glu Ala Asn Gly Leu Lys Asn Thr Arg
65                  70                  75                  80

Gly Thr Leu Ala Met Ala Arg Thr Gln Ala Pro His Ser Ala Thr Ala
            85                  90                  95

Gln Phe Phe Ile Asn Val Val Asp Asn Asp Phe Leu Asn Phe Ser Gly
        100                 105                 110

Glu Ser Leu Gln Gly Trp Gly Tyr Cys Val Phe Ala Glu Val Val Asp
    115                 120                 125

Gly Met Asp Val Val Asp Lys Ile Lys Gly Val Ala Thr Gly Arg Ser
130                 135                 140

Gly Met His Gln Asp Val Pro Lys Glu Asp Val Ile Ile Glu Ser Val
            145                 150                 155                 160

Thr Val Ser Glu Gly Thr Ser Glu Asn Leu Tyr Phe Gln Gly Ala
                165                 170                 175

<210> SEQ ID NO 23
```

```
<211> LENGTH: 1335
<212> TYPE: DNA
<213> ORGANISM: THERMOTOGA NEAPOLITANA

<400> SEQUENCE: 23
atggccgaat tttttcctga gattccgaaa attcagttcg aaggtaaaga aagcaccaat        60
ccgctggcat ttcgttttta tgatccgaac gaagtgattg atggtaaacc gctgaaagat      120
cacctgaaat ttagcgttgc attttggcat acctttgtga atgaaggtcg tgatccgttt      180
ggtgatccga ccgcagaacg tccgtggaat cgttttagcg atccgatgga taaagcattt      240
gcacgtgttg atgcactgtt tgaattttgc gaaaaactga acatcgagta tttctgcttt      300
cacgatcgcg atattgcacc ggaaggtaaa accctgcgtg aaaccaacaa aattctggat      360
aaagtggtgg aacgcatcaa agaacgtatg aaagatagca atgttaaact gctgtggggc      420
accgcaaacc tgtttagcca tccgcgttat atgcatggtg cagcaaccac ctgtagcgca      480
gatgttttg cctatgcagc agcacaggtt aaaaaagcac tggaaatcac caaagaactg       540
ggtggtgaag ttatgttttt tggggtggt cgtgaaggct atgaaacact gctgaatacc       600
gatctgggtc tggaactgga aaatctggca cgttttctgc gtatggcagt tgaatatgcg      660
aaaaaaatcg ttttaccgg tcagtttctg attgaaccga accgaaaga accgaccaaa        720
caccagtatg attttgatgt tgcaaccgcc tatgcctttc tgaaaaatca tggtctggat      780
gagtacttca aattcaacat tgaagcaaat catgcaaccc tggcaggtca tacctttcag      840
catgaactgc gcatggcacg cattctgggt aaactgggta gcattgatgc caatcagggt      900
gatctgctgc tgggttggga tacagatcag tttccgacca catttatga taccaccctg       960
gcaatgtatg aagtgattaa agccggtggt tttaccaaag gtggtctgaa ttttgatgca     1020
aaagttcgtc gtgccagcta taagttgag gacctgttta ttggtcatat cgcaggtatg      1080
gataccttg cactgggctt taaaatcgca tataaactgg caaagatgg cgtgttcgat       1140
aaattcatcg aggaaaaata tcgcagcttc aaagaaggca ttggcaaaga aattgttgag     1200
ggcaaaaccg actttgagaa actggaagaa tacatcatcg acaaagaaga tattgaactg     1260
ccgagcggca acaagaata tctggaaagc ctgctgaaca gctatatcgt taaaaccatt      1320
gcagaactgc gctaa                                                      1335

<210> SEQ ID NO 24
<211> LENGTH: 1167
<212> TYPE: DNA
<213> ORGANISM: STREPTOMYCES MURINUS

<400> SEQUENCE: 24
atgagctttc agccgacccc ggaagatcgc tttacctttg gcctgtggac cgtgggctgg       60
cagggccgcg atccgtttgg cgatgcgacc cgcccggcgc tggatccggt ggaaaccgtg      120
cagcgcctgg cggaactggg cgcgtatggc gtgaccttc atgatgatga tctgattccg       180
tttggcagca gcgataccga acgcgaaagc catattaaac gctttcgcca ggcgctggat      240
gcgaccggca tgaccgtgcc gatggcgacc accaacctgt ttacccatcc ggtgttaaa       300
gatgcgggct ttaccgcgaa cgatcgcgat gtgcgccgct atgcgctgcg caaaaccatt      360
ggcaacattg atctggcggc ggaactgggc gcgaaaacct atgtggcgtg ggcggccgc       420
gaaggcgcgg aaagcggcgg cgcgaaagat gtgcgcgatg cgctggatcg catgaaagaa      480
gcgtttgatc tgctgggcga atatgtgacc gcgcagggct atgatctgcg ctttgcgatt      540
gaaccgaaac cgaacgaacc gcgcggcgat attctgctgc cgaccgtggg ccatgcgctg      600
```

```
gcgtttattg aacgcctgga acgcccggaa ctgtatggcg tgaacccgga agtgggccat      660
gaacagatgg cgggcctgaa ctttccgcat ggcattgcgc aggcgctgtg ggcgggcaaa      720
ctgtttcata ttgatctgaa cggccagagc ggcattaaat atgatcagga tctgcgcttt      780
ggcgcgggcg atctgcgcgc ggcgttttgg ctggtggatc tgctggaaac cgcgggctat      840
gaaggcccgc gccatttga ttttaaaccg ccgcgcaccg aagattttga tggcgtgtgg      900
gcgagcgcgg cgggctgcat gcgcaactat ctgattctga agatcgcgc ggcggcgttt      960 cgcgcggatc cggaagtgca ggaagcgctg cgcgcggcgc gcctggatca gctggcgcag     1020
ccgaccgcgg cggatggcct ggatgcgctg ctggcggatc gcgcggcgtt tgaagatttt     1080
gatgtggatg cggcggcggc gcgcggcatg gcgtttgaac atctggatca gctggcgatg     1140
gatcatctgc tgggcgcgcg cggctaa                                        1167
```

<210> SEQ ID NO 25
<211> LENGTH: 1320
<212> TYPE: DNA
<213> ORGANISM: THERMOANAEROBACTERIUM THERMOSULFURIGENES

<400> SEQUENCE: 25

```
atgaacaaat attttgaaaa cgtgagcaaa attaaatatg aaggcccgaa agcaacaac       60 ccgtatagct ttaaatttta tacccggaa gaagtgattg atggcaaaac catgaagaa      120 catctgcgct ttagcattgc gtattggcat acctttaccg cggatggcac cgatcagttt     180
ggcaaagcga ccatgcagcg cccgtggaac cattataccg atccgatgga tattgcgaaa     240
gcgcgcgtgg aagcggcgtt tgaatttttt gataaaatta cgcgccgta ttttttgcttt     300 catgatcgcg atattgcgcc ggaaggcgat accctgcgcg aaaccaacaa aaacctggat     360
accattgtgg cgatgattaa agattatctg aaaaccagca aaaccaaagt gctgtggggc     420
accgcgaacc tgtttagcaa cccgcgcttt gtgcatggcg cgagcaccag ctgcaacgcg     480
gatgtgtttg cgtatagcgc ggcgcaggtg aaaaaagcgc tggaaattac caaagaactg     540
ggcggcgaaa actatgtgtt tggggcggc cgcgaaggct atgaaaccct gctgaacacc     600
gatatggaat ttgaactgga taactttgcg cgctttctgc atatggcggt ggattatgcg     660
aaagaaattg cttttgaagg ccagtttctg attgaaccga acccgaaaga accgaccaaa     720
catcagtatg attttgatgt ggcgaacgtg ctggcgtttc tgcgcaaata tgatctggat     780
aaatatttta agtgaacat tgaagcgaac catgcgaccc tggcgtttca tgattttcag     840
catgaactgc gctatgcgcg cattaacggc gtgctgggca gcattgatgc gaacaccggc     900
gatatgctgc tgggctggga taccgatcag tttccgaccg atattcgcat gaccaccctg     960
gcgatgtatg aagtgattaa atgggcggc tttgataaag cggcctgaa ctttgatgcg    1020 aaagtgcgcc gcgcgagctt tgaaccggaa gatctgtttc tgggccatat gcgggcatg    1080 gatgcgtttg cgaaaggctt taagtggcg tataaactgg tgaaagatcg cgtgtttgat    1140
aaatttattg aagaacgcta tgcgagctat aaagatggca ttggcgcgga tattgtgagc    1200
ggcaaagcgg attttcgcag cctgaaaaaa tatgcgctgg aacgcagcca gattgtgaac    1260
aaaagcggcc gccaggaact gctggaaagc attctgaacc agtatctgtt tgcggaataa    1320
```

<210> SEQ ID NO 26
<211> LENGTH: 1107
<212> TYPE: DNA
<213> ORGANISM: DICTYOGLOMUS THERMOPHILUM

<400> SEQUENCE: 26

```
atgccgtttg ttgatcatcg tgcacagaaa attcgtcgca gcaaagaaga actgctgaaa      60
catatgcaga ccttcaaact ggatctgaaa tttagcgtgg catctggta ttttacaccg      120
ggtggtggtc gttttcatga accgtatgtt gaacagaaaa gcattccgga acgtattgaa     180
atggcagcag aaatggcaaa atttggcgtg aaaggtattg aagcacatta tccggctgaa     240
gtgaatgaag aaaatctgca cctgtataaa cagctggaaa aagaagcagg tattcgtctg     300
gttgcagttc cgctgagcct gttttatgat aaaatctttg aatttggcag cctgagcaac     360
ccgtatgaaa aatatcgtaa agttgcctat gaacgcctgg tgaatggtct gaaactggtt     420
aaagaagcaa acgccgatat ttgcattatt tggcctggta ttgatggcta tacctatagc     480
tatggtcacc tgtattatca catgtgggat accttttgaag aactggttgc acaggcaatg   540
gatgaagttc cgggtgttca ggttgcaatt gaaccgaaac cgtatgaacc ggcaccgaat     600
aacatttatc gtaccaccgc agatggtatt ctggcagcac gtgatattga agcgcgtctg     660
aaaaatccgg aaacctgaa actgctgcaa gaaggtcacg cactggttgg tctgaatccg      720
gaagttggtc atgttcgtat gggttttgaa gatctgccgt atgcatatgc ccgtgttgca    780
cgtgaaggtc gtctgtttca tacccattgg aatagccagc cgctgggtaa ttatgatcag    840
gatctgaata ttggtgtggt ggattgggat agcaccgaag cactgctgta taccctgaaa    900
atggttggtt atcagggcta ttttggcatc gatatcaatc cggaacgcat gccggttatt    960
aaagccattg aaattaacac caaagtgctg cagattatga cgaacgcat tgaacgtctg    1020
ccgcatgatc gtattattga tgttattttt gaccctgaga atcatcgtgg tgaactggaa   1080
ctgattctgg ccgaaaatca taaataa                                        1107
```

<210> SEQ ID NO 27
<211> LENGTH: 1158
<212> TYPE: DNA
<213> ORGANISM: MARINACTINOSPORA THERMOTOLERANS

<400> SEQUENCE: 27

```
atgagcagct atcgtccgga accggaagat aaattcagct ttggtctgtg gaccgttggt      60
tggcgtggtg ttaataccct tggtgatgca gttcgtccgc ctctggaccc tgcagaagca    120
gttcatcgtc tggcaggtct gggtgcatat ggtattaccct tcatgatga tgatctgatt    180
ccgcctggta gcagcgcagc agaacgtgat gcaattctgg gtcgttttcg taaagcactg    240
gatgaaaccg gtctgaccgt tccgatggca accgttaacc tgtttagcca tccggttttt    300
cgtgatggtg gttttaccag caatagccgt gcaacccgtc gttatgcaat cgcaaaagca    360
gttcgtgcaa ttgatctggc agccgaactg ggtgcacgta cctttgtttg ttggggtggt   420
caggatggtg cagaaaccga agcaggtaaa gatgatcgtg cagcactgga acgtctgcgt    480
gaagcattta tctgatgtg tggttatgtt cgtgaacagg ttatgatct gcgttttgca     540
gttgaaccga accgaatga accgcgtggt gatgtgctgc tgccgaccgt gggtcatgca    600
ctggcattta ttggtgaact ggaacatccg gaaatggttg gtgtgaatcc ggaagttggt    660
catgagcaga tggcaggcct gaattttgca catggtgttg cacaggcact gtggcatggt    720
aaactgttc atattgatct gaatggtcag cgtggcgtga aatatgatca ggatctgcgc    780
tttggtgccg gtgatgttaa agaagcattt tttctggttg atctgctgga acgtagcggt    840
tatgatggtc cgcgtcattt tgattttaaa ccgcctcgta ccgaagatgt tgatggtgtt    900
tgggaaagcg cagccgcatg tatgcgtaat tatctgattc tgaaagaaaa agccgcagca    960
```

```
tttcgtgccg atcctgaagt tgcagatgcc ctggcagcaa gccgtgttgc agaactgagc    1020
gaaccgaccc tgggcaccgg tgaaagcctg cagacctgc tggcggaaga ttttgatgtg    1080
gatgcagccg gtgaacgtgg ttatcatttt gaacgtctgg atcagctggc aatggatcac    1140
ctgtttggtg ttcgttaa                                                 1158

<210> SEQ ID NO 28
<211> LENGTH: 1326
<212> TYPE: DNA
<213> ORGANISM: BACILLUS STEAROTHERMOPHILUS

<400> SEQUENCE: 28
atgccgtatt ttgataacat tagcaccatt gcgtatgaag gcccggcgag caaaaacccg     60
ctggcgttta aattttataa cccggaagaa aaagtgggcg ataaaaccat ggaagaacat    120
ctgcgcttta gcgtggcgta ttggcatacc tttaccggcg atggcagcga tccgtttggc    180
gcgggcaaca tgattcgccc gtggaacaaa tatagcggca tggatctggc gaaagcgcgc    240
gtggaagcgg cgtttgaatt ttttgaaaaa ctgaacattc cgttttttg ctttcatgat    300 gtggatattg cgccggaagg cgaaaccctg aaagaaacct ataaaaacct ggatattatt    360
gtggatatga ttgaagaata tgaaaaacc agcaaaacca aactgctgtg aacaccgcg     420 aacctgttta cccatccgcg ctttgtgcat ggcgcggcga ccagctgcaa cgcggatgtg    480
tttgcgtatg cggcggcgaa agtgaaaaaa ggcctggaaa ttgcgaaacg cctgggcgcg    540
gaaaactatg tgtttggggg cggccgcgaa ggctatgaaa ccctgctgaa caccgatatg    600
aaactggaac tggataacct ggcgcgcttt ctgcatatgg cggtggatta tgcgaaagaa    660
attggctttg atggccagtt tctgattgaa ccgaaaccga agaaccgac caaacatcag    720 tatgattttg atgtggcgac cgcgctggcg tttctgcaga cctatggcct gaaagattat    780
tttaaattta acattgaagc gaaccatgcg accctggcgg ccataccttt gaacatgaa    840 ctgcgcgtgg cgcgcattca tggcatgctg ggcagcgtgg atgcgaacca gggcgatatg    900
ctgctgggct gggataccga tgaatttccg accgatctgt atagcaccac cctggcgatg    960
tatgaaattc tgaaaacgg cggcctgggc cgcggcggcc tgaactttga tgcgaaagtg    1020
cgccgcggca gctttgaacc ggaagatctg ttttatgcgc atattgcggg catggatagc    1080
tttgcggtgg gcctgaaagt ggcgcatcgc ctgattgaag atcgcgtgtt tgatgaattt    1140
attgaagaac gctataaaag ctataccgaa ggcattggcc gcgaaattgt ggaaggcacc    1200
gcggattttc ataaactgga agcgcatgcg ctgcagctgg cgaaattca gaaccagagc    1260 ggccgccagg aacgcctgaa aaccctgctg aaccagtatc tgctggaagt gtgcgcggcg    1320
cgctaa                                                              1326

<210> SEQ ID NO 29
<211> LENGTH: 1164
<212> TYPE: DNA
<213> ORGANISM: THERMUS THERMOPHILUS

<400> SEQUENCE: 29
atgtatgaac cgaaaccgga acatcgcttt accttttggcc tgtggaccgt gggcaacgtg     60
ggccgcgatc cgtttggcga tgcggtgcgc gaacgcctgg atccggtgta tgtggtgcat    120
aaactggcgg aactgggcgc gtatggcgtg aacctgcatg atgaagatct gattccgcgc    180
ggcaccccgc cgcaggaacg cgatcagatt gtgcgccgct taaaaaagc gctggatgaa    240
```

```
accggcctga aagtgccgat ggtgaccgcg aacctgttta gcgatccggc gtttaaagat      300
ggcgcgttta ccagcccgga tccgtgggtg cgcgcgtatg cgctgcgcaa aagcctggaa      360
accatggatc tgggcgcgga actgggcgcg gaaatttatg tggtgtggcc gggccgcgaa      420
ggcgcggaag tggaagcgac cggcaaagcg cgcaaagtgt gggattgggt gcgcgaagcg      480
ctgaacttta tggcggcgta tgcggaagat cagggctatg gctatcgctt tgcgctggaa      540
ccgaaaccga acgaaccgcg cggcgatatt tattttgcga ccgtgggcag catgctggcg      600
tttattcata ccctggatcg cccggaacgc tttggcctga cccggaatt tgcgcatgaa       660 accatggcgg gcctgaactt tgtgcatgcg gtggcgcagg cgctggatgc gggcaaactg      720
tttcatattg atctgaacga tcagcgcatg agccgctttg atcaggatct gcgctttggc      780
agcgaaaacc tgaaagcggc gttttttctg gtggatctgc tggaaagcag cggctatcag      840
ggcccgcgcc attttgatgc gcatgcgctg cgcaccgaag atgaagaagg cgtgtgggcg      900
tttgcgcgcg gctgcatgcg cacctatctg attctgaaag aacgcgcgga agcgtttcgc      960
gaagatccgg aagtgaaaga actgctggcg gcgtattatc aggaagatcc ggcggcgctg     1020
gcgctgctgg gcccgtatag ccgcgaaaaa gcggaagcgc tgaaacgcgc ggaactgccg     1080
ctggaagcga aacgccgccg cggctatgcg ctggaacgcc tggatcagct ggcggtggaa     1140
tatctgctgg gcgtgcgcgg ctaa                                            1164

<210> SEQ ID NO 30
<211> LENGTH: 1164
<212> TYPE: DNA
<213> ORGANISM: THERMUS CALDOPHILUS

<400> SEQUENCE: 30
atgtatgaac cgaaaccgga acatcgcttt acctttggcc tgtggaccgt gggcaacgtg       60
ggccgcgatc cgtttggcga tgcggtgcgc gaacgcctgg atccggtgta tgtgggccat      120
aaactggcgg aactgggcgt gcatggcgtg aacctgcatg atgaagatct gattccgcgc      180
ggcaccccgc cgcaggaacg cgatcagatt gtgcgccgct taaacgcgc gctggatgaa       240 accggcctga aagtgccgat ggtgaccggc aacctgttta gcgatccggg ctttaaagat      300
ggcggcttta ccagccgcga tccgtgggtg cgcgcgtatg cgtttcgcaa aagcctggaa      360
accatggatc tgggcgcgga actgggcgcg gaaatttatg tggtgtggcc gggccgcgaa      420
ggcgcggaag tggaagcgac cggcaaagcg cgcaaagtgt gggattgggt gcgcgaaccg      480 ctgaactttta tggcggcgta tgcggaagat cagggctatg gctatcgctt tgcgctggaa     540
ccgaaaccga acgaaccgcg cggcgatatt tattttgcga ccgtgggcag catgctggcg      600
ctgattcata ccctggaacg cccggaacgc tttggcctga cccggaatt tgcgcatgaa       660 accatggcgg gcctgaactt tgtgcatgcg gtggcgcagg cgctggatgc gggcaaactg      720
ctgcatattg atctgaacgg ccagcgcatg aaccgctttg atcaggatct gcgctttggc      780
agcgaaaacc tgaaagcggc gtttctgctg gtggatctgc tggaaagcag cggctatcag      840
ggcccgcgcc attttgatgc gcatgcgctg cgcaccgaag atgaagaagg cgtgtgggcg      900
tttgcgcgcg gctgcatgcg cacctatctg attctgaaag aacgcgcgga agcgtttcgc      960
gaagatccgg aagtgaaaga actgctggcg gcgtattatc aggaagatcc ggcggcgctg     1020
ccgctgatga tccgtatag ccatgaaaaa gcggaagcgc tgaaacgcgc ggaactgccg      1080
ctggaagcga aacgccatcg cggctatgcg ctggaacgcc tggatcagct ggcggtggaa     1140
tatctgctgg gcgtgcgcgg ctaa                                            1164
```

<210> SEQ ID NO 31
<211> LENGTH: 1164
<212> TYPE: DNA
<213> ORGANISM: STREPTOMYCES OLIVOCHROMOGENES

<400> SEQUENCE: 31

```
atgagctatc agccgacccc ggaagatcgc tttacctttg gcctgtggac cgtgggctgg     60
cagggccgcg atccgtttgg cgatgcgacc cgcccggcgc tggatccggt ggaaaccgtg    120
cagcgcctgg cggaactggg cgcgcatggc gtgacctttc atgatgatga tctgattccg    180
tttggcagca gcgataccga acgcgaaagc catattaaac gctttcgcca ggcgctggat    240
gcgaccggca tgaccgtgcc gatggcgacc accaacctgt ttacccatcc ggtgtttaaa    300
gatgcgggct ttaccgcgaa cgatcgcgat gtgcgccgct atgcgctgcg caaaaccatt    360
cgcaacattg atctggcggt ggaactgggc gcgaaaacct atgtggcgtg ggcggccgc    420
gaaggcgcga aagcggcgc ggcgaaagat gtgcgcgtgg cgctggatcg catgaaagaa    480
gcgtttgatc tgctgggcga atatgtgacc agccagggct atgatattcg ctttgcgatt    540
gaaccgaaac cgaacgaacc gcgcggcgat attctgctgc cgaccgtggg ccatgcgctg    600
gcgtttattg aacgcctgga acgcccggaa ctgtatggcg tgaacccgga agtgggccat    660
gaacagatgg cgggcctgaa cttttccgcat ggcattgcgc aggcgctgtg ggcgggcaaa    720
ctgtttcata ttgatctgaa cggccagagc ggcattaaat atgatcagga tctgcgcttt    780
ggcgcgggcg atctgcgcgc ggcgttttgg ctggtggatc tgctggaaag cgcgggctat    840
gaaggcccgc gccattttga ttttaaaccg ccgcgcaccg aagatattga tggcgtgtgg    900
gcgagcgcgg cgggctgcat gcgcaactat ctgattctga agaacgcgc ggcggcgttt    960
cgcgcggatc cggaagtgca ggaagcgctg cgcgcgagcc gcctggatga actggcgcag   1020
ccgaccgcgg cggatggcgt gcaggaactg ctggcggatc gcaccgcgtt tgaagatttt   1080
gatgtggatg cggcggcggc gcgcggcatg cgtttgaac gcctggatca gctggcgatg   1140
gatcatctgc tgggcgcgcg ctaa                                          1164
```

<210> SEQ ID NO 32
<211> LENGTH: 1326
<212> TYPE: DNA
<213> ORGANISM: ANOXYBACILLUS GONENSIS

<400> SEQUENCE: 32

```
atggcctatt ttgagaacgt ggataaagtg gtttatgaag gtccggcaag cgaaaatccg     60
ctggccttta aattctataa cccggaagaa aaagtgggcg acaaaacaat ggaagaacat    120
ctgcgtttta gcgttgcata ttggcatacc tttgttggtg atggtgcaga tccgtttggt    180
gttggcaccg caattcgtcc gtggaatcgt tatagcggta tggatctggc aaaagcacgt    240
gttgaagcag catttgaact gttcgataaa ctgaacatcc gtttttttg cttccacgat    300
gttgatattg caccggaagg tgcaaccctg aaagaaacct atcagaatct ggataccatc    360
gtggatatga tcaagagta tatgaaaacc agcaaaacca aactgctgtg gaataccgca    420
aacctgttta cccatccgcg ttttgttcat ggtgcagcaa ccagctgtaa tgcagatgtt    480
tttgcctatg cagcagccaa agttaaaaaa ggtctggaaa ttgcaaaacg tctgggtgcc    540
gaaaactatg ttttttgggg tggtcgtgaa ggttatgaaa ccctgctgaa taccaatatg    600
aaactggaac tggataatct ggcacgtttt ctgcacatgg cagttgatta tgcaaaagaa    660
```

```
attggtttcg atggccagtt tctgattgaa ccgaaaccga agaaccgac caaacaccag    720
tatgattttg atgttgcaac cgcactggca tttctgcaga cctatggtct gaaagattac    780
ttcaaattta acatcgaagc caaccatgcc accctggcag gtcatacatt tgaacatgaa    840
ctgcgtgttg cacgtattca tggtatgctg ggtagcgttg atgcaaatca gggtgatccg    900
ctgctgggtt gggataccga tgaatttccg accgatctgt atagcaccac actggcaatg    960
tatgaaattc tgcaaaatgg tggtctgggt aaaggtggtc tgaattttga tgccaaagtt   1020
cgtcgtggta gctttgaacc tgaggacctg tttatgcac atattgcagg tatggatagc   1080
tttgcaattg gcctgaaagt tgcatatcgc ctgattgaag atcgtgtttt tgaaagcgtt   1140
gtggaagaac gctataaaag ctataccgaa ggtattggtc gcgatattat tgatggtaaa   1200
gccgattttc ataccctgga agcctatgca ctgaatctgc gtgatatttc aaatcgtagc   1260
ggtcgtcaag aacgtctgaa aacactgctg aaccagtatc tgctggaagt ttgtgttgcc   1320
cgttaa                                                               1326

<210> SEQ ID NO 33
<211> LENGTH: 1188
<212> TYPE: DNA
<213> ORGANISM: ARTHROBACTER NRRL B3728

<400> SEQUENCE: 33
atgagcgtgc agccgacccc ggcggatcat tttacctttg gcctgtggac cgtgggctgg    60
accggcgcgg atccgtttgg cgtggcgacc cgcaaaaacc tggatccggt ggaagcggtg   120
cataaactgg cggaactggg cgcgtatggc attacctttc atgataacga tctgattccg   180
tttgatgcga ccgaagcgga acgcgaaaaa attctgggcg attttaacca ggcgctgaaa   240
gataccggcc tgaaagtgcc gatggtgacc accaacctgt ttagccatcc ggtgtttaaa   300
gatggcggct ttaccagcaa cgatcgcagc attcgccgct ttgcgctggc gaaagtgctg   360
cataacattg atctggcggc ggaaatgggc gcggaaacct ttgtgatgtg ggcggccgc   420
gaaggcagcg aatatgatgg cagcaaagat ctggcggcgg cgctggatcg catgcgcgaa   480
ggcgtggata ccgcggcggg ctatattaaa gataaaggct ataacctgcg cattgcgctg   540
gaaccgaaac cgaacgaacc gcgcggcgat atttttctgc cgaccgtggg ccatggcctg   600
gcgtttattg aacagctgga acatggcgat attgtgggcc tgaacccgga aaccggccat   660
gaacagatgg cgggcctgaa ctttacccat ggcattgcgc aggcgctgtg gcggaaaaa   720
ctgtttcata ttgatctgaa cggccagcgc ggcattaaat atgatcagga tctggtgttt   780
ggccatggcg atctgaccag cgcgtttttt accgtggatc tgctggaaaa cggctttccg   840
aacggcggcc cgaaatatac cggcccgcgc catttgattt ataaaccgag ccgcaccgat   900
ggctatgatg gcgtgtggga tagcgcgaaa gcgaacatga gcatgtatct gctgctgaaa   960
gaacgcgcgc tggcgtttcg cgcggatccg gaagtgcagg aagcgatgaa aaccagcggc  1020
gtgtttgaac tggcgaaaac caccctgaac gcgggcgaaa gcgcggcgga tctgatgaac  1080
gatagcgcga gctttgcggg ctttgatgcg gaagcggcgg cggaacgcaa ctttgcgttt  1140
attcgcctga ccagctggc gattgaacat ctgctgggca gccgctaa               1188

<210> SEQ ID NO 34
<211> LENGTH: 1320
<212> TYPE: DNA
<213> ORGANISM: HALOTHERMOTHRIX ORENII

<400> SEQUENCE: 34
```

```
atggaagtgt ttaaaaacgt tccgcagacc atcaaatatg agggtaaaga tagcgataat      60
ccgctggcct ttaaatacta taacccggaa gaaaaagtgg gtggcaaaac aatggaagaa     120
catctgcgtt ttagcgttgc atattggcat accctgaccg tgatggtag cgatccgttt     180 ggtatgggca ccatgctgcg tccgtgggat accgcaaccg atccgatgga actggcaaaa     240
gcacgtgttc gtgcagcatt tgaattcatg agcaaactgg gtgtgaaata cttttgcttt     300
catgatcgtg atattgcacc ggaaggtcgt accctggcag aaaccaataa aaacctggat     360
gaaattgtga gcctgatcaa agaactgatg gatgaaaccg gtattaaact gctgtggggc     420
accgcaaacc tgtttagcaa tccgcgtttt gttcatggtg cagcaaccag cccgaatgca     480 gatgttttg catatgccgc agcacaggtt aaaaaagcaa tggaaatcac aaaagaactg     540
ggtggcgaaa actatgtttt tggggtggt cgtgaaggtt atgaaaccct gctgaatacc     600
gatatggaac tggaacaaga aaactttgca cgctttctgc atatggcagt tgattatgca     660
cgtgaaattg gttttgaagg ccagtttctg attgaaccga accgaaaga accgaccaaa     720 caccagtatg attttgatgc agccaccgtt attagctttc tgaaaaaata cgatctggac     780
aaacacttca aactgaacat tgaagcaaat catgcaacac tggcaggtca tacctttcag     840
catgaactgc atgttagccg tattaatggt atgctgggta gcgttgatgc aaatcagggt     900
gatctgctgc tgggttggga tacagatcag tttccgacca atatctatga accaccctg     960 gccatgtatg agatcctgaa aaatggtggt ctggaaccgg tggtctgaa ctttgatgcc    1020 aaagttcgtc gtgccagctt tgaaccggtt gacctgtttt atgcacatat tgcaggtatg    1080
gatgcatttg cacgcggtct gaaagttgca cacaaactgc tggaaagcgg tgaactggaa    1140
gattttatca gcgaacgcta taaaagctat cgcaatggta ttggcgagaa aattgttaaa    1200
ggtgaggtgg gctttaaaga gctggaagac tacgcactga ataacggcaa aatcaccaat    1260
gttagcggtc gtcaagagct gctggaatca attgtgaaca atatatcat cgaagcctaa    1320
```

<210> SEQ ID NO 35
<211> LENGTH: 1338
<212> TYPE: DNA
<213> ORGANISM: BACILLUS COAGULANS

<400> SEQUENCE: 35

```
atgatggcgt attttccgaa cgtgagcaaa attacctata gcggcaaaca gctgaaaagc      60
ggcctgagct ttaaccatta taacccgaaa gaactggtgg gcggcaaaac catggaagaa     120
cagctgcgct ttagcgtggc gttttggcat accttaccg aaagcggcac cgatccgttt     180
ggcgcgggca gcaaaattcg cccgtgggat cgctttaccg gcatggatct ggcgaaagcg     240
cgcgtggaag cggcgtttga ttttttgaa aaactgggca cccgtatttt ttgctttcat     300
gatcgcgata ttgcgccgga aggcgatacc ctgcgcgaaa ccaacaaaaa cctggatgtg     360
attgtggcga tgattaaaga ttatatgaaa ccagcaaag tgaaactgct gtggaacacc     420
gcgaacatgt ttaccaaccc gcgctttgtg catggcgcgg cgagcagctg caacgcggat     480
gtgtttgcgt atgcggcggc gcaggtgaaa aaaggcctgg aagtgggcaa agaactgggc     540
gcggaaaact atgtgttttg gggcggccgc gaaggctatg aaaccctgct gaacaccgat     600
ctgaaactgg aacaggataa cctggcgcgc tttttcata tggcggtgga ttatgcgaaa     660
gaaattggct ttgatgcgca gtttctgctg gaaccgaaac cgaaagaacc gaccaaacat     720
cagtatgatt ttgatgcggc gaccaccatt gcgtttctga aacctatga tctggatcag     780
```

| | |
|---|---|
| cattttaaac tgaacctgga agcgaaccat gcgaccctgg cgggccatac ctttgaacat | 840 |
| gaaattcgcg tggcgcgcac ccatggcctg ctgggcagcc tggatgcgaa ccagggcgat | 900 |
| ccgctgctgg gctgggatac cgatgaattt ccgaccgatc tgtatagcac caccctggcg | 960 |
| atgtatgaag tgctgaaaaa cggcggcctg gccgcggcg gcctgaactt tgatgcgaaa | 1020 |
| acccgccgcg cgagctttac cgatgaagat ctgttttatg cgcatattgc gggcatggat | 1080 |
| agctttgcgc tggcctgaa agtggcgaac cgcctgattg aagatcgcgt gtttgatgcg | 1140 |
| tttattgaag aacgctatag cagctataaa gaaggcattg gcgcggatat tgtgagcggc | 1200 |
| aaagcggatt ttaaaagcct ggaaaactat attctggata aaaagaaat tattaaccag | 1260 |
| agcggccgcc tggaacagct gaaaaacacc ctgaaccatt atattgtgca ggaagcgtat | 1320 |
| cagagcgtga acgcgtaa | 1338 |

<210> SEQ ID NO 36
<211> LENGTH: 1167
<212> TYPE: DNA
<213> ORGANISM: STREPTOMYCES RUBIGINOSUS

<400> SEQUENCE: 36

| | |
|---|---|
| atgaactatc agccgacccc ggaagatcgc tttacctttg gcctgtggac cgtgggctgg | 60 |
| cagggccgcg atccgtttgg cgatgcgacc cgccgcgcgc tggatccggt ggaaagcgtg | 120 |
| cgccgcctgg cggaactggg cgcgcatggc gtgaccttc atgatgatga tctgattccg | 180 |
| tttggcagca gcgatagcga acgcgaagaa catgtgaaac gctttcgcca ggcgctggat | 240 |
| gataccggca tgaaagtgcc gatggcgacc accaacctgt ttacccatcc ggtgttaaa | 300 |
| gatggcggct ttaccgcgaa cgatcgcgat gtgcgccgct atgcgctgcg caaaaccatt | 360 |
| cgcaacattg atctggcggt ggaactgggc gcggaaacct atgtggcgtg gggcggccgc | 420 |
| gaaggcgcgg aaagcggcgg cgcgaaagat gtgcgcgatg cgctggatcg catgaaagaa | 480 |
| gcgtttgatc tgctgggcga atatgtgacc agccagggct atgatattcg ctttgcgatt | 540 |
| gaaccgaaac cgaacgaacc gcgcggcgat attctgctgc cgaccgtggg ccatgcgctg | 600 |
| gcgtttattg aacgcctgga acgcccggaa ctgtatggcg tgaacccgga agtgggccat | 660 |
| gaacagatgg cgggcctgaa cttccgcat ggcattgcgc aggcgctgtg ggcgggcaaa | 720 |
| ctgtttcata ttgatctgaa cggccagaac ggcattaaat atgatcagga tctgcgcttt | 780 |
| ggcgcgggcg atctgcgcgc ggcgttttgg ctggtggatc tgctggaaag cgcgggctat | 840 |
| agcgcccgc gccattttga tttaaaccg ccgcgcaccg aagattttga tggcgtgtgg | 900 |
| gcgagcgcgg cgggctgcat gcgcaactat ctgattctga agaacgcgc ggcggcgttt | 960 |
| cgcgcggatc cggaagtgca ggaagcgctg cgcgcgagcc gcctggatga actgcgcgc | 1020 |
| ccgaccgcgg cggatggcct gcaggcgctg ctggatgatc gcagcgcgtt tgaagaattt | 1080 |
| gatgtggatg cggcggcggc gcgcggcatg gcgtttgaac gcctggatca gctggcgatg | 1140 |
| gatcatctgc tgggcgcgcg cggctaa | 1167 |

<210> SEQ ID NO 37
<211> LENGTH: 1323
<212> TYPE: DNA
<213> ORGANISM: ESCHERICHIA COLI

<400> SEQUENCE: 37

| | |
|---|---|
| atgcaggcgt attttgatca gctggatcgc gtgcgctatg aaggcagcaa aagcagcaac | 60 |
| ccgctggcgt ttcgccatta taacccggat gaactggtgc tgggcaaacg catggaagaa | 120 |

```
catctgcgct tgcggcgtg ctattggcat accttttgct ggaacggcgc ggatatgttt     180
ggcgtgggcg cgtttaaccg cccgtgcag cagccgggcg aagcgctggc gctggcgaaa     240
cgcaaagcgg atgtggcgtt tgaattttt cataaactgc atgtgccgtt ttattgcttt     300
catgatgtga atgtgagccc ggaaggcgcg agcctgaaag aatatattaa caactttgcg     360
cagatggtgg atgtgctggc gggcaaacag aagaaagcg gcgtgaaact gctgtggggc     420
accgcgaact gctttaccaa cccgcgctat ggcgcgggcg cggcgaccaa cccggatccg     480
gaagtgttta gctgggcggc gacccaggtg gtgaccgcga tggaagcgac ccataaactg     540
ggcggcgaaa actatgtgct gtggggcggc cgcgaaggct atgaacccct gctgaacacc     600
gatctgcgcc aggaacgcga acagctgggc cgctttatgc agatggtggt ggaacataaa     660
cataaaattg gctttcaggg caccctgctg attgaaccga accgcagga accgaccaaa     720 catcagtatg attatgatgc ggcgaccgtg tatggctttc tgaaacagtt tggcctggaa     780
aaagaaatta aactgaacat tgaagcgaac catgcgaccc tggcgggcca tagctttcat     840
catgaaattg cgaccgcgat tgcgctgggc ctgtttggca gcgtggatgc gaaccgcggc     900
gatgcgcagc tgggctggga taccgatcag tttccgaaca gcgtggaaga aaacgcgctg     960
gtgatgtatg aaattctgaa agcgggcggc tttaccaccg gcggcctgaa ctttgatgcg    1020
aaagtgcgcc gccagagcac cgataaatat gatctgtttt atggccatat tggcgcgatg    1080
gataccatgg cgctggcgct gaaaattgcg gcgcgcatga ttgaagatgg cgaactggat    1140
aaacgcattg cgcagcgcta tagcggctgg aacagcgaac tgggccagca gattctgaaa    1200
ggccagatga gcctggcgga tctggcgaaa tatgcgcagg aacatcatct gagcccggtg    1260
catcagagcg gccgccagga acagctggaa aacctggtga accattatct gtttgataaa    1320
taa                                                                  1323
```

<210> SEQ ID NO 38  
<211> LENGTH: 1320  
<212> TYPE: DNA  
<213> ORGANISM: CLOSTRIDIUM CELLULOVORANS

<400> SEQUENCE: 38

```
atgcgcgaat attttgcgaa cgtgccgaaa attaaatatg aaggcaaaga tagcaaaaac      60
ccgctggcgt ttaaatatta taccccggat gaagtggtgg cggcaaaaac catgaaagaa     120
catctgcgct ttaccctgag ctattggcat accctgaccg gcgcgggcag cgatccgttt     180
ggcgtgggca ccatgctgcg cccgtgggat tgcgcggaag atgaaatgga actggcgaaa     240
atgcgcatgg aagcgaactt tgaactgatg gataaactgg gcattgaata ttttgcgttt     300
catgatcgca tattgcgcc ggaaggcaaa accctggcgg ataccaacga aaaactggat     360
gaaattgtgg cgtattgcaa agaactgatg cagaaacatg gcaaaaaact gctgtggggc     420
accgcgaaca tgtttggcaa cccgcgcttt gtgcatggcg cggcgaccac ctgcaacgcg     480
gatgtgtttg cgtatgcggc ggcgcagacc aaaaaagcga tggatgtgac caagaactg     540 ggcggcgaaa actatgtgtt tggggcggc cgcgaaggct atgaacccct gctgaacacc     600
gatctgggcc tggaacagga taacctggcg cgcttttttc agatggcggt ggattatgcg     660
aaaaaaattg gctttaccgg ccagtttctg attgaaccga accgaaaga accgaccaaa     720 catcagtatg attttgatgt ggcgaccgtg ctgggctttc tgcgcaaata taacctggaa     780
aaatatttta aaatgaacat tgaagcgaac catgcgaccc tggcgcagca tacctttcag     840
```

| | |
|---|---|
| catgaagtgg cggtggcgcg cgtgaacggc gtgctgggca gcctggatgt gaaccagggc | 900 |
| gatccgaacc tgggctggga taccgatcag tttccgacca acatttatga tgcgaccatg | 960 |
| gtgatgtatg aagtgctgaa aaacggcggc attgcgccgg gcggcctgaa ctttgatgcg | 1020 |
| aaaacccgcc gcgcgagctt tgaaccgaaa gatctgtttc tgagctatat tgcgggcatg | 1080 |
| gataccatgg cgaaaggcct gcgcgtggcg tatagcctgc tggatgatgc ggtgctggaa | 1140 |
| aacaacacca gcgaacgcta taaaaccttt agcgaaggca ttggcaaaga tattgtggaa | 1200 |
| ggcaaagtgg attttgaaag cctggaaaaa tatgcgctgg aaaacagcgt gattagcaac | 1260 |
| aaaagcggcc gccaggaata tctggaaagc gtggtgaacc agtatatttt taacgattaa | 1320 |

<210> SEQ ID NO 39
<211> LENGTH: 1338
<212> TYPE: DNA
<213> ORGANISM: BACILLUS SUBTILIS

<400> SEQUENCE: 39

| | |
|---|---|
| atggcgcaga gccatagcag cagcgtgaac tattttggca gcgtgaacaa agtggtgttt | 60 |
| gaaggcaaag cgagcaccaa cccgctggcg tttaaatatt ataacccgca ggaagtgatt | 120 |
| ggcggcaaaa ccatgaaaga acatctgcgc tttagcattg cgtattggca tacctttacc | 180 |
| gcggatggca ccgatgtgtt tggcgcggcg accatgcagc gcccgtggga tcattataaa | 240 |
| ggcatggatc tggcgcgcgc gcgcgtggaa gcggcgtttg aaatgtttga aaaactggat | 300 |
| gcgccgtttt ttgcgtttca tgatcgcgat attgcgccgg aaggcagcac cctgaaagaa | 360 |
| accaaccaga acctggatat tattgtgggc atgattaaag attatatgcg cgatagcaac | 420 |
| gtgaaactgc tgtggaacac cgcgaacatg tttaccaacc cgcgctttgt gcatggcgcg | 480 |
| gcgaccagct gcaacgcgga tgtgtttgcg tatgcggcgg cgcaggtgaa aaaaggcctg | 540 |
| gaaaccgcga agaactgggc gcggaaaaac tatgtgtttt gggcggccg cgaaggctat | 600 |
| gaaaccctgc tgaacaccga tctgaaattt gaactggata acctggcgcg ctttatgcat | 660 |
| atggcggtgg attatgcgaa agaaattgaa tataccggcc agtttctgat tgaaccgaaa | 720 |
| ccgaaagaac cgaccaccca tcagtatgat accgatgcgg cgaccaccat tgcgtttctg | 780 |
| aaacagtatg gcctggataa ccatttaaaa ctgaacctgg aagcgaacca tgcgacctg | 840 |
| gcgggccata cctttgaaca tgaactgcgc atggcgcgcg tgcatggcct gctgggcagc | 900 |
| gtggatgcga accagggcca tccgctgctg ggctgggata ccgatgaatt tccgaccgat | 960 |
| ctgtatagca ccaccctggc gatgtatgaa attctgcaga acggcggcct gggcagcggc | 1020 |
| ggcctgaact ttgatgcgaa agtgcgccgc agcagctttg aaccggatga tctggtgtat | 1080 |
| gcgcatattg cggcatgga tgcgtttgcg cgcggcctga agtggcgca taaactgatt | 1140 |
| gaagatcgcg tgtttgaaga tgtgattcag catcgctatc gcagctttac cgaaggcatt | 1200 |
| ggcctggaaa ttaccgaagg ccgcgcgaac tttcatcccc tggaacagta tgcgctgaac | 1260 |
| aacaaaacca ttaaaaacga aagcggccgc caggaacgcc tgaaagcgat tctgaaccag | 1320 |
| tatattctgg aagtgtaa | 1338 |

<210> SEQ ID NO 40
<211> LENGTH: 1347
<212> TYPE: DNA
<213> ORGANISM: BACILLUS LICHENIFORMIS

<400> SEQUENCE: 40

| | |
|---|---|
| atgttttta aaaacgtggg catgattgaa tatgaaggcg cggatagcga aaacccgtat | 60 |

```
gcgtttaaat attataaccc ggatgaatat gtgggcggca aaaccatgaa agaacatctg      120
cgctttgcgg tggcgtattg gcatacccttt gatgcggatg gcaaagatcc gtttggcgat     180
ggcaccatgt ttcgcgcgtg gaaccgcctg acctatccgc tggataaagc gaaagcgcgc     240
gcggaaagcg cgtttgaatt ttttgaaaaa ctgggcgtgc cgtattttttg ctttcatgat    300 gtggatattg tggatgaagg cgcgacccty cgcgaaacct ttgcgtatct ggatcagatg     360
agcagctttc tgaagaaat gatggaaacc agccgcgtgc agctgctgtg aacaccgcg       420 aacatgttta cccatccgcg ctatgtgcat ggcgcggcga ccagctgcaa cgcggatgtg     480
tatgcgtatc cggcggcgaa agtgaaaaaa ggcctggata ttgcgaaaga actgggcgcg    540
gaaaactatg tgttttgggg cggccgcgaa ggctatgaaa ccctgctgaa caccgatatg    600
aaactggaac tggaaaacct ggcgagcttt tatcgcatgg cggtggaata tgcgcgcgaa    660
attggctttg atggccagtt tctgattgaa ccgaaaccga agaaccgac caaacatcag     720 tatgattttt atgcggcgac caccattgcg tttctggaaa cctatggcct gaaagatcat    780
tttaaactga acctggaagc gaaccatgcg accctggcgg ccataccttt gaacatgaa    840 ctgcgcgtgg cggcgctgca tgatatgctg gcagcattg atgcgaacca gggcgatctg     900
ctgctgggct gggataccga tgaatttccg accgatctgt atagcgcggt gctggcgatg    960
tatgaaattc tgaaagcggg cggctttaaa accggcggca ttaactttga tgcgaaagtg    1020
cgccgcccga gctttgcgga tgaagatctg tttcatgcgc atattgcggg catggatacc    1080
tatgcggtgg gcctgaaagt ggcgagccgc ctgctggaag ataaagcgct ggatcaggtg    1140
attgaagaac gctatgaaag ctataccaaa ggcattggcc tggaaattaa agaaggccgc    1200
accgatctga aaaaactggc ggcgtatgcg ctggaacatg atcatattga aaaccagagc    1260
ggccgccagg aacgcctgaa agcgaccgtg aaccgctatc tgctgaacgc gctgcgcgaa    1320
gcgccgcgcg gcaaagaaac ccgctaa                                          1347
```

<210> SEQ ID NO 41
<211> LENGTH: 1542
<212> TYPE: DNA
<213> ORGANISM: BACILLUS SPEC.

<400> SEQUENCE: 41

```
atgacccctgg aaaatttgt ggatgcgctg ccgattccgg ataccctgaa accggtgcag       60
cagaccaccg aaaaaaccta ttatgaagtg accatggaag aatgcgcgca tcagctgcat    120
cgcgatctgc cgccgacccg cctgtggggc tataacggcc tgtttccggg cccgaccatt    180
gaagtgaaac gcaacgaaaa cgtgtatgtg aaatggatga caacctgcc gagcgaacat    240 tttctgccga ttgatcatac cattcatcat agcgatagcc agcatgaaga accggaagtg    300
aaaaccgtgg tgcatctgca tggcggcgtg accccgccgg atagcgatgg ctatccggaa    360 gcgtggtttta gcaaagattt tgaacagacc ggcccgtatt ttaaacgcga agtgtatcat    420
tatccgaacc agcagcgcgg cgcgacccty tggtatcatg atcatgcgat ggcgctgacc    480
cgcctgaacg tgtatgcggg cctggtgggc gcgtatatta ttcatgatcc gaaagaaaaa    540
cgcctgaaac tgccgagcgg cgaatatgat gtgccgctgc tgattaccga tcgcaccatt    600
aacgaagatg gcagcctgtt ttatccgagc ggcccggaaa acccgagccc gagcctgccg    660
aaaccgagca ttgtgccggc gttttgcggc gataccattc tggtgaacgg caaagtgtgg    720
ccgtatctgg aagtggaacc gcgcaaatat cgctttcgcg tgattaacgc gagcaacgcg    780
```

| | |
|---|---|
| cgcacctata acctgagcct ggataacggc ggcgaattta ttcagattgg cagcgatggc | 840 |
| ggcctgctgc cgcgcagcgt gaaactgaac agctttagcc tggcgccggc ggaacgctat | 900 |
| gatattatta ttgattttac cgcgtatgaa ggcgaaagca ttattctggc gaacagcgaa | 960 |
| ggctgcggcg gcgatgcgaa cccggaaacc gatgcgaaca ttatgcagtt tcgcgtgacc | 1020 |
| aaaccgctgg cgcagaaaga tgaaagccgc aaaccgaaat atctggcgag ctatccgagc | 1080 |
| gtgcagaacg aacgcattca gaacattcgc accctgaaac tggcgggcac ccaggatgaa | 1140 |
| tatggccgcg tggtgcagct gctgaacaac aaacgctggc atgatccggt gaccgaagcg | 1200 |
| ccgaaagcgg cgaccaccga aatttggagc attgtgaacc cgacccaggg cacccatccg | 1260 |
| attcatctgc atctggtgag ctttcgcgtg ctggatcgcc gcccgtttga tattgcgcgc | 1320 |
| tatcaggaac gcggcgaact gagctatacc ggcccggcgg tgccgccgcc gccgagcgaa | 1380 |
| aaaggctgga agataccat tcaggcgcat gcgggcgaag tgctgcgcat tgcggtgacc | 1440 |
| tttggcccgt atagcggccg ctatgtgtgg cattgccata ttctggaaca tgaagattat | 1500 |
| gatatgatgc cccgatgga tattaccgat ccgcataaat aa | 1542 |

<210> SEQ ID NO 42
<211> LENGTH: 1560
<212> TYPE: DNA
<213> ORGANISM: ESCHERICHIA COLI

<400> SEQUENCE: 42

| | |
|---|---|
| atgcagcgcc gcgattttct gaaatatagc gtggcgctgg gcgtggcgag cgcgctgccg | 60 |
| ctgtggaacc gcgcggtgtt tgcggcggaa cgcccgaccc tgccgattcc ggatctgctg | 120 |
| accaccgatg cgcgcaaccg cattcagctg accattggcg cgggccagag cacctttggc | 180 |
| ggcaaaaccg cgaccacctg gggctataac ggcaacctgc tgggcccggc ggtgaaactg | 240 |
| cagcgcggca agcggtgac cgtggatatt tataaccagc tgaccgaaga aaccacccctg | 300 |
| cattggcatg gcctggaagt gccgggcgaa gtggatggcg cccgcaggg cattattccg | 360 |
| ccgggcggca aacgcagcgt gaccctgaac gtggatcagc cggcggcgac ctgctggttt | 420 |
| catccgcatc agcatggcaa aaccggccgc caggtggcga tgggcctggc gggcctggtg | 480 |
| gtgattgaag atgatgaaat tctgaaactg atgctgccga acagtgggg cattgatgat | 540 |
| gtgccggtga ttgtgcagga taaaaaattt agcgcggatg ccagattga ttatcagctg | 600 |
| gatgtgatga ccgcggcggt gggctggttt ggcgataccc tgctgaccaa cggcgcgatt | 660 |
| tatccgcagc atgcggcgcc gcgcggctgg ctgcgcctgc gcctgctgaa cggctgcaac | 720 |
| gcgcgcagcc tgaactttgc gaccagcgat aaccgcccgc tgtatgtgat tgcgagcgat | 780 |
| ggcggcctgc tgccggaacc ggtgaaagtg agcgaactgc cggtgctgat gggcgaacgc | 840 |
| tttgaagtgc tggtggaagt gaacgataac aaaccgtttg atctggtgac cctgccggtg | 900 |
| agccagatgg gcatggcgat tgcgccgttt gataaaccgc atccggtgat gcgcattcag | 960 |
| ccgattgcga ttagcgcgag cggcgcgctg ccggatacc tgagcagcct gccggcgctg | 1020 |
| ccgagcctgg aaggcctgac cgtgcgcaaa ctgcagctga gcatggatcc gatgctggat | 1080 |
| atgatgggca tgcagatgct gatggaaaaa tatggcgatc aggcgatggc gggcatggat | 1140 |
| catagccaga tgatgggcca tatgggccat ggcaacatga accatatgaa ccatggcggc | 1200 |
| aaatttgatt ttcatcatgc gaacaaaatt aacggccagg cgtttgatat gaacaaaccg | 1260 |
| atgtttgcgc ggcgaaagg ccagtatgaa cgctgggtga ttagcggcgt gggcgatatg | 1320 |
| atgctgcatc cgtttcatat tcatggcacc cagtttcgca ttctgagcga aaacggcaaa | 1380 |

```
ccgccggcgg cgcatcgcgc gggctggaaa gataccgtga aagtggaagg caacgtgagc    1440
gaagtgctgg tgaaatttaa ccatgatgcg ccgaaagaac atgcgtatat ggcgcattgc    1500
catctgctgg aacatgaaga taccggcatg atgctgggct ttaccgtgag cgatccgtaa    1560
```

<210> SEQ ID NO 43
<211> LENGTH: 1254
<212> TYPE: DNA
<213> ORGANISM: Bacillus spec.

<400> SEQUENCE: 43

```
atgaaagaac tgggccatga agtgctgaaa ccgtatgatg ctgggcggc gtatggcgaa      60 ggcaccaccg gcggcgcgat ggcgagcccg cagaacgtgt tgtggtgac caaccgcacc     120 gaactgattc aggcgctggg cggcaacaac cataccaacc agtataacag cgtgccgaaa    180
attatttatg tgaaaggcac cattgatctg aacgtggatg ataacaacca gccggtgggc    240
ccggattttt ataaagatcc gcattttgat tttgaagcgt atctgcgcga atatgatccg    300
gcgacctggg gcaaaaaaga agtggaaggc ccgctggaag aagcgcgcgt gcgcagccag    360
aaaaaacaga aagatcgcat tatggtgtat gtgggcagca acaccagcat tattggcgtg    420
ggcaaagatg cgaaaattaa aggcggcggc tttctgatta aaaacgtgga taacgtgatt    480
attcgcaaca ttgaatttga agcgccgctg gattattttc cggaatggga tccgaccgat    540
ggcaccctgg gcgaatggaa cagcgaatat gatagcatta gcattgaagg cagcagccat    600
atttggattg atcataacac ctttaccgat ggcgatcatc cggatcgcag cctgggcacc    660
tattttggcc gcccgtttca gcagcatgat ggcgcgctgg atattaaaaa cagcagcgat    720
tttattacca ttagctataa cgtgtttacc aaccatgata aagtgaccct gattggcgcg    780
agcgatagcc gcatggcgga tagcggccat ctgcgcgtga ccctgcatca taactattat    840
aaaaacgtga cccagcgcct gccgcgcgtg cgctttggcc aggtgcatat ttataacaac    900
tattatgaat ttagcaacct ggcggattat gattttcagt atgcgtgggg cgtgggcgtg    960
tttagccaga tttatgcgca gaacaactat tttagctttg attgggatat tgatccgagc    1020
ctgattatta aagtgtggag caaaaacgaa gaaagcatgt atgaaaccgg caccattgtg    1080
gatctgccga acggccgccg ctatattgat ctggtggcga gctataacga aagcaacacc    1140
ctgcagctga aaaagaagt gacctggaaa ccgatgtttt atcatgtgat tcatccgacc    1200
ccgagcgtgc cggcgctggt gaaagcgaaa gcgggcgcgg gcaacctgca ttaa           1254
```

<210> SEQ ID NO 44
<211> LENGTH: 525
<212> TYPE: DNA
<213> ORGANISM: ESCHERICHIA COLI

<400> SEQUENCE: 44

```
atggttacgt tcacactaa tcacggcgac attgttatca agaccttcga cgacaaagca      60
ccggaaacgg tgaagaattt cctggattat tgtcgcgagg ttttttacaa cataccatt     120 ttccatcgtg tcattaatgg ttttatgatc cagggtggcg gtttcgagcc gggcatgaag    180
cagaaagcca ccaaagaacc gattaagaac gaagcgaata atggcctgaa gaacacccgt    240
ggcacgctgg cgatggcgcg tacccaggca ccacatagcg cgaccgctca attctttatc    300
aacgttgttg ataacgattt cctgaacttt tccggtgaga gcttgcaagg ctggggttac    360
tgcgttttcg ccgaggttgt ggacggtatg gacgtggtcg acaaaatcaa aggtgtcgcg    420
```

```
acgggtcgca gcggtatgca ccaagatgtg ccgaaagaag atgtgattat cgagtctgtc    480
accgtgagcg agggcacatc tgaaaacttg tatttccagg gcgcc                    525
```

METHOD FOR OBTAINING ACTIVE INSOLUBLE XYLOSE ISOMERASE

FIELD OF THE INVENTION

The invention is in the field of biotechnology and involves recombinant DNA technology. It provides means and methods for obtaining an insoluble active fusion protein comprising xylose isomerase activity. It also provides recombinant fusion proteins comprising xylose isomerase activity as well as their use in converting xylose to xylulose and glucose to fructose.

BACKGROUND OF THE INVENTION

Xylose isomerase (EC 5.3.1.5) is an enzyme which converts xylose into xylulose in a reversible reaction with an equilibrium around 1:1 ratio of xylose and xylulose. The systematic name of this enzyme class is D-xylose aldose-ketose-isomerase. Other names in common use include D-xylose isomerase, D-xylose ketoisomerase, and D-xylose ketol-isomerase. This enzyme belongs to the family of isomerases, specifically those intramolecular oxidoreductases interconverting aldoses and ketoses. The xylose isomerase has now been observed in nearly a hundred species of bacteria such as *Streptomyces, Actinoplanes, Microbacterium* and *Bacillus*.

Xylose is the preferred substrate, which is interconverted to xylulose, a ketopentose, a monosaccharide containing five carbon atoms, and including a ketone functional group. This interconversion process has an industrial significance due to its applications in industrial yeast fermentation, using xylose as a carbon source. Additionally, Xylulose is considered an important chemical intermediate for polymer production. Furfural (IUPAC name: Furan-2-carbaldehyde. $C_5H_4O_2$) is regaining attention as a bio-based alternative for the production of a large variety of chemicals, including antacids, fertilizers, plastics and paints. Furfural can be obtained from xylose via isomerization to xylulose.

Many xylose isomerases can also accept D-glucose as a substrate, interconverting it to D-fructose. Accordingly, these enzymes are often referred to as glucose isomerases. This ability led to the biggest industrial application of glucose isomerases—the production high-fructose corn syrup.

High-fructose corn syrup (HFCS) (also called glucose-fructose, isoglucose and glucose-fructose syrup) is a sweetener made from corn starch that has been processed by glucose isomerase to convert some of its glucose into fructose. HFCS was first marketed in the early 1970s by the Clinton Corn Processing Company, together with the Japanese research institute where the enzyme was discovered.

As a sweetener, HFCS is often compared to granulated sugar. Advantages of HFCS over granulated sugar include ease of handling, and costs. In the U.S., HFCS is among the sweeteners that mostly replaced sucrose (table sugar) in the food industry.

In a contemporary process, corn (maize) is milled to produce corn starch and an "acid-enzyme" process is used in which the corn starch solution is acidified to begin breaking up the existing carbohydrates, and then enzymes are added to further metabolize the starch and convert the resulting sugars to fructose.

Glucose isomerases have been marketed by companies such as Enzyme Bio-systems, Genencor, Gist-Brocades, Solvay Enzyme Inc and Novo Nordisk.

Most successful commercial xylose isomerases and glucose isomerases are immobilized and as a consequence are very stable with an extremely long half life. In a typical process, the immobilized isomerase is loaded in a column and substrate (feed stock) is passed through at a rate that produces an effluent containing 42% fructose.

Methods for immobilizing enzymes are well known in the art and can be conveniently divided into three types: binding to a carrier, encapsulation in an inorganic or organic polymeric gel, or by cross-linking of the protein molecules (Sheldon Biochem. Soc. Transactions 35: 1583-1587 (2007), Cao et al., Curr. Opin. Biotechnol. 14, 387-394 (2003)).

Suekane (Z. Allg. Mikrobiol. 22: 565-576 (1982)) describes the immobilization of glucose isomerase to an ion exchange resin using the colloidal silica-glutaraldehyde method. However, binding to a carrier inevitably leads to dilution of catalytic activity resulting from the introduction of a large proportion (90-99% of the total) of non-catalytic mass. This translates to lower volumetric and space-time yields and lower catalyst productivities.

In contrast, immobilization via cross-linking of enzyme molecules with a bifunctional cross-linking agent is a carrier-free method and the resulting biocatalyst ideally comprises 100% active enzyme. The technique of protein cross-linking, via reaction of e.g. glutaraldehyde with reactive $NH_2$ groups on the protein surface, was originally developed more than 40 years ago (reviewed in Cao et al., Curr. Opin. Biotechnol. 14, 387-394 (2003)). However, the cross-linked enzymes exhibited low activity retention, poor reproducibility and low mechanical stability and, owing to their gelatinous nature, were difficult to handle. Consequently, binding to a carrier became the most widely used methodology for enzyme immobilization.

The use of CLECs (cross-linked enzyme crystals) as industrial biocatalysts was introduced in the early 1990s and subsequently commercialized by Altus Biologics (St. Clair et al., J. Am. Chem. Soc. 114, 7314-7316 (1992), Margolin, A. L., Trends Biotechnol. 14, 223-230 91996 (1996), Lalonde, J. Chemtech 27, 38-45 (1997) and Margolin, A. L. and Navia, M. A., Angew. Chem. Int. Ed. Engl. 40, 2204-2222 (2001)).

The method was applicable to a broad range of enzymes and CLECs proved significantly more resistant against denaturation by heat, organic solvents and proteolysis than the corresponding soluble enzyme or lyophilized (freeze-dried) powder. Their operational stability, controllable particle size and ease of recycling, coupled with their high catalyst and volumetric productivities, made them ideally suited for industrial biotransformations. An inherent disadvantage of CLECs is the need to crystallize the enzyme, a laborious procedure requiring an enzyme of high purity.

Another immobilization method makes use of the well known property of enzymes to precipitate as physical aggregates held together by non-covalent bonding without perturbation of their tertiary structure. This may be caused by the addition of salts, or water-miscible organic solvents or non-ionic polymers, to aqueous solutions of enzymes.

In a method known as CLEA (cross-linked enzyme aggregates) these aggregates are covalently cross-linked to render them permanently insoluble while maintaining the pre-organized superstructure of the aggregates and, hence, their catalytic activity. Disadvantage of the CLEA method is that it is less suited for producing immobilized enzyme such as xylose isomerase or glucose isomerase on an industrial scale since enzyme precipitation involves the use of large volume of solvents and also increases the required equipment size, inflicts additional cost and often creates toxic waste. It also may cause partial denaturation of the enzyme causing part of the enzyme to become irreversibly inactivated.

It would be advantageous to have a method for the production of immobilized xylose isomerases or glucose isomerases that is easy to perform, economical and yields active enzyme with a high specific activity.

LEGEND TO THE FIGURES

FIG. 1: Diagram showing the relative enzymatic activity recovered from the pellet or supernatant of lysed recombinant cells. After cell lysis, 1 ml of cell lysate of each sample was centrifuged for 2 minutes at 14 000 g in a table centrifuge. Supernatant (soluble proteins) and pellet (insoluble proteins) were collected and used to measure activity of the laccase, pectinase or xylose isomerase fusion proteins.

Figure 2:
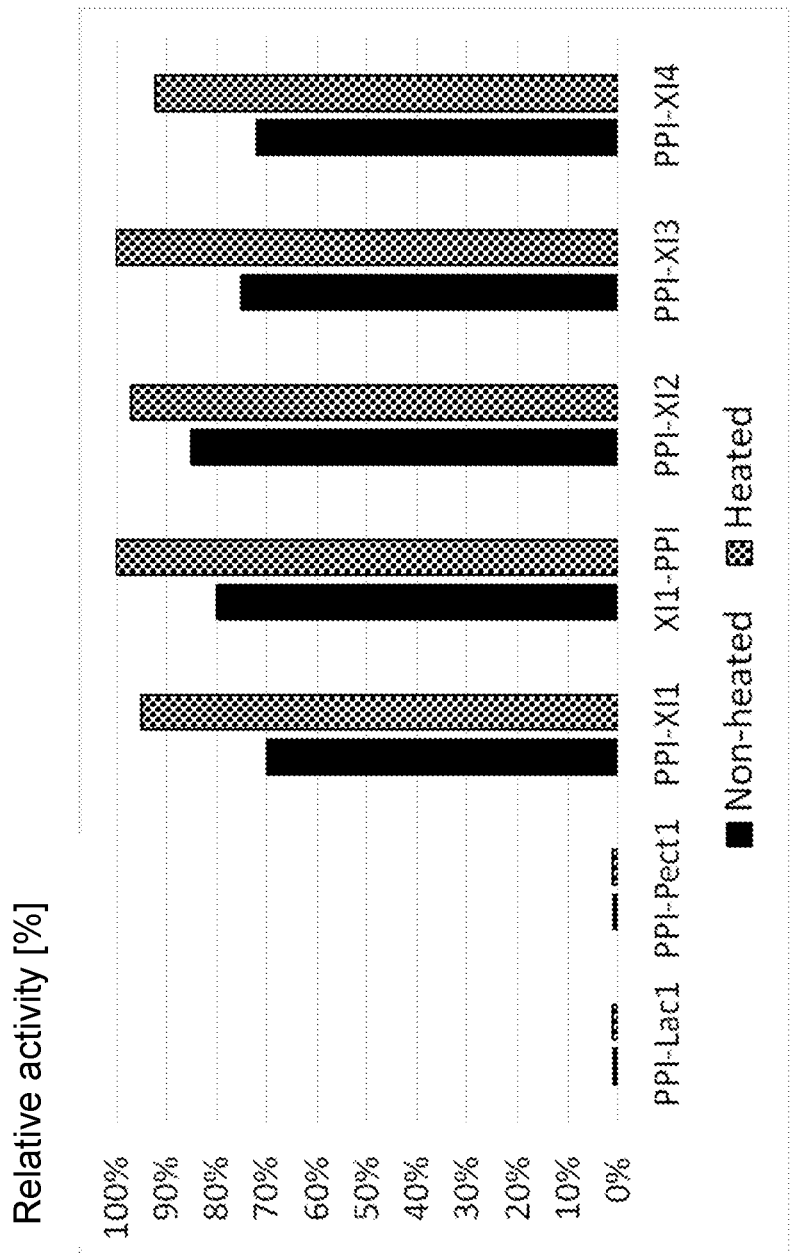

FIG. 2: Diagram showing the fraction of the total xylose isomerase activity found in the pellet of heated and none heated cell lysates. After cell lysis, 1 ml of cell lysate was heated in a water bath for 30 minutes at 70 degrees Celsius. Thereafter, the heated and non-heated samples were processed as described in example 7.

Figure 3:
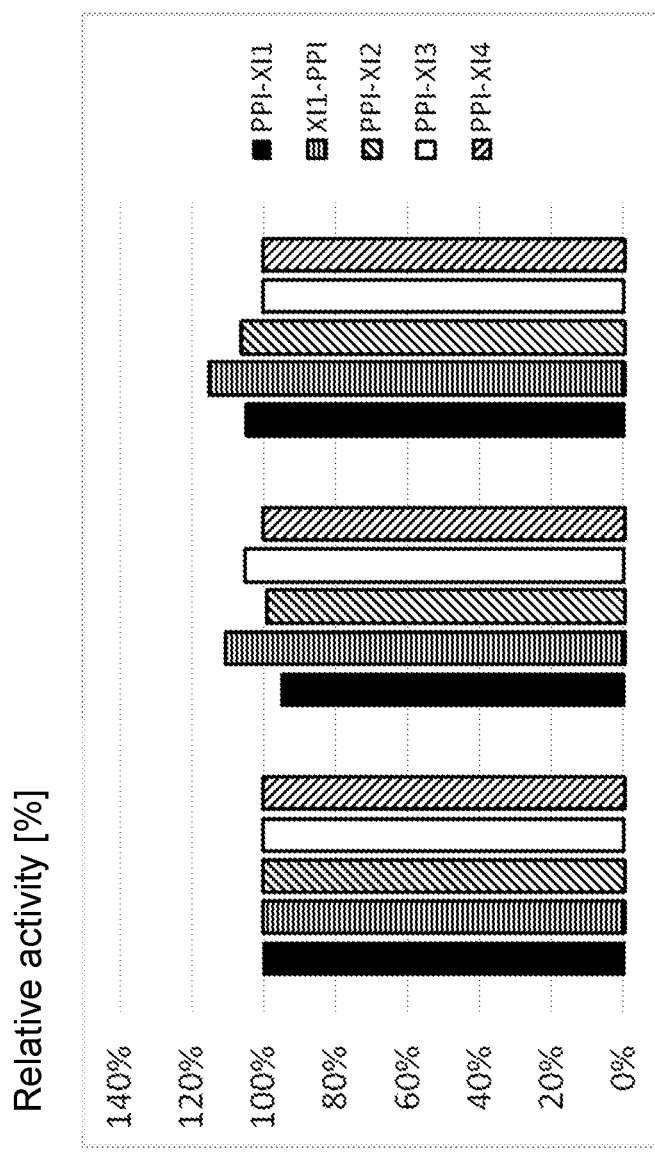

FIG. 3: Diagram showing the ability of the insoluble enzyme fractions to be reused. Three consecutive rounds of incubation were performed with a xylose solution as the substrate. After one hour of reaction time, the enzymes were recovered by centrifugation and after removal of the supernatant, subjected to a second and third round of incubation with the xylose substrate as described in example 8.

Figure 4:
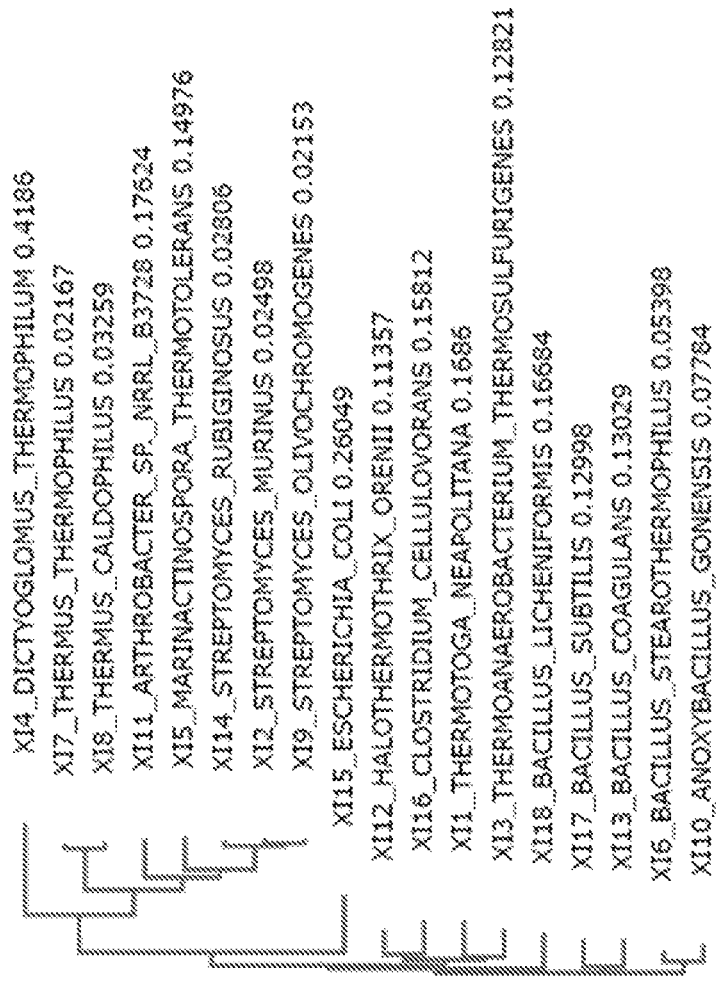

FIG. 4: Phylogenetic tree showing the relationship between the xylose isomerases exemplified herein. The number near the microorganism name is so called branch length, which indicates the average number of changes per aminoacid position in relation to the closest "common ancestor" depicted by the closest branching point on the diagram.

SUMMARY OF THE INVENTION

We surprisingly observed that xylose isomerases could be obtained in an active and insoluble form when they were produced as a fusion protein with a peptidylprolyl isomerase (PPIase). The invention therefore relates to a method for obtaining active insoluble xylose isomerase, comprising the expression in a host organism of a recombinant gene encoding a fusion protein comprising a xylose isomerase in combination with a PPIase, thereby obtaining the active insoluble xylose isomerase.

The invention also relates to a recombinant fusion protein obtainable by a method as described herein and its use in converting xylose to xylulose or converting glucose to fructose.

DETAILED DESCRIPTION OF THE INVENTION

Peptidylprolyl isomerase (also known as Prolyl isomerase or PPIase) is an enzyme (EC 5.2.1.8) found in both prokaryotes and eukaryotes that interconverts the cis and trans isomers of peptide bonds with the amino acid proline (Fischer G, Schmid F X, Biochemistry 29: 2205-2212 (1990)). Proline has an unusual conformationally restrained peptide bond due to its cyclic structure with its side chain bonded to its secondary amine nitrogen. Most amino acids have a strong energetic preference for the trans peptide bond conformation due to steric hindrance, but proline's unusual structure stabilizes the cis form so that both isomers are populated under biologically relevant conditions. Proteins with prolyl isomerase activity include cyclophilin, FKBPs, and parvulin, although larger proteins can also contain prolyl isomerase domains.

Prolyl isomerase activity was first discovered using a chymotrypsin-based assay. The proteolytic enzyme chymotrypsin has a very high substrate specificity for the four-residue peptide Ala-Ala-Pro-Phe only when the proline peptide bond is in the trans state. Adding chymotrypsin to a solution containing a reporter peptide with this sequence results in the rapid cleavage of about 90% of the peptides, while those peptides with cis proline bonds—about 10% in aqueous solution—are cleaved at a rate limited by uncatalyzed proline isomerization. The addition of a potential prolyl isomerase will accelerate this latter reaction phase if it has prolyl isomerase activity.

Protease-free assays for PPIase activity have also been reported (Zhang et al. J. Bacteriol. 189: 7942-7944 (2007), Janowski et al., Anal. Biochem. 252:299-307 (1997)). Functional PPIase activity assays are commercially available from Selcia, Fyfield business & Research Park, Fyfield Road, Ongar, Essex CM5 0GS United Kingdom.

We constructed recombinant genes, each encoding a fusion protein comprising and consisting essentially of a PPIase polypeptide covalently attached to a protein with xylose isomerase activity. Upon expression of the fusion proteins in a recombinant host organism, the xylose isomerase activity was found in the insoluble pellet obtained after lysis of the cells (FIG. 1).

Hence, the invention relates to a method for obtaining active insoluble xylose isomerase, comprising the expression in a host organism of a recombinant gene encoding a fusion protein comprising a recombinant xylose isomerase and a PPIase.

It appeared that the PPIase part of the fusion protein could be attached to the amino-terminus as well as the carboxy-terminus of the xylose isomerase. Both had the same effect with respect to the recovery of the active insoluble fusion protein. The PPIase part of the fusion protein is also referred to herein as the "PPI-tag" or the "PPIase tag". This is shown in FIG. 1.

This finding was the more surprising since PPIase is known to enhance the solubility of polypeptides, co-expressed in a recombinant host like *E. coli* (de Marco, A., Microbial Cell Factories 2009, 8:26 doi:10.1186/1475-2859-8-26). It has also been described to increase the solubility of scFvs and Fab fragments (Bothmann H, Plückthun A: Nat Biotechnol 1998, 16:376-380, Hayhurst A, Harris WJ. Prot. Expr. Purif. 1999, 15: 336-343, Lin et al., in *E. coli*. Prot Expr Purif 2008, 59:55-63.)

The term "insoluble" in this context relates to the solubility of the fusion protein in an aqueous solution, such as phosphate buffered saline. More in particular it relates to solubility in lysis buffer (50 mM Tris-HCl pH7.4, 1% Triton X100, 1 mM CoCl2). A protein is defined herein as being insoluble if 60% or more, such as 70, 80, 85, 90 or even more than 95% of the protein is found in the pellet after incubation at room temperature for 30 minutes and centrifugation at 14.000 g for 2 minutes.

The term "active" as used herein refers to the enzymatic activity of xylose isomerases or glucose isomerases. Assays for determining such activity are described herein and well known in the art.

In a preferred embodiment, the fusion protein is produced in a bacterium, such as *Bacillus* or *Escherichia*. *Bacillus* subtilis and *E. coli* are preferred. Production of the fusion protein in other hosts is also possible; yeast and fungal hosts are therein preferred.

In a control experiment, a xylose isomerase gene was expressed in *E. coli* with and without the PPIase tag. It was found that xylose isomerase activity could be obtained in both experiments. However, whereas the active xylose isomerase expressed without the PPIase tag was exclusively found in the soluble fraction, Xylose isomerase activity of the fusion protein comprising the PPIase tag was predominantly present in the insoluble pellet after lysis of the cells. We repeated this experiment for 18 different xylose isomerases (FIG. 4, Table 1, SEQ ID NO: 1-18)) and found that this was true for all of them.

In another control experiment, we showed that this effect was specific for xylose isomerases. When laccases or a pectinase (SEQ ID NO: 19-21) were expressed with and without a PPIase tag, the laccase or pectinase activity was always found exclusively in the soluble fraction (FIG. 1).

Hence, the invention relates to a method for obtaining active insoluble xylose isomerase, comprising the expression in a host organism of a recombinant gene encoding a fusion protein comprising a xylose isomerase in combination with a PPIase, thereby obtaining the active insoluble xylose isomerase.

We also showed that the effect of the PPIase tag to yield insoluble xylose isomerases, was independent of whether the PPIase tag was attached to the N-terminus or C-terminus of the xylose isomerase. In a representative example we compared the xylose isomerase activity in the soluble and insoluble fractions obtained from a recombinant host, expressing a fusion protein comprising a xylose isomerase according to SEQ ID NO: 1 with an N-terminal and a C-terminal PPIase tag. We found that for both the N-terminal and C-terminal recombinant fusion proteins, xylose isomerase activity was predominantly found in the insoluble fraction (FIG. 1).

Hence, the invention relates to a method as described above wherein the PPIase is attached to either the N-terminus and/or the C-terminus of the xylose isomerase.

We also showed that the effect of obtaining active, insoluble xylose isomerase is independent from the host organism used to produce the fusion protein. Rather, this is an inherent property of the fusion protein, as was shown in the experiments described in example 9. Therein, the supernatant of the cell lysates, containing the residual soluble and active xylose isomerase, was heated to 70 degrees Celsius for 30 minutes at different pH values. It was found that the formation of enzymatically active aggregates can occur in vitro, in the absence of cells, at various pH values and without the initial presence of already existing aggregates.

However, for ease of handling and for economical reasons, *Escherichia coli* is preferred as the host organism in the present invention.

In another preferred embodiment, the recombinant cells are lysed after expression of the recombinant fusion protein, to recover the active, insoluble fusion protein. Also preferred is when the step of recovering the active, insoluble fusion protein comprises a heat treatment step.

A suitable heat treatment for most of the xylose isomerases exemplified herein is the treatment at 70 degrees Celsius, for 30 minutes. Other temperatures and times may be suitable as well, for example, fusion proteins comprising a xylose isomerase moiety according to SEQ ID NO: 15-18 were best recovered in a method employing a heat treatment step of 50 degrees Celsius for 60 minutes. Using his common technical knowledge and the present disclosure, a person skilled in the art will know how to determine and apply the optimal temperature, time and other conditions for the heat treatment step in obtaining active, insoluble xylose isomerases.

Any PPIase may advantageously be used in the present invention, since all PPIases have a comparable and specific enzymatic activity. In a preferred embodiment, the PPIase is derived from bacterial origine, such as from an enterobacteria. In a particularly preferred embodiment according to the invention, a cyclophilin-type PPIase according to SEQ ID NO: 22 is used, or a PPIase that comprises an amino acid sequence that is at least 90% identical to the amino acid sequence according to SEQ ID NO: 22.

As used herein, the degree of identity between two or more amino acid sequences is equivalent to a function of the number of identical positions shared by the sequences; i.e., % identity=number of identical positions divided by the total number of aligned positions×100, excluding gaps, which need to be introduced for optimal alignment of the two sequences, and overhangs. The alignment of two sequences is to be performed over the full length of the polypeptides.

The comparison (aligning) of sequences is a routine task for the skilled person and can be accomplished using standard methods known in the art. For example, a freeware conventionally used for this purpose is "Align" tool at NCBI recourse http://blast.ncbi.nlm.nih.gov/Blast.cgi?PAGE_TYPE=BlastSearch&BLAST_SPEC=blast2seq &LINK_LOC=align2seq. Other commercial and open software such as Vector NTI are also suitable for this purpose.

We have also shown herein that the effect underlying the invention is not restricted to a particular xylose isomerases according to a particular sequence. The xylose isomerases as exemplified herein show a great diversity in their amino acid sequence (FIG. 4). The most distant examples having only 19% sequence identity to each other. Nevertheless, they all exhibited the same effect of yielding an active and insoluble xylose isomerase after expression as a fusion protein with a PPIase tag.

Accordingly, in a preferred method according to the invention, the xylose isomerase comprises an amino acid sequence selected from the group consisting of a sequence according to SEQ ID NO: 1-18, or an amino acid sequence that is at least 90% identical to an amino acid sequence selected from the group consisting of a sequence according to SEQ ID NO: 1-18.

Many xylose isomerases also have glucose isomerase activity. Hence, the invention also relates to a method as described above wherein the xylose isomerase also has glucose isomerase activity. Some of the xylose isomerases exemplified herein also have profound glucose isomerase activity, for example XI1, XI2, XI4, XI9 and XI13.

The invention also relates to recombinant fusion proteins obtainable by any of the methods described above. More in particular, the invention relates to a recombinant fusion protein as described above, comprising a recombinant xylose isomerase and a PPIase.

The invention also relates to a recombinant fusion protein as described above, that has xylose isomerase activity and is insoluble.

The invention also relates to a recombinant fusion protein as described above, wherein the PPIase is attached to the N-terminus of the xylose isomerase.

The invention also relates to a recombinant fusion protein as described above, wherein the PPIase is attached to the C-terminus of the xylose isomerase.

The invention also relates to a recombinant fusion protein as described above, produced in *E. coli*.

The invention also relates to a recombinant fusion protein as described above, wherein the PPIase comprises an amino acid sequence according to SEQ ID NO: 22, or a sequence that is at least 90% identical to the amino acid sequence according to SEQ ID NO: 22.

The invention also relates to a recombinant fusion protein as described above, wherein the xylose isomerase comprises an amino acid sequence selected from the group consisting of sequences according to SEQ ID NO: 1-18, or an amino acid sequence that is at least 90% identical to an amino acid sequence selected from the group consisting of a sequence according to SEQ ID NO: 1-18.

The invention also relates to a recombinant fusion protein as described above, wherein the xylose isomerase also has glucose isomerase activity.

The active, insoluble xylose isomerases as described herein may advantageously be used in any application wherein the interconversion of xylose to xylulose is advantageous. The same is true for the glucose isomerases described herein.

EXAMPLES

Example 1: Preparation of a Polypeptide Comprising a Polypeptide According to SEQ ID NO: 1-21

The DNA constructs encoding the polypeptides according to SEQ ID NO: 1-21 were designed using codon frequencies optimized for expression in E. coli and commercially synthesized and cloned into a standard plasmid vector pET28a+ for cytoplasmic expression. The resulting recombinant xylose isomerases are referred to as XI1-XI18, Lac1, Lac2, Pect1 respectively.

The same DNA fragments were also cloned into another plasmid vector based on a standard pET28a+ additionally containing a nucleotide sequence encoding peptidyl-prolyl isomerase (PPIase, SEQ ID NO: 22). This resulted in a nucleotide sequence encoding an N-terminal tag to the expressed xylose isomerase protein. The recombinant proteins comprising the PPIase tag at their N-terminus are referred to as PPI-XI1-PPI-XI18 respectively.

Also, DNA encoding SEQ ID NO: 1 or SEQ ID NO: 2 were cloned into a plasmid vector based on a standard pET28a+ additionally containing a nucleotide sequence encoding peptidyl-prolyl isomerase (PPIase, SEQ ID NO: 22) in such a way that this nucleotide sequence encodes an C-terminal tag to the expressed xylose isomerase. The recombinant proteins comprising the PPIase tag at the C-terminus are referred to as XI1-PPI and XI2-PPI respectively.

As a control, a COT A laccase from B. subtilis, a laccase (CuEO) from E. coli and a pectate lyase from B. subtilis (SEQ ID NO: 19-21 resp.) were cloned into a plasmid vector based on a standard pET28a+, additionally containing a nucleotide sequence encoding peptidyl-prolyl isomerase (PPIase, SEQ ID NO: 22) in such a way that this nucleotide sequence encodes an N-terminal tag to the expressed laccases or pecate lyase.

All the recombinant genes were expressed in Escherichia coli BL21(DE3) under the control of the T7-RNA-polymerase promoter. Nucleotide sequences encoding the xylose isomerases according to SEQ ID NO: 1-SEQ ID NO: 18 are provided herein as SEQ ID NO: 23-40 respectively (Table 1).

Example 2: Heterologous Expression of Recombinant Polypeptides

Protein production was carried out in E. coli BL21(DE3) strain according to the plasmid manufacturer protocol available at http://richsingiser.com/4402/Novagen%20pET%20system%20manual.pdf. The incubation temperature for protein production was 30 degrees Celsius, which was found optimal for maximum yield of the active xylose isomerase. Cells were lysed using lysis buffer (50 mM Tris-HCl pH7.4, 1% Triton X100, 1 mM CoCl2) thereby obtaining a cell lysate. The cell lysate was optionally heated at 70 degrees Celsius for 30 min as described herein.

Cell lysates comprising combinant laccases were prepared the same way except that the lysis buffer contained 1 mM CuCl2 instead of 1 mM CoCl2. Recombinant pectinases were prepared the same way except that the lysis buffer contained 1 mM CaCl2) instead of 1 mM CoCl2.

Example 3: Xylose Isomerase Activity Assay

Xylose isomerase activity was determined in a xylose solution (100 mM xylose, 10 mM MOPS pH 8.0, 1 mM MgCl2). Approximately 0.1 activity units/mL of xylose isomerase activity was used. The amount of enzyme was selected so that during the reaction time the product formation remains linear. Reaction was incubated at 70 C for 15 min, unless specified otherwise in the example.

Xylose isomerase activity (isomerization reaction rate) was determined by measuring xylulose level in the reaction mixture according to the protocol described in Schenk and Bisswanger; (A microplate assay for D-xylose/D-glucose isomerase. Enzyme and Microbial Technology (Elsevier Science Inc, N Y, 1998), V22, pp. 721-723.)

Measurement was performed in the linear stage of the reaction course wherein product accumulation is linear with time. Ten-microliter aliquots of the reaction mixture were taken and pipetted into a 96-well plate, 40 ul of water was added resulting in 50 ul sample. In some cases, higher dilution of the reaction mixture with water was used to prepare 50 ul of the diluted sample to match the dynamic range of the method. 150 ul of a freshly prepared 1:1 mixture (v/v) of solution A (0.05% resorcinol in ethanol) and solution B (0.216 g FeNH4(SO4)2*12 H2O in 1 l concentrated HCl) were added. For color development, the plate was incubated at 80° C. for 40 min. The absorbance was measured with a microplate reader (Thermo) at 630 nM.

Example 4: Pectinase Activity Assay

Pectinase (synonym: pectate lyase) activity assay was carried out essentially as described in Takao M, Nakaniwa T, Yoshikawa K, Terashita T, Sakai T., "Purification and characterization of thermostable pectate lyase with protopectinase activity from thermophilic Bacillus sp. TS 47". Biosci Biotechnol Biochem. 2000 64:2360-7. In more detail, pectate lyase activity was assayed by measuring the increase in absorbance at 235 nm of the reaction mixture. Polygalacturonic acid (PGA) sodium salt from de-methylated citrus pectin (purchased from MegaZyme) was used as substrate. A reaction mixture containing 1 ml of 0.1% PGA in 10 mM Tris-HCl buffer, pH 8.0 and 0.5 mM CaCl2), and an appropriate amount of enzyme solution was incubated for 30 minutes at 60 degrees C.

The reaction was stopped by placing the mixture in 100 degrees C. (boiling water bath) for 5 min. Pectate lyase activity was calculated from the difference in absorption of the reaction mixture at 235 nm at the start and at the end of the reaction.

One unit of pectate lyase activity was defined as the enzyme amount oxidizing 1 micro mole of substrate per minute. Using absorption coefficient of the unsaturated bond at the 4-5 position of the uronic acid residue at 235 nm 4 600 mol-1×cm-1.

Example 5: Laccase Activity Measurement

The term "laccase activity" is used herein to mean the capability to act as a laccase enzyme, which may be expressed as the maximal initial rate of the specific oxidation reaction. Relative activity was measured by oxidation of syringaldazine. Reaction course was monitored by change in absorbance at 526 nM (extinction coefficient of syringaldazine at 526 nm is 65 000 M-1 cm-1). The appropriate reaction time was determined to provide initial rates of oxidation when color development is linear in time. Syringaldazine concentration in the reaction mixture was 1 mM to provide maximum initial rates (substrate saturation conditions).

Typically, reactions were carried out in 1 ml volume of 50 mM Tris-HCl buffer pH 8, the substrate was preheated to the desired temperature (60 degrees Celsius) and reaction was initiated by the addition of the enzyme. After the reaction time has elapsed, absorbance at 526 nm of the reaction mixtures was determined by a spectrophotometer, and the absorbence of the blank sample (containing no enzyme) was subtracted.

One unit of laccase activity was defined as the enzyme amount oxidising 1 micro mole of substrate per minute.

Example 6: Relative Xylose Isomerase Activity in Supernatant and Pellet of Cell Lysates After cell lysis, 1 ml of cell lysate comprising xylose isomerases comprising an amino acid according to SEQ ID NO: 1-14 was heated in a water bath for 30 min at 70 C. One ml of cell lysate comprising enzymes comprising an amino acid according to SEQ ID NO: 15-18 was heated in a water bath for 30 min at 50 C. One ml of cell lysate comprising enzymes comprising an amino acid according to SEQ ID NO: 19-21 was heated in a water bath for 30 min at 70 C.

Thereafter, each sample was centrifuged for 2 min at 14.000 g in a table centrifuge. The supernatant (sup 1) was collected and stored at room temperature. The pellet was resuspended in 1 ml of lysis buffer and centrifuged again (to wash away any soluble protein trapped in the pellet). The supernatant was added to the supernatant obtained in the first centrifugation step (sup1) and used to measure activity of the soluble protein. The pellet was re-suspended in 2 ml lysis buffer (the same volume as the total volume of the soluble fraction); this suspension was used to measure insoluble fraction activity.

It was found that the majority of the PPIase-tagged xylose isomerase activity resided in the insoluble fraction, whereas PPIase-tagged other enzymes such as laccases and pectinases were found in the soluble fraction. This is shown in FIG. 1. In a control experiment using the same 21 enzymes without a PPIase tag, all activity was found in the supernatant (soluble fraction).

Example 7: Relative Activity of PPI-Tagged Xylose Isomerases, Laccases and a Pectinase in the Insoluble Fractions of Heated and Non-Heated Cell Lysate In this example, the effect of heat treatment of the cell lysate was investigated. After cell lysis, a sample of 1 ml of cell lysate comprising PPIase-tagged xylose isomerases, a laccase or a pectinase was heated in a water bath for 30 min at 70 C. After centrifugation for 2 min at 14.000 g, the enzymatic activity in the insoluble fraction was compared to the activity of the insoluble fraction of same sample without the heat treatment.

We observed that heating effectively promotes aggregates formation. Incubation for 30 min in 70 C was sufficient to convert essentially all enzymatic activity to the insoluble fraction in XI samples, whereas in laccase and pectinase samples all activity remained in solution (FIG. 2). No loss of total activity was observed upon aggregation.

Example 8: Repeated Use of Immobilized Xylose Isomerases

To test the ability of the insoluble aggregates of the enzymes to be reused, three consecutive rounds of incubation were performed with xylose solution (100 mM xylose, 10 mM MOPS pH 8.0, 1 mM MgCl2) as the substrate. After one hour of reaction time at 70 C, the enzymes were recovered by centrifugation (2 min at 14000 g) and after removal of the supernatant, subjected to a second round of incubation with the xylose substrate.

For this purpose, fresh xylose substrate was added to the pellets containing the enzymes, pellets were re-suspended and reactions were allowed to continue for another hour. After that, enzymes were recovered again and a third round of incubation with xylose substrate was carried out the same way. Supernatants from all three reactions with each enzyme were analyzed for xylulose concentration to determine enzyme activity.

FIG. 3 shows the enzymatic activities of aggregates of XI1 with N-terminally and C-terminally attached PPI tag as well as XI2-XI4 with N-terminal tag in the three consecutive rounds.

This demonstrates that enzyme aggregates remain fully insoluble under the reaction conditions and can be quantitatively recovered from the mixtures by centrifugation and reused.

Example 9: Formation of Insoluble Aggregates from Soluble Fraction of the Lysate Soluble fraction of PPI-XI1 lysate containing approximately 30% of the total enzymatic activity was obtained by centrifuging the sample 2 min 14000 g and collecting the supernatant. Aliquots of this sample were diluted five-fold with the following buffers at increasing pH values:
  100 mM sodium succinate buffer pH 5.0 or
  100 mM sodium acetate buffer pH 6.0 or
  100 mM phosphate buffer pH 7.0 or
  100 mM MOPS buffer pH 8.0 or
  100 mM MOPs buffer pH 9.0.

Aliquots of the diluted samples were collected for activity measurement ("before heating soluble" samples), rest of the volume of the diluted samples (1 mL) was incubated for 30 min at 70 C and centrifuged for 2 min at 14000 g. Supernatant was collected to measure activity in soluble fraction ("after heating soluble"), pellet was suspended in 1 ml of the same buffer and used to measure activity in the insoluble fraction ("after heating insoluble"). Virtually all the activity was found in insoluble fraction. Total amount of activity (soluble+insoluble) remained the same after heating as before heating.

This experiment shows that formation of aggregates can occur in vitro, in the absence of cells, at various pH values and without the initial presence of already existing aggregates.

TABLE 1

DNA and amino acid sequences as exemplified herein. SEQ ID NO: 1-
18 are xylose isomerases from a number of bacterial species, known in the art per se. SEQ
ID NO: 19 and 20 are a COT A laccase from *Bacillus subtilis* and *Escherichia coli*
respectively, SEQ ID NO: 21 is a pectate lyase (synonym: pectinase) from *Bacillus subtilis*.
SEQ ID NO: 22 represents a PPlase from *Ecoli*. SEQ ID NO:s 23-44 are DNA sequences
encoding the polypeptides with an amino acid sequence according to SEQ ID NO:s 1-22.

| SEQ ID NO: | Sequence | |
|---|---|---|
| 1 | MAEFFPEIPK VQFEGKESTN PLAFKFYDPE EIIDGKPLKD HLKFSVAFWH TFVNEGRDPF | 60 |
|  | GDPTADRPWN RYTDPMDKAF ARVDALFEFC EKLNIEYFCF HDRDIAPEGK TLRETNKILD | 120 |
|  | KVVERIKERM KDSNVKLLWG TANLFSHPRY MHGAATTCSA DVFAYAAAQV KKALEITKEL | 180 |
|  | GGEGYVFWGG REGYETLLNT DLGFELENLA RFLRMAVDYA KRIGFTGQFL IEPKPKEPTK | 240 |
|  | HQYDFDVATA YAFLKSHGLD EYFKFNIEAN HATLAGHTFQ HELRMARILG KLGSIDANQG | 300 |
|  | DLLLGWDTDQ FPTNVYDTTL AMYEVIKAGG FTKGGLNFDA KVRRASYKVE DLFIGHIAGM | 360 |
|  | DTFALGFKVA YKLVKDGVLD KFIEEKYRSF REGIGRDIVE GKVDFEKLEE YIIDKETIEL | 420 |
|  | PSGKQEYLES LINSYIVKTI LELR | 444 |
| 2 | MSFQPTPEDR FTFGLWTVGW QGRDPFGDAT RPALDPVETV QRLAELGAYG VTFHDDDLIP | 60 |
|  | FGSSDTERES HIKRFRQALD ATGMTVPMAT TNLFTHPVFK DGGFTANDRD VRRYALRKTI | 120 |
|  | GNIDLAAELG AKTYVAWGGR EGAESGGAKD VRDALDRMKE AQDLLGEYVT AQGYDLRFAI | 180 |
|  | EPKPNEPRGD ILLPTVGHAL AFIERLERPE LYGVNPEVGH EQMAGLNFPH GIAQALWAGK | 240 |
|  | LFHIDLNGQS GIKYDQDLRF GAGDLRAAFW LVDLLETAGY EGPRHFDFKP PRTEDFDGVW | 300 |
|  | ASAAGCMRNY LILKDRAAAF RADPEVQEAL RAARLDQLAQ PTAADGLDAL LADRAAFEDF | 360 |
|  | DVDAAAARGM AFEHDLQLAM DHLLGARG | 388 |
| 3 | MNKYFENVSK IKYEGPKSNN PYSFKFYNPE EVIDGKTMEE HLRFSIAYWH TFTADGTDQF | 60 |
|  | GKATMQRPWN HYTDPMDIAK ARVEAAFEFF DKINAPYFCF HDRDIAPEGD TLRETNKNLD | 120 |
|  | TIVAMIKDYL KTSKTKVLWG TANLFSNPRF VHGASTSCNA DVFAYSAAQV KKALEITKDL | 180 |
|  | GGENYVFWGG REGYETLLNT DMEFELDNFA RFLHMAVDYA KEIGFEGQFL IEPKPKEPTK | 240 |
|  | HQYDFDVANV LAFLRKYDLD KYFKVNIEAN HATLAFHDFQ HELRYARING VLGSIDANTG | 300 |
|  | DMLLGWDTDQ FPTDIRMTTL AMYEVIKMGG FDKGGLNFDA KVRRASFEPE DLFLGHIAGM | 360 |
|  | DAFAKGFKVA YKLVKDRVFD KFIEERYASY KDGIGADIVS GKADFRSLEK YALERSQIVN | 420 |
|  | KSGRQELLES ILNQYLFAE | 439 |
| 4 | MPFVDHRAQK IRRSKEELLK HMQTFKLDLK FSVGIWYFTP GGGRFHEPYV EQKSIPERIE | 60 |
|  | MAAEMAKFGV KGIEAHYPAE VNEENLHLYK QLEKEAGIRL VAVPLSLFYD KIFEFGSLSN | 120 |
|  | PYEKYRKVAY ERLVNGLKLV KEANADICII WPGIDGYTYS YGHLYYHMWD TFEELVAQAM | 180 |
|  | DEVPGVQVAI EPKPYEPAPN NIYRTTADGI LAARDIEARL KNPENLKLLQ EGHALVGLNP | 240 |
|  | EVGHVRMGFE DLPYAYARVA REGRLFHTHW NSQPLGNYDQ DLNIGVVDWD STEALLYTLK | 300 |
|  | MVGYQGYFGI DINPERMPVI KAIEINTKVL QIMNERIERL PHDRIIECYF DPENHRGELE | 360 |
|  | LILAENHK | 368 |
| 5 | MSSYRPEPED KFSFGLWTVG WRGVNTFGDA VRPPLDPAEA VHRLAGLGAY GITFHDDDLI | 60 |
|  | PPGSSAAERD AILGRFRKAL DETGLTVPMA TVNLFSHPVF RDGGFTSNSR ATRRYAIRKA | 120 |
|  | VRAIDLAAEL GARTFVCWGG QDGAETEAGK DDRAALERLR EAFNLMCGYT REQGYDLRFA | 180 |
|  | VEPKPNEPRG DVLLPTVGHA LAFIGELEHP EMVGVNPEVG HEQMAGLNFA HGVAQALWHG | 240 |
|  | KLFHIDLNGQ RGVKYDQDLR FGAGDVKEAF FLVDLLERSG YDGPRHFDFK PPRTEDVDGV | 300 |
|  | WESAAACMRN YLILKEKAAA FRADPEVADA LAASRVAELS EPTLGTGESL ADLLAEDFDV | 360 |
|  | DAAGERGYHF ERLDQLAMDH LFGVR | 385 |
| 6 | MPYFDNISTI AYEGPASKNP LAFKFYNPEE KVGDKTMEEH LRFSVAYWHT FTGDGSDPFG | 60 |
|  | AGNMIRPWNK YSGMDLAKAR VEAAFEFFEK LNIPFFCFHD VDIAPEGETL KETYKNLDII | 120 |
|  | VDMIEEYMKT SKTKLLWNTA NLFTHPRFVH GAATSCNADV FAYAAAKVKK GLEIAKRLGA | 180 |
|  | ENYVFWGGRE GYETLLNTDM KLELDNLARF LHMAVDYAKE IGFDGQFLIE PKPKEPTKHQ | 240 |
|  | YDFDVATALA FLQTYGLKDY FKFNIEANHA TLAGHTFEHE LRVARIHGML GSVDANQGDM | 300 |
|  | LLGWDTDEFP TDLYSTTLAM YEILKNGGLG RGGLNFDAKV RRGSFEPEDL FYAHIAGMDS | 360 |
|  | FAVGLKVAHR LIEDRVFDEF IEERYKSYTE GIGREIVEGT ADFHKLEAHA LQLGEIQNQS | 420 |
|  | GRQERLKTLL NQYLLEVCAA R | 441 |
| 7 | MYEPKPEHRF TFGLWTVGNV GRDPFGDAVR ERLDPVYVVH KLAELGAYGV NLHDEDLIPR | 60 |
|  | GTPPQERDQI VRRFKKALDE TGLKVPMVTA NLFSDPAFKD GAFTSPDPWV RAYALRKSLE | 120 |
|  | TMDLGAELGA EIYVVWPGRE GAEVEATGKA RKVWDWVREA LNFMAAYAED QGYGYRFALE | 180 |
|  | PKPNEPRGDI YFATVGSMLA FIHTLDRPER FGLNPEFAHE TMAGLNFVHA VAQALDAGKL | 240 |
|  | FHIDLNDQRM SRFDQDLRFG SENLKAAFFL VDLLESSGYQ GPRHFDAHAL RTEDEEGVWA | 300 |
|  | FARGCMRTYL ILKERAEAFR EDPEVKELLA AYYQEDPAAL ALLGPYSREK AEALKRAELP | 360 |
|  | LEAKRRRGYA LERLDQLAVE YLLGVRG | 387 |
| 8 | MYEPKPEHRF TFGLWTVGNV GRDPFGDAVR ERLDPVYVGH KLAELGVHGV NLHDEDLIPR | 60 |
|  | GTPPQERDQI VRRFKRALDE TGLKVPMVTG NLFSDPGFKD GGFTSRDPWV RAYAFRKSLE | 120 |
|  | TMDLGAELGA EIYVVWPGRE GAEVEATGKA RKVWDWVREA LNFMAAYAED QGYGYRFALE | 180 |
|  | PKPNEPRGDI YFATVGSMLA LIHTLERPER FGLNPEFAHE TMAGLNFVHA VAQALDAGKL | 240 |
|  | LHIDLNGQRM NRFDQDLRFG SENLKAAFLL VDLLESSGYQ GPRHFDAHAL RTEDEEGVWA | 300 |
|  | FARGCMRTYL ILKERAEAFR EDPEVKELLA AYYQEDPAAL PLMDPYSHEK AEALKRAELP | 360 |
|  | LEAKRHRGYA LERLDQLAVE YLLGVRG | 387 |
| 9 | MSYQPTPEDR FTFGLWTVGW QGRDPFGDAT RPALDPVETV QRLAELGAHG VTFHDDDLIP | 60 |
|  | FGSSDTERES HIKRFRQALD ATGMTVPMAT TNLFTHPVFK DGGFTANDRD VRRYALRKTI | 120 |
|  | RNIDLAVELG AKTYVAWGGR EGAESGGAKD VRVALDRMKE AFDLLGEYVT SQGYDIRFAI | 180 |
|  | EPKPNEPRGD ILLPTVGHAL AFIERLERPE LYGVNPEVGH EQMAGLNFPH GIAQALWAGK | 240 |

TABLE 1-continued

DNA and amino acid sequences as exemplified herein. SEQ ID NO: 1-
18 are xylose isomerases from a number of bacterial species, known in the art per se. SEQ
ID NO: 19 and 20 are a COT A laccase from *Bacillus subtilis* and *Escherichia coli*
respectively, SEQ ID NO: 21 is a pectate lyase (synonym: pectinase) from *Bacillus subtilis*.
SEQ ID NO: 22 represents a PPlase from *Ecoli*. SEQ ID NO:s 23-44 are DNA sequences
encoding the polypeptides with an amino acid sequence according to SEQ ID NO:s 1-22.

| SEQ ID NO: | Sequence | |
|---|---|---|
|  | LFHIDLNGQS GIKYDQDLRF GAGDLRAAFW LVDLLESAGY EGPRHFDFKP PRTEDIDGVW | 300 |
|  | ASAAGCMRNY LILKERAAAF RADPEVQEAL RASRLDELAQ PTAADGVQEL LADRTAFEDF | 360 |
|  | DVDAAAARGM AFERLDQLAM DHLLGAR | 387 |
| 10 | MAYFENVDKV VYEGPASENP LAFKFYNPEE KVGDKTMEEH LRFSVAYWHT FVGDGADPFG | 60 |
|  | VGTAIRPWNR YSGMDLAKAR VEAAFELFDK LNIPFFCFHD VDIAPEGATL KETYQNLDTI | 120 |
|  | VDMIEEYMKT SKTKLLWNTA NLFTHPRFVH GAATSCNADV FAYAAAKVKK GLEIAKRLGA | 180 |
|  | ENYVFWGGRE GYETLLNTNM KLELDNLARF LHMAVDYAKE IGFDGQFLIE PKPKEPTKHQ | 240 |
|  | YDFDVATALA FLQTYGLKDY FKFNIEANHA TLAGHTFEHE LRVARIHGML GSVDANQGDP | 300 |
|  | LLGWDTDEFP TDLYSTTLAM YEILQNGGLG KGGLNFDAKV RRGSFEPEDL FYAHIAGMDS | 360 |
|  | FAIGLKVAYR LIEDRVFESV VEERYKSYTE GIGRDIIDGK ADFHTLEAYA LNLRDISNRS | 420 |
|  | GRQERLKTLL NQYLLEVCVA R | 441 |
| 11 | MSVQPTPADH FTFGLWTVGW TGADPFGVAT RKNLDPVEAV HKLAELGAYG ITFHDNDLIP | 60 |
|  | FDATEAEREK ILGDFNQALK DTGLKVPMVT TNLFSHPVFK DGGFTSNDRS IRRFALAKVL | 120 |
|  | HNIDLAAEMG AETFVMWGGR EGSEYDGSKD LAAALDRMRE GVDTAAGYIK DKGYNLRIAL | 180 |
|  | EPKPNEPRGD IFLPTVGHGL AFIEQLEHGD IVGLNPETGH EQMAGLNFTH GIAQALWAEK | 240 |
|  | LFHIDLNGQR GIKYDQDLVF GHGDLTSAFF TVDDLLENGFP NGGPKYTGPR HFDYKPSRTD | 300 |
|  | GYDGVWDSAK ANMSMYLLLK ERALAFRADP EVQEAMKTSG VFELGETTLN AGESAADLMN | 360 |
|  | DSASFAGFDA EAAAERNFAF IRLNQLAIEH LLGSR | 395 |
| 12 | MEVFKNVPQT IKYEGKDSDN PLAFKYYNPE EKVGGKTMEE HLRFSVAYWH TLTGDGSDPF | 60 |
|  | GMGTMLRPWD TATDPMELAK ARVRAAFEFM SKLGVKYFCF HDRDIAPEGR TLAETNKNLD | 120 |
|  | EIVSLIKELM DETGIKLLWG TANLFSNPRF VHGAATSCNA DVFAYAAAQV KKAMEITKEL | 180 |
|  | GGENYVFWGG REGYETLLNT DMELEQENFA RFLHMAVDYA REIGFEGQFL IEPKPKEPTK | 240 |
|  | HQYDFDAATV ISFLKKYDLD KHFKLNIEAN HATLAGHTFQ HELHVSRING MLGSVDANQG | 300 |
|  | DLLLGWDTDQ FPTNIYETTL AMYEILKNGG LEPGGLNFDA KVRRASFEPV DLFYAHIAGM | 360 |
|  | DAFARGLKVA HKLLESGELE DFISERYKSY RNGIGEKIVK GEVGFKELED YALNNGKITN | 420 |
|  | VSGRQELLES IVNKYIIEA | 439 |
| 13 | MMAYFPNVSK ITYSGKQLKS GLSFNHYNPK ELVGGKTMEE QLRFSVAFWH TFTESGTDPF | 60 |
|  | GAGSKIRPWD RFTGMDLAKA RVEAAFEFFE KLGNPYFCFH DRDIAPEGDT LRETNKNLDV | 120 |
|  | IVAMIKDYMK TSKVKLLWNT ANMFTNPRFV HGAASSCNAD VFAYAAAQVK KGLEVGKELG | 180 |
|  | AENYVFWGGR EGYETLLNTD LKLEQDNLAR FFHMAVDYAK EIGFDAQFLL EPKPKEPTKH | 240 |
|  | QYDFDAATTI AFLKTYDLDQ HFKLNLEANH ATLAGHTFEH EIRVARTHGL LGSLDANQGD | 300 |
|  | PLLGWDTDEF PTDLYSTTLA MYEVLKNGGL GRGGLNFDAK TRRASFTDED LFYAHIAGMD | 360 |
|  | SFALGLKVAN RLIEDRVFDA FIEERYSSYK EGIGADIVSG KADFKSLENY ILDKKEIINQ | 420 |
|  | SGRLEQLKNT LNHYIVQEAY QSVNA | 445 |
| 14 | MNYQPTPEDR FTFGLWTVGW QGRDPFGDAT RRALDPVESV RRLAELGAHG VTFHDDDLIP | 60 |
|  | FGSSDSEREE HVKRFRQALD DTGMKVPMAT TNLFTHPVFK DGGFTANDRD VRRYALRKTI | 120 |
|  | RNIDLAVELG AETYVAWGGR EGAESGGAKD VRDALDRMKE AFDLLGEYVT SQGYDIRFAI | 180 |
|  | EPKPNEPRGD ILLPTVGHAL AFIERLERPE LYGVNPEVGH EQMAGLNFPH GIAQALWAGK | 240 |
|  | LFHIDLNGQN GIKYDQDLRF GAGDLRAAFW LVDLLESAGY SGPRHFDFKP PRTEDFDGVW | 300 |
|  | ASAAGCMRNY LILKERAAAF RADPEVQEAL RASRLDELAR PTAADGLQAL LDDRSAFEEF | 360 |
|  | DVDAAAARGM AFERLDQLAM DHLLGARG | 388 |
| 15 | MQAYFDQLDR VRYEGSKSSN PLAFRHYNPD ELVLGKRMEE HLRFAACYWH TFCWNGADMF | 60 |
|  | GVGAFNRPWQ QPGEALALAK RKADVAFEFF HKLHVPPFYCF HDVDVSPEGA SLKEYINNFA | 120 |
|  | QMVDVLAGKQ EESGVKLLWG TANCFTNPRY GAGAATNPDP EVFSWAATQV VTAMEATHKL | 180 |
|  | GGENYVLWGG REGYETLLNT DLRQEREQLG RFMQMVVEHK HKIGFQGTLL IEPKPQEPTK | 240 |
|  | HQYDYDAATV YGFLKQFGLE KEIKLNIEAN HATLAGHSFH HEIATAIALG LFGSVDANRG | 300 |
|  | DAQLGWDTDQ FPNSVEENAL VMYEILKAGG FTTGGLNFDA KVRRQSTDKY DLFYGHIGAM | 360 |
|  | DTMALALKIA ARMIEDGELD KRIAQRYSGW NSELGQQILK GQMSLADLAK YAQEHHLSPV | 420 |
|  | HQSGRQEQLE NLVNHYLFDK | 440 |
| 16 | MREYFANVPK IKYEGKDSKN PLAFKYYNPD EVVGGKTMKE HLRFTLSYWH TLTGAGSDPF | 60 |
|  | GVGTMLRPWD CAEDEMELAK MRMEANFELM DKLGIEYFAF HDRDIAPEGK TLADTNEKLD | 120 |
|  | EIVAYCKELM QKHGKKLLWG TANMFGNPRF VHGAATTCNA DVFAYAAAQT KKAMDVTKEL | 180 |
|  | GGENYVFWGG REGYETLLNT DLGLEQDNLA RFFQMAVDYA KKIGFTGQFL IEPKPKEPTK | 240 |
|  | HQYDFDVATV LGFLRKYNLE KYFKMNIEAN HATLAQHTFQ HEVAVARVNG VLGSLDVNQG | 300 |
|  | DPNLGWDTDQ FPTNIYDATM VMYEVLKNGG IAPGGLNFDA KTRRASFEPE DLFLSYIAGM | 360 |
|  | DTMAKGLRVA YSLLDDAVLE NNTSERYKTF SEGIGKDIVE GKVDFESLEK YALENSVISN | 420 |
|  | KSGRQEYLES VVNQYIFND | 439 |
| 17 | MAQSHSSSVN YFGSVNKVVF EGKASTNPLA FKYYNPQEVI GGKTMKEHLR FSIAYWHTFT | 60 |
|  | ADGTDVFGAA TMQRPWDHYK GMDLARARVE AAFEMFEKLD APFFAFHDRD IAPEGSTLKE | 120 |
|  | TNQNLDIIVG MIKDYMRDSN VKLLWNTANM FTNPRFVHGA ATSCNADVFA YAAAQVKKGL | 180 |
|  | ETAKELGAEN YVFWGGREGY ETLLNTDLKF ELDNLARFMH MAVDYAKEIE YTGQFLIEPK | 240 |
|  | PKEPTTHQYD TDAATTIAFL KQYGLDNHFK LNLEANHATL AGHTFEHELR MARVHGLLGS | 300 |
|  | VDANQGHPLL GWDTDEFPTD LYSTTLAMYE ILQNGGLGSG GLNFDAKVRR SSFEPDDLVY | 360 |

TABLE 1-continued

DNA and amino acid sequences as exemplified herein. SEQ ID NO: 1-
18 are xylose isomerases from a number of bacterial species, known in the art per se. SEQ
ID NO: 19 and 20 are a COT A laccase from *Bacillus subtilis* and *Escherichia coli*
respectively, SEQ ID NO: 21 is a pectate lyase (synonym: pectinase) from *Bacillus subtilis*.
SEQ ID NO: 22 represents a PPIase from *Ecoli*. SEQ ID NO:s 23-44 are DNA sequences
encoding the polypeptides with an amino acid sequence according to SEQ ID NO:s 1-22.

| SEQ ID NO: | Sequence | |
|---|---|---|
|  | AHIAGMDAFA RGLKVAHKLI EDRVFEDVIQ HRYRSFTEGI GLEITEGRAN FHTLEQYALN | 420 |
|  | NKTIKNESGR QERLKAILNQ YILEV | 445 |
| 18 | MFFKNVGMIE YEGADSENPY AFKYYNPDEY VGGKTMKEHL RFAVAYWHTF DADGKDPFGD | 60 |
|  | GTMFRAWNRL TYPLDKAKAR AESAFEFFEK LGVPYFCFHD VDIVDEGATL RETFAYLDQM | 120 |
|  | SSFLKEMMET SRVQLLWNTA NMFTHPRYVH GAATSCNADV YAYAAAKVKK GLDIAKELGA | 180 |
|  | ENYVFWGGRE GYETLLNTDM KLELENLASF YRMAVEYARE IGFDGQFLIE PKPKEPTKHQ | 240 |
|  | YDFDAATTIA FLETYGLKDH FKLNLEANHA TLAGHTFEHE LRVAALHDML GSIDANQGDL | 300 |
|  | LLGWDTDEFP TDLYSAVLAM YEILKAGGFK TGGINFDAKV RRPSFADEDL FHAHIAGMDT | 360 |
|  | YAVGLKVASR LLEDKALDQV IEERYESYTK GIGLEIKEGR TDLKKLAAYA LEHDHIENQS | 420 |
|  | GRQERLKATV NRYLLNALRE APRGKETR | 448 |
| 19 | MTLEKFVDAL PIPDTLKPVQ QTTEKTYYEV TMEECAHQLH RDLPPTRLWG YNGLFPGPTI | 60 |
|  | EVKRNENVYV KWMNNLPSEH FLPIDHTIHH SDSQHEEPEV KTVVHLHGGV TPPPDSDGYPE | 120 |
|  | AWFSKDFEQT GPYFKREVYH YPNQQRGATL WYHDHAMALT RLNVYAGLVG AYIIHDPKEK | 180 |
|  | RLKLPSGEYD VPLLITDRTI NEDGSLFYPS GPENPSPSLP KPSIVPAFCG DTILVNGKVW | 240 |
|  | PYLEVEPRKY RFRVINASNA RTYNLSLDNG GEFIQIGSDG GLLPRSVKLN SFSLAPAERY | 300 |
|  | DIIIDFTAYE GESIILANSE GCGGDANPET DANIMQFRVT KPLAQKDESR KPKYLASYPS | 360 |
|  | VQNERIQNIR TLKLAGTQDE YGRVVQLLNN KRWHDPVTEA PKAGTTEIWS IVNPTQGTHP | 420 |
|  | IHLHLVSFRV LDRRPFDIAR YQERGELSYT GPAVPPPPSE KGWKDTIQAH AGEVLRIAVT | 480 |
|  | FGPYSGRYVW HCHILEHEDY DMMRPMDITD PHK | 513 |
| 20 | MQRRDFLKYS VALGVASALP LWNRAVFAAE RPTLPIPDLL TTDARNRIQL TIGAGQSTFG | 60 |
|  | GKTATTWGYN GNLLGPAVKL QRGKAVTVDI YNQLTEETTL HWHGLEVPGE VDGGPQGIIP | 120 |
|  | PGGKRSVTLN VDQPAATCWF HPHQHGKTGR QVAMGLAGLV VIEDDEILKL MLPKQWGIDD | 180 |
|  | VPVIVQDKKF SADGQIDYQL DVMTAAVGWF GDILLINGAI YPQHAAPRGW LRLRLLNGCN | 240 |
|  | ARSLNFATSD NRPLYVIASD GGLLPEPVKV SELPVLMGER FEVLVEVNDN KPFDLVTLPV | 300 |
|  | SQMGMAIAPF DKPHPVMRIQ PIAISASGAL PDTLSSLPAL PSLEGLTVRK LQLSMDPMLD | 360 |
|  | MMGMQMLMEK YGDQAMAGMD HSQMMGHMGH GNMNHMNHGG KFDFHHANKI NGQAFDMNKP | 420 |
|  | MFAAAKGQYE RWVISGVGDM MLHPFHIHGT QFRILSENGK PPAAHRAGWK DTVKVEGNVS | 480 |
|  | EVLVKFNHDA PKEHAYMAHC HLLEHEDTGM MLGFTVSDP | 519 |
| 21 | MKELGHEVLK PYDGWAAYGE GTTGGAMASP QNVFVVTNRT ELIQALGGNN HTNQYNSVPK | 60 |
|  | IIYVKGTIDL NVDDNNQPVG PDFYKDPHFD FEAYLREYDP ATWGKKEVEG PLEEARVRSQ | 120 |
|  | KKQKDRIMVY VGSNTSIIGV GKDAKIKGGG FLIKNVDNVI IRNIEFEAPL DYFPEWDPTD | 180 |
|  | GTLGEWNSEY DSISIEGSSH IWIDHNIFTD GDHPDRSLGT YFGRPFQQHD GALDIKNSSD | 240 |
|  | FITISYNVFT NHDKVTLIGA SDSRMADSGH LRVTLHHNYY KNVTQRLPRV RFGQVHIYNN | 300 |
|  | YYEFSNLADY DFQYAWGVGV FSQIYAQNNY FSFDWIDPS LIIKVWSKNE ESMYETGTIV | 360 |
|  | DLPNGRRYID LVASYNESNT LQLKKEVTWK PMFYHVIHPT PSVPALVKAK AGAGNLH | 417 |
| 22 | MVTFHTNHGD IVIKTFDDKA PETVKNFLDY CREGFYNNTI FHRVINGFMI QGGGFEPGMK | 60 |
|  | QKATKEPIKN EANNGLKNTR GTLAMARTQA PHSATAQFFI NVVDNDFLNF SGESLQGWGY | 120 |
|  | CVFAEVVDGM DVVDKIKGVA TGRSGMHQDV PKEDVIIESV TVSEGTSENL YFQGA | 175 |
| 23 | atggccgaat tttttcctga gattccgaaa attcagttcg aaggtaaaga aagcaccaat | 60 |
|  | ccgctggcat ttcgttttta tgatccgaac gaagtgattg atggtaaacc gctgaaagat | 120 |
|  | cacctgaaat ttagcgttgc attttggcat accttttgtga atgaaggtcg tgatccgttt | 180 |
|  | ggtgatccga ccgcagaacg tccgtggaat cgtttttagcg atccgatgga taaagcattt | 240 |
|  | gcacgtgttg atgcactgtt tgaattttgc gaaaaactga acatcgagta tttctgcttt | 300 |
|  | cacgatcgcg atattgcacc ggaaggtaaa accctgcgta aaccaacaa aattctgaat | 360 |
|  | aaagtggtgg aacgcatcaa agaacgtatg aaagatagca atgttaaact gctgtggggc | 420 |
|  | accgcaaacc tgtttagcca tccgcgttat atgcatggtg cagcaaccac ctgtagcgca | 480 |
|  | gatgtttttg cctatgcagc agcacaggtt aaaaaagcac tggaaatcac caaagaactg | 540 |
|  | ggtggtgaag gttatgtttt ttggggtggt cgtgaaggct atgaaacact gctgaataac | 600 |
|  | gatctgggtc tggaactgga aaatctggca cgtttctgc gtatggcagt tgaatatgcg | 660 |
|  | aaaaaaatcg gttttaccgg tcagttttcg attgaaccga accgaaaga accgaccaaa | 720 |
|  | caccagtatg attttgatgt tgcaaccgcc tatgccttc tgaaaaatca tggtctggat | 780 |
|  | gagtacttca aattcaacat tgaagcaaat catgcaaccc tggcaggtca tacctttcag | 840 |
|  | catgaactgc gcatggcacg cattctgggt aaactgggta gcattgatgc caatcagggt | 900 |
|  | gatctgctgc tgggttggga tacagatcag tttccgacca catttatga taccaccctg | 960 |
|  | gcaatgtatg aagtgattaa agccggtggt tttaccaaag tggtctgaa ttttgatgca | 1020 |
|  | aaagttctgc gtgccagcta taagttgag gacctgttta ttggtcatat cgcaggtatg | 1080 |
|  | gataccctg cactgggctt taaaatcgca tataaactgg caaagatgg cgtgttcgat | 1140 |
|  | aaattcatcg aggaaaaata tcgcagcttc aaagaaggca ttggcaaaga aattgttgag | 1200 |
|  | ggcaaaaccg actttgagaa actggaagaa tacatcatcg acaaagaaga tattgaactg | 1260 |
|  | ccgagcggca aacaagaata tctgaaagc ctgctgaaca gctatatcgt taaaaaccatt | 1320 |
|  | gcagaactgc gctaa | 1335 |
| 24 | atgagctttc agccgacccc ggaagatcgc tttaccttg gcctgtggac cgtgggctgg | 60 |
|  | cagggccgcg atccgtttgg cgatgcgacc cgcccggcgc tggatccggt ggaaaccgtg | 120 |
|  | cagcgcctgg cggaactggg cgcgtatggc gtgacctttc atgatgatga tctgattccg | 180 |

TABLE 1-continued

DNA and amino acid sequences as exemplified herein. SEQ ID NO: 1-18 are xylose isomerases from a number of bacterial species, known in the art per se. SEQ ID NO: 19 and 20 are a COT A laccase from *Bacillus subtilis* and *Escherichia coli* respectively, SEQ ID NO: 21 is a pectate lyase (synonym: pectinase) from *Bacillus subtilis*. SEQ ID NO: 22 represents a PPIase from *Ecoli*. SEQ ID NO:s 23-44 are DNA sequences encoding the polypeptides with an amino acid sequence according to SEQ ID NO:s 1-22.

| SEQ ID NO: | Sequence | |
|---|---|---|
| | tttggcagca gcgataccga acgcgaaagc catattaaac gctttcgcca ggcgctggat | 240 |
| | gcgaccggca tgaccgtgcc gatggcgacc accaacctgt ttacccatcc ggtgtttaaa | 300 |
| | gatggcggct ttaccgcgaa cgatcgcgat gtgcgccgct atgcgctgcg caaaaccatt | 360 |
| | ggcaacattg atctggcggc ggaactgggc gcgaaaacct atgtggcgtg gggcggccgc | 420 |
| | gaaggcgcgg aaagcggcgg cgcgaaagat gtgcgcgatg cgctggatcg catgaaagaa | 480 |
| | gcgtttgatc tgctgggcga atatgtgacc gcgcagggct atgatctgcg cttttgcgatt | 540 |
| | gaaccgaaac cgaacgaacc gcgcggcgat attctgctgc cgaccgtggg ccatgcgctg | 600 |
| | gcgtttattg aacgcctgga acgcccggaa ctgtatggcg tgaacccgga agtgggccat | 660 |
| | gaacagatgg cgggcctgaa cttttccgcat ggcattgcgc aggcgctgtg ggcgggcaaa | 720 |
| | ctgtttcata ttgatctgaa cggccagagc ggcattaaat atgatcagga tctgcgcttt | 780 |
| | ggcgcgggcg atctgcgcgc ggcgttttgg ctggtggatc tgctggaaac cgcgggctat | 840 |
| | gaaggcccgc gccattttga ttttaaaccg ccgcgcaccg aagattttga tggcgtgtgg | 900 |
| | gcgagcgcgg cgggctgcat gcgcaactat ctgattctga aagatcgcgc ggcggcgttt | 960 |
| | cgcgcggatc cggaagtgca ggaagcgctg cgcgcggcgc gcctggatca gctggcgcag | 1020 |
| | ccgaccgcgg cggatggcct ggatgcgctg ctggcggatc gcgcggcgtt tgaagatttt | 1080 |
| | gatgtggatg cggcggcggc gcgcggcatg gcgtttgaac atctggatca gctggcgatg | 1140 |
| | gatcatctgc tgggcgcgcg cggctaa | 1167 |
| 25 | atgaacaaat attttgaaaa cgtgagcaaa attaaatatg aaggcccgaa aagcaacaac | 60 |
| | ccgtatagct ttaaattta taacccggaa gaagtgattg atggcaaaac catggaagaa | 120 |
| | catctgcgct ttagcattgc gtattggcat acctttaccg cggatggcac cgatcagttt | 180 |
| | ggcaaagcga ccatgcagcc cccgtggaac cattataccg atccgatgga tattgcgaaa | 240 |
| | gcgcgcgtgg aagcggcgtt tgaattttt gataaaatta cgcgccgta ttttgctttt | 300 |
| | catgatcgcg atattgcgcc ggaaggcgat accctgcgcg aaaccaacaa aaacctggat | 360 |
| | accattgtgg cgatgattaa agattatctg aaaaccagca aaccaaagt gctgtggggc | 420 |
| | accgcgaacc tgtttagcaa cccgcgcttt gtgcatggcg cgagcaccag ctgcaacgcg | 480 |
| | gatgtgtttg cgtatagcgc ggcgcaggtg aaaaagcgc tggaaattac caaagaactg | 540 |
| | ggcggcgaaa actatgtgtt ttggggcggc cgcgaaggct atgaaaccct gctgaacacc | 600 |
| | gatatggaat ttgaactgga taactttgcg cgcttttctg atatggcggt ggattatgcg | 660 |
| | aaagaaattg gctttgaagg ccagttctg attgaaccga accgaaaga accgaccaaa | 720 |
| | catcagtatg attttgatgt ggcgaacgtg ctggcgtttc tgcgcaaata tgatctggat | 780 |
| | aaatattta aagtgaacat tgaagcgaac catgcgaccc tggcgtttca tgatttcag | 840 |
| | catgaactgc gctatgcgcg cattaacggc gtgctgggca gcattgatgc gaacaccggc | 900 |
| | gatatgctgc tgggctggga taccgatcag tttccgaccg atattcgcat gaccacctg | 960 |
| | gcgatgtatg aagtgattaa aatgggcggc tttgataaag gcggcctgaa ctttgatgcg | 1020 |
| | aaagtgcgcc gcgcgagctt tgaaccggaa gatctgtttc tgggccatat tgcgggcatg | 1080 |
| | gatgcgtttg cgaaaggctt taaagtggcg tataaactgg tgaaagatcg cgtgtttgat | 1140 |
| | aaatttattg aagaacgcta tgcgagctat aaagatggca ttggcgcgga tattgtgagc | 1200 |
| | ggcaaagcgg attttcgcag cctggaaaaa tatgcgctgg aacgcagcca gattgtgaac | 1260 |
| | aaaagcggcc gccaggaact gctgaaaagc attctgaacc agtatctgtt tgcggaataa | 1320 |
| 26 | atgccgtttg ttgatcatcg tgcacagaaa attcgtcgca gcaaagaaga actgctgaaa | 60 |
| | catatgcaga ccttcaaact ggatctgaaa tttagcgtgg gcatctggta ttttacaccg | 120 |
| | ggtggtggtc gttttcatga accgtatgtt gaacagaaaa gcattccgga acgtattgaa | 180 |
| | atggcagcag aaatggcaaa atttggcgtg aaaggtattg aagcacatta tccggctgaa | 240 |
| | gtgaatgaag aaaatctgca cctgtataaa cagctggaaa agaagcagg tattcgtctg | 300 |
| | gttgcagttc cgctgagcct gttttatgat aaaatctttg aatttggcag cctgagcaac | 360 |
| | ccgtatgaaa aatatcgtaa agttgcctat gaacgcctgg tgaatggtct gaaactggtt | 420 |
| | aaagaagcaa acgccgatat ttgcattatt tggcctggta ttgatggcta tacctatagc | 480 |
| | tatggtcacc tgtattatca catgtgggat accttgag aactggttgc acaggcaatg | 540 |
| | gatgaagttc cgggtgttca ggttgcaatt gaaccgaaac cgtatgaacc ggcaccgaat | 600 |
| | aacatttatc gtaccaccgc agatggtatt ctggcagcac gtgatattga agcgcgtctg | 660 |
| | aaaaatccgg aaaacctgaa actgctgcaa aaggtcacg cactggttgg tctgaatccg | 720 |
| | gaagttggtc atgttcgtat gggttttgaa gatctgccgt atgcatatgc ccgtgttgca | 780 |
| | cgtgaaggtc gtctgtttca tacccattgg aatagccagc cgctgggtaa ttatgatcag | 840 |
| | gatctgaata ttggtgtggt ggattgggat agcaccgaag cactgctgta taccctgaaa | 900 |
| | atggttggtt atcagggcta ttttggcatc gatatcaatc ggaacgcat gccggttatt | 960 |
| | aaagccattg aaattaacac caaagtgctg cagattatga cgaacgcat gaacgtctg | 1020 |
| | ccgcatgatc gtattattga gtgttatttt gaccctgaga atcatcgtgg tgaactggaa | 1080 |
| | ctgattctgg ccgaaaatca taaataa | 1107 |
| 27 | atgagcagct atcgtccgga accggaagat aaattcagct ttggtctgtg gaccgttggt | 60 |
| | tggcgtggtg ttaataccct tggtgatgca gttcgtccgc ctctggaccc tgcagaagca | 120 |
| | gttcatcgtc tggcaggtct gggtgcatat ggtattacct tcatgatga tctgattt | 180 |
| | ccgcctggta gcagcgcagc agaacgtgat gcaattctgg tcgtttcg taaagcactg | 240 |
| | gatgaaaccg gtctgaccgt tccgatggca accgttaacc tgttcaca tccggttttt | 300 |
| | cgtgatggtg gttttaccag caatagccgt gcaacccgtc gttatgcaat tcgcaaagca | 360 |
| | gttcgtgcaa ttgatctggc agccgaactg ggtcacgta cctttgtttg ttggggtggt | 420 |
| | caggatggtg cagaaaccga agcaggtaaa gatgatcgtg cagcactgga acgtctgcgt | 480 |
| | gaagcattta atctgatgtg tggttatgtt cgtgaacagg ttatgatct gcgttttgca | 540 |
| | gttgaaccga aaccgaatga accgcgtggt gatgtgctgc tgccgaccgt gggtcatgca | 600 |

TABLE 1-continued

DNA and amino acid sequences as exemplified herein. SEQ ID NO: 1-
18 are xylose isomerases from a number of bacterial species, known in the art per se. SEQ
ID NO: 19 and 20 are a COT A laccase from Bacillus subtilis and Escherichia coli
respectively, SEQ ID NO: 21 is a pectate lyase (synonym: pectinase) from Bacillus subtilis.
SEQ ID NO: 22 represents a PPlase from Ecoli. SEQ ID NO:s 23-44 are DNA sequences
encoding the polypeptides with an amino acid sequence according to SEQ ID NO:s 1-22.

| SEQ ID NO: | Sequence | |
|---|---|---|
| | ctggcattta ttggtgaact ggaacatccg gaaatggttg gtgtgaatcc ggaagttggt | 660 |
| | catgagcaga tggcaggcct gaattttgca catggtgttg cacaggcact gtggcatggt | 720 |
| | aaactgtttc atattgatct gaatggtcag cgtggcgtga aatatgatca ggatctgcgc | 780 |
| | tttggtgccg gtgatgttaa agaagcattt tttctggttg atcgctgga acgtagcgat | 840 |
| | tatgatggtc cgcgtcattt tgattttaaa ccgcctcgta ccgaagatgt tgatggtgtt | 900 |
| | tgggaaagcg cagccgcatg tatgcgtaat tatctgattc tgaaagaaaa agccgcagca | 960 |
| | tttcgtgccg atcctgaagt tgcagatgcc ctggcagcaa gccgtgttgc agaactgagc | 1020 |
| | gaaccgaccc tgggcaccgg tgaaagcctg gcagacctgc tggcggaaga ttttgatgtg | 1080 |
| | gatgcagccg gtgaactgtg ttatcatttt gaacgtctgg atcagctggc aatggatcac | 1140 |
| | ctgtttggtg ttcgttaa | 1158 |
| 28 | atgccgtatt ttgataacat tagcaccatt gcgtatgaag gcccggcgag caaaaacccg | 60 |
| | ctggcgttta aattttataa cccggaagaa aaagtgggcg ataaaaccat ggaagaacat | 120 |
| | ctgcgcttta gcgtggcgta ttggcatacc tttaccggcg atggcagcga tccgtttggc | 180 |
| | gcgggcaaca tgattcgccc gtggaacaaa tatagcggca tggatctggc gaaagcgcgc | 240 |
| | gtggaagcgg cgtttgaatt ttttgaaaaa ctgaacattc cgttttttg cttttcatgat | 300 |
| | gtggatattg cgccggaagg cgaaaccctg aaagaaacct ataaaaacct ggatattatt | 360 |
| | gtggatatga ttgaagaata tatgaaaacc agcaaaacca aactgctgtg gaacaccgcg | 420 |
| | aacctgttta cccatccgcg ctttgtgcat ggcgcggcga ccagctgcaa cgcggatgtg | 480 |
| | tttgcgtatg cggcggcgaa agtgaaaaaa ggcctgaaaa ttgcgaaacg cctgggcgcg | 540 |
| | gaaaactatg tgttttgggg cggccgcgaa ggctatgaaa ccctgctgaa caccgatatg | 600 |
| | aaactggaac tggataaacct ggcgcgcttt ctgcatatgg ccgtggatta tgccgaaagaa | 660 |
| | attggctttg atggccagtt tctgattgaa ccgaaaccga agaaccgac caaacatcag | 720 |
| | tatgattttg atgtggcgac cgcgctggcg tttctgcaga cctatggcct gaaagattat | 780 |
| | tttaaattta acattgaagc gaaccatgcg acccgtaccg gccatacctt tgaacatgaa | 840 |
| | ctgcgcgtgg cgcgcattca tggcatgctg ggcagcgtgg atgcgaacca gggcgatatg | 900 |
| | ctgctgggct gggataccga tgaatttccg accgatctgt atagcaccac cctggcgatg | 960 |
| | tatgaaattc tgaaaaacg cggcctgggc cgcggcggcc tgaactttga tgcgaaagtg | 1020 |
| | cgccgcgcca gctttgaacc ggaagatctg ttttatgcgc atattgcggg catggatagc | 1080 |
| | tttgcggtgg gcctgaaagt ggccgcatcgc ctgattgaag atcgcgtgtt tgatgaattt | 1140 |
| | attgaagaac gctataaaag ctataccgaa ggcattggcc gcgaaattgt ggaaggcacc | 1200 |
| | gcggattttc ataaactgga agcgcatgcg ctgcagctgg cgaaattca gaaccagagc | 1260 |
| | ggccgccagg aacgcctgaa aaccctgctg aaccagtatc tgctggaagt gtgcgcggcg | 1320 |
| | cgctaa | 1326 |
| 29 | atgtatgaac cgaaaccgga acatcgcttt acctttggcc tgtggaccgt gggcaacgtg | 60 |
| | ggccgcgatc cgtttggcga tgcggtgcgc gaacgctgga tccggtgta tgtggtgcat | 120 |
| | aaactggcgg aactgggcgc gtatggcgtg aacctgcatg atgaagatct gattccgcgc | 180 |
| | ggcaccccgc cgcaggaacg cgatcagatt gtgcgccgct ttaaaaaagc gctggatgaa | 240 |
| | accggcctga agtgccgat ggtgaccgcg aacctgttta gcgatccggc gtttaaagat | 300 |
| | ggcgcgttta ccagccgcga tccgtgggtg cgcgcgtatg cgctgcgcaa aagcctgaaa | 360 |
| | accatggatc tgggcgcgga actgggcgcg gaatttatg tggtgtggcc gggccgcaaa | 420 |
| | ggcgcggaag tggaagcgac cggcaaagcg cgcaaagtgt gggattgggt gcgcgaagcg | 480 |
| | ctgaactta tggcggcgta tgcggaagat cagggctatg gctatcgctt tgcgctggaa | 540 |
| | ccgaaaccga acgaaccgcg cggcgatatt tattttgcag ccgtgggcag catgctggcg | 600 |
| | tttattcata ccctggatcg cccggaacgc tttggcctga acccggaatt tgccgcatgaa | 660 |
| | accatggcgg gcctgaactt tgtgcatgcg gtggcgcagg cgctggatgc gggcaaactg | 720 |
| | tttcatattg atctgaacga tcagcgcatg agccgctttg atcaggatct gcgctttggc | 780 |
| | agcgaaaacc tgaaagcggc gtttttctg gtggatctgc tggaaagcag cggctatcag | 840 |
| | ggcccgcgcc attttgatgc gcatgcgctg cgcaccgaag atgaagaagg cgtgtgggcg | 900 |
| | tttgcgcgcg gctgcatgcg cacctatctg attctgaaag aacgcgcgga agcgttcgc | 960 |
| | gaagatccgg aagtgaaaga actgctggcg gcgtattatc aggaagatcc ggcggcgctg | 1020 |
| | gcgctgctgg gcccgtatag ccgcgaaaaa gcggaagcgc tgaaacgcgc ggaactgccg | 1080 |
| | ctgaagcga aacgccgccg cggctatgcg ctggaacgcc tggatcagct ggcggtggaa | 1140 |
| | tatctgctgg gcgtgcgcgg ctaa | 1164 |
| 30 | atgtatgaac cgaaaccgga acatcgcttt acctttggcc tgtggaccgt gggcaacgtg | 60 |
| | ggccgcgatc cgtttggcga tgcggtgcgc gaacgctgga tccggtgta tgtggccat | 120 |
| | aaactggcgg aactgggcgt gcatggcgtg aacctgcatg atgaagatct gattccgcgc | 180 |
| | ggcaccccgc cgcaggaacg cgatcagatt gtgcgccgct ttaaacgcgc gctggatgaa | 240 |
| | accggcctga agtgccgat ggtgaccggc aacctgttta gcgatccggg ctttaaagat | 300 |
| | ggcgcgttta ccagccgcga tccgtgggtg cgcgcgtatg cgtttcgcaa aagcctgaaa | 360 |
| | accatggatc tgggcgcgga actgggcgcg gaatttatg tggtgtggcc gggccgcaaa | 420 |
| | ggcgcggaag tggaagcgac cggcaaagcg cgcaaagtgt gggattgggt gcgcgaaccg | 480 |
| | ctgaacttta tggcggcgta tgcggaagat cagggctatg gctatcgctt tgcgctggaa | 540 |
| | ccgaaaccga acgaaccgcg cggcgatatt tattttgcag ccgtgggcag catgctggcg | 600 |
| | ctgattcata ccctggaacg cccggaacgc tttggcctga acccggaatt tgccgcatgaa | 660 |
| | accatggcgg gcctgaactt tgtgcatgcg gtggcgcagg cgctggatgc gggcaaactg | 720 |
| | ctgcatattg atctgaacgg ccagcgcatg aaccgctttg atcaggatct gcgctttggc | 780 |
| | agcgaaaacc tgaaagcggc gtttctgctg gtggatctgc tggaaagcag cggctatcag | 840 |
| | ggcccgcgcc attttgatgc gcatgcgctg cgcaccgaag atgaagaagg cgtgtgggcg | 900 |

TABLE 1-continued

DNA and amino acid sequences as exemplified herein. SEQ ID NO: 1-
18 are xylose isomerases from a number of bacterial species, known in the art per se. SEQ
ID NO: 19 and 20 are a COT A laccase from *Bacillus subtilis* and *Escherichia coli*
respectively, SEQ ID NO: 21 is a pectate lyase (synonym: pectinase) from *Bacillus subtilis*.
SEQ ID NO: 22 represents a PPIase from *Ecoli*. SEQ ID NO:s 23-44 are DNA sequences
encoding the polypeptides with an amino acid sequence according to SEQ ID NO:s 1-22.

| SEQ ID NO: | Sequence | |
|---|---|---|
| | tttgcgcgcg gctgcatgcg cacctatctg attctgaaag aacgcgcgga agcgtttcgc | 960 |
| | gaagatccgg aagtgaaaga actgctggcg gcgtattatc aggaagatcc ggcggcgctg | 1020 |
| | ccgctgatgg atccgtatag ccatgaaaaa gcggaagcgc tgaaacgcgc ggaactgccg | 1080 |
| | ctggaagcga aacgccatcg cggctatgcg ctggaacgcc tggatcagct ggcggtggaa | 1140 |
| | tatctgctgg gcgtgcgcgg ctaa | 1164 |
| 31 | atgagctatc agccgacccc ggaagatcgc tttacctttg gcctgtggac cgtgggctgg | 60 |
| | cagggccgcg atccgtttgg cgatgcgacc cgcccggcgc tggatccggt ggaaaccgtg | 120 |
| | cagcgcctgg cggaactggg cgcgcatgcc gtgaccttc atgatgatga tctgattccg | 180 |
| | tttggcagca gcgataccga acgcgaaagc catattaaac gctttcgcca ggcgctggat | 240 |
| | gcgaccggca tgaccgtgcc gatggcgacc accaacctgt ttacccatcc ggtgtttaaa | 300 |
| | gatgcggct ttaccgcgaa cgatcgcgat gtgcgccgct atgcgctgca caaaccatt | 360 |
| | cgcaacattg atctggcggt ggaactgggc gcgaaaacct atgtggcgtg gggcggccgc | 420 |
| | gaaggcgcgg aaagcggcgc ggcgaaagat gtgcgcgtgg cgctggatcg catgaaagaa | 480 |
| | gcgtttgatc tgctgggcga atatgtgacc agccagggct atgatattcg ctttgcgatt | 540 |
| | gaaccgaaac cgaacgaacc cgcgcgcgat attctgctgc cgaccgtggg ccatcgcgtg | 600 |
| | gcgtttattg aacgcctgga acgcccggaa ctgtatggcg tgaacccgga agtgggccat | 660 |
| | gaacagatgg cgggcctgaa ctttccgcat ggcattgcgc aggcgctgtg ggcgggcaaa | 720 |
| | ctgtttcata ttgatctgaa cggcagagc ggcattaaat atgatcagga tctgcgcttt | 780 |
| | ggcgcgggcg atctgcgcgc ggcgttttgg ctggtggatc tgctggaaag cgcgggctat | 840 |
| | gaaggcccgc gccattttga ttttaaaccg ccgcgcaccg aagatattga tggcgtgtgg | 900 |
| | gcgagcgcgg cgggctgcat gcgcaactat ctgattctga agaacgcgc ggcggcgttt | 960 |
| | cgcgcggatc cggaagtgca ggaagcgctg cgcgcgagcc gcctggatga actggcgcag | 1020 |
| | ccgaccgcgg cggatggcgt gcaggaactg ctggcggatc gcaccgcgtt tgaagatttt | 1080 |
| | gatgtggatg cggcggcggc gcggcatg gcgtttgaac gcctggatca gctggcgatg | 1140 |
| | gatcatctgc tgggcgcgcg ctaa | 1164 |
| 32 | atggcctatt tgagaacgt ggataaagtg gtttatgaag gtccggcaag cgaaaatccg | 60 |
| | ctggcctta aattctataa ccccggaagaa aaagtggggcg acaaaacaat ggaagaacat | 120 |
| | ctgcgtttta gcgttgcata ttggcatacc tttgttggtg atggtgcaga tccgtttggt | 180 |
| | gttggcaccg caattcgtcc gtggaatcgt tatagcggta tggatctggc aaaagcacgt | 240 |
| | gttgaagcag catttgaact gttcgataaa ctgaacatcc cgttttttg cttccacgat | 300 |
| | gttgatattg caccggaagg tgcaaccctg aaagaaacct atcagaatct ggataccatc | 360 |
| | gtggatatga tcgaagagta tatgaaaacc agcaaaacca aactgctgtg gaataccgca | 420 |
| | aacctgttta cccatccgcg ttttgttcat ggtgcagcaa ccagctgtaa tgcagatgtt | 480 |
| | tttgcctatg cagcagccaa agttaaaaaa ggtctggaaa ttgcaaaacg tctgggtgcc | 540 |
| | gaaaactata ttttttgggg tggtcgtgaa ggttataaa ccctgctgaa taccaatatg | 600 |
| | aaactggaac tggataatct ggcacgtttt ctgcacatgg cagttgatta tgcaaagaa | 660 |
| | attggtttcg atggccagtt tctgattgaa ccgaaaccga agaaccgac aaacaccag | 720 |
| | tatgattttg atgttgcaac cgcactggca tttctgcaga cctatggtct gaaagattac | 780 |
| | ttcaaattta acatcgaagc caaccatgcc accctggcag gtcataactt tgaacatgaa | 840 |
| | ctgcgtgttg cacgtattca tggtatgctg ggtagcgttg atgcaaatca gggtgatccg | 900 |
| | ctgctgggtt gggataccga tgaatttccg accgatctgt atagcaccac actggcaatg | 960 |
| | tatgaaattc tgcaaaatgg tggtctgggt aaaggtggtc tgaatttga tgccaaagtt | 1020 |
| | cgtcgtggta gctttgaacc tgaggacctg ttttatgcac atattgcagg tatggatagc | 1080 |
| | tttgcaattg gcctgaaagt tgcatatcgc ctgattgaag atcgtgtttt tgaaagcgtt | 1140 |
| | gtggaagaac gctataaag ctataccgaa ggtattggtc gcgatattat tgatggtaaa | 1200 |
| | gccgattttc ataccctgga agccatgca ctgaatctgc gtgatatttc aaatcgtagc | 1260 |
| | ggtcgtcaag aacgtctgaa aacactgctg aaccagtatc tgctggaagt ttgtgttgcc | 1320 |
| | cgttaa | 1326 |
| 33 | atgagcgtgc agccgacccc ggcggatcat tttacctttg gcctgtggac cgtgggctgg | 60 |
| | accggcgcgg atccgtttgg cgtggcgacc cgcaaaaacc tggatccggt ggaagcggtg | 120 |
| | cataaactgg cggaactggg cgcgtatgcg attacctttc atgataacga tctgattccg | 180 |
| | tttgatgcga ccgaagcgga acgcgaaaaa attctgggcg attttaacca ggcgctgaaa | 240 |
| | gataccggcc tgaaagtgcc gatggtgacc accaacctgt ttagccatcc ggtgtttaaa | 300 |
| | gatgcggct ttaccagcaa cgatcgcagc attcgccgct ttgcgctggc aaaagtgctg | 360 |
| | cataacattg atctggcggc ggaaatgggc gcgaaaacct ttgtgatgtg gggcggccgc | 420 |
| | gaaggcagcg aatatgatgg cagcaaagat ctggcggcgg cgctggatcg catgcgcgaa | 480 |
| | ggcgtggata ccgcgggcgg ctatattaaa gataaaggct ataacctgcg cattgcgctg | 540 |
| | gaaccgaaac cgaacgaacc gcgcggcgat attttctgc cgaccgtggg ccatgcgctg | 600 |
| | gcgtttattg aacagctgga acgcccggaa ctgtatggcg tgaacccgga aaccggccat | 660 |
| | gaacagatgg cgggcctgaa ctttacccat ggcattgcgc aggcgctgtg ggcggaaaaa | 720 |
| | ctgtttcata ttgatctgaa cggcagcgc ggcattaaat atgatcagga tctggtgttt | 780 |
| | ggccatggcg atctgaccag cgcgttttt accgtggatc tgctggaaaa cggctttcg | 840 |
| | aacgcggcc gaaatatac cggcccgcgc cattttgatt ataaccgga ccgcaccatt | 900 |
| | ggctatgatg gcgtgtggga tagcgcgaaa gcgaacatga gcatgtatct gctgctgaaa | 960 |
| | gaacgcgcgc tggcgtttcg cgcggatccg gaagtgcagg aagcgatgaa aaccagcggc | 1020 |
| | gtgtttgaac tgggcgaaac caccctgaac gcgggcgaaa gcggcggga tctgatgaac | 1080 |
| | gatagcgcga gctttgcggg ctttgatgcg gaagcggcgg cggaacgcaa cttcgtgtt | 1140 |
| | attcgcctga accagctggc gattgaacat ctgctgggca gccgctaa | 1188 |

TABLE 1-continued

DNA and amino acid sequences as exemplified herein. SEQ ID NO: 1-
18 are xylose isomerases from a number of bacterial species, known in the art per se. SEQ
ID NO: 19 and 20 are a COT A laccase from *Bacillus subtilis* and *Escherichia coli*
respectively, SEQ ID NO: 21 is a pectate lyase (synonym: pectinase) from *Bacillus subtilis*.
SEQ ID NO: 22 represents a PPlase from *Ecoli*. SEQ ID NO:s 23-44 are DNA sequences
encoding the polypeptides with an amino acid sequence according to SEQ ID NO:s 1-22.

| SEQ ID NO: | Sequence | |
|---|---|---|
| 34 | atggaagtgt ttaaaaacgt tccgcagacc atcaaatatg agggtaaaga tagcgataat | 60 |
| | ccgctggcct ttaaatacta taacccggaa gaaaaagtgg gtggcaaaac aatggaagaa | 120 |
| | catctgcgtt ttagcgttgc atattggcat accctgaccg gtgatggtag cgatccgttt | 180 |
| | ggtatgggca ccatgctgcg tccgtgggat accgcaaccg atccgatgga actggcaaaa | 240 |
| | gcacgtgttc gtgcagcatt tgaattcatg agcaaactgg gtgtgaaata cttttgcttt | 300 |
| | catgatcgtg atattgcacc ggaaggtcgt accctggcag aaaccaataa aaacctggat | 360 |
| | gaaattgtga gcctgatcaa agaactgatg gatgaaaccg gtattaaact gctgtggggc | 420 |
| | accgcaaacc tgtttagcaa tccgcgtttt gttcatggtg cagcaaccag cccgaatgca | 480 |
| | gatgttttg catatgccgc agcacaggtt aaaaaagcaa tggaaatcac aaaagaactg | 540 |
| | ggtggcgaaa actatgtttt tgggggtggt cgtgaaggtt atgaaaccct gctgaatacc | 600 |
| | gatatggaac tggaacaaga aaactttgca cgctttctgc atatgccgtt tgattatgca | 660 |
| | cgtgaaattg gttttgaagg ccagttcctg attgaaccga aaccgaaaga accgaccaaa | 720 |
| | caccagtatg attttgatgc agccaccgtt attagctttc tgaaaaaata cgatctggac | 780 |
| | aaacacttca aactgaacat tgaagcaaat catgcaacac tggcaggtca tacctttcag | 840 |
| | catgaactgc atgttagccg tattaatggt atgctgggta gcgttgatgc aaatcagggt | 900 |
| | gatctgctgc tgggttggga tacagatcag tttccgacca atatctatga aaccaccctg | 960 |
| | gccatgtatg agatcctgaa aaatggtggt ctggaaccgg gtggtctgaa cttttgatgcc | 1020 |
| | aaagttcgtc gtgccagctt tgaaccggtt gacctgtttt atgcacatat tgcaggtatg | 1080 |
| | gatgcatttg cacgcggtct gaaagttgca cacaaactgc tggaaagcgg tgaactggaa | 1140 |
| | gattttatca gcgaacgcta taaaagctat cgcaatggta ttggcgagaa aattgttaaa | 1200 |
| | ggtgaggtgg gctttaaaga gctggaagac tacgcactga ataacggcaa aatcaccaat | 1260 |
| | gttagcggtc gtcaagagct gctggaatca attgtgaaca aatatatcat cgaagcctaa | 1320 |
| 35 | atgatggcgt attttccgaa cgtgagcaaa attacctata gcggcaaaca gctgaaaagc | 60 |
| | ggcctgagct ttaaccatta taacccgaaa gaactggtgg gcggcaaaac catggaagaa | 120 |
| | cagctgcgct ttagcgtggc gttttggcat acctttaccg aaagcggcac cgatccgttt | 180 |
| | ggcgcgggca gcaaaattcg cccgtgggat cgctttaccg gcatggatct ggcgaaagcg | 240 |
| | cgcgtggaag cggcgtttga attttttgaa aaactggcga acccgtattt ttgctttcat | 300 |
| | gatcgcgata ttgcgccgga aggcgatacc ctgcgcgaaa ccaacaaaaa cctgatgtg | 360 |
| | attgtggcga tgattaaaga ttatatgaaa accagcaaag tgaaactgct gtggaacacc | 420 |
| | gcgaacatgt ttaccaaccc gcgctttgtg catggcgcgg cgagcagctg caacgcggat | 480 |
| | gtgtttgcgt atgcggcggc gcaggtgaaa aaagcctatg aagtgggcaa agaactgggc | 540 |
| | gcgaaaaact atgtgttttt gggcggccgc gaaggctatg aaaccctgct gaacaccgat | 600 |
| | ctgaaactgg aacaggataa cctggcgcgc tttttcata tggcggtgga ttatgcgaaa | 660 |
| | gaaattggct ttgatgcgca gtttctgctg gaaccgaaac cgaaagaacc gaccaaacat | 720 |
| | cagtatgatt ttgatgcggc gaccaccatt gcgtttctga aaacctatga tctggatcag | 780 |
| | cattttaaac tgaacctgga agcgaaccat gcgaccctgg cgggccatac ctttgaacat | 840 |
| | gaaattcgcg tggcgcgcac ccatgcctg tgggcagcc tggatgcgaa ccagggcgat | 900 |
| | ccgctgctgg gctgggatac cgatgaattt ccgaccgatc tgtatagcac caccctggcg | 960 |
| | atgtatgaag tgctgaaaaa cggcggcctg ggcgcggcg gcctgaactt tgatgcgaaa | 1020 |
| | acccgccgcg cgagctttac cgatgaagat ctgttttatg cgcatattgc gggcatggaa | 1080 |
| | agctttgcgc tgggcctgaa agtggcgaac cgcctgattg aagatcgcgt gtttgatgcg | 1140 |
| | tttattgaag aacgctatag cagctataaa gaaggcattg gcgcggata tgtgagcggc | 1200 |
| | aaagcggatt ttaaaagcct ggaaaactat attctggata aaaaagaaat tattaaccag | 1260 |
| | agcggccgcc tggaacagct gaaaaacacc ctgaaccatt atattgtgca ggaagcgtat | 1320 |
| | cagagcgtga acgcgtaa | 1338 |
| 36 | atgaactatc agccgacccc ggaagatcgc tttacctttg gcctgtggac cgtgggctgg | 60 |
| | cagggccgcg atccgtttgg cgatgcgacc cgccgcgcc tggatccggt ggaaagcgtg | 120 |
| | cgccgcctgg cggaactggg cgcgcatggc gtgaccttc atgatgatga tctgattccg | 180 |
| | tttggcagca gcgatagcga acgcgaagaa catgtgaaac gctttcgcca ggcgctggat | 240 |
| | gataccggca tgaaagtgcc gatggcgacc accaacctgt ttacccatcc ggtgtttaaa | 300 |
| | gatggcggct ttaccgcgaa cgatcgcgat gtgcgcgct atcgctgcg caaaaccatt | 360 |
| | cgcaacattg atctggcggt ggaactgggc gcgaaacct atgtggcgtg gggcggccgc | 420 |
| | gaagcgcgg aaagcggcgg cgcgaaagat gtgcgcgatg cgctggatcg catgaaagaa | 480 |
| | gcgtttgatc tgctgggcga atatgtgacc agccagggct atgatattcg ctttgcgatt | 540 |
| | gaaccgaaac cgaacgaacc gcgcgcgcgt attctgctgc cgaccgtgca tcatgcgctg | 600 |
| | gcgtttattg aacgcctgga acgcccggaa ctgtatgcg tgaacccgga agtgggccat | 660 |
| | aacagatgg cgggcctgaa cttccgcat ggcattggc aggcgctgtg gcgggcaaa | 720 |
| | ctgtttcata ttgatctgaa cggcagaac ggcattaaat atgatcagga tctgcgcttt | 780 |
| | ggcgcggggc atctgcgcgc ggcgttttgg ctggtggatc tctggaaag cgcggctat | 840 |
| | agcggccgc gccatttga ttttaaaccg ccgcgcaccg aagattttga tggcgtgtgg | 900 |
| | gcgagcgcgg cgggctgcat gcgcaactat ctgattctga aagaacgcgc ggcggcgttt | 960 |
| | cgcgcggatc cggaagtgca ggaagcgctg cgcgcgagcc gcctggatga actggcgcgc | 1020 |
| | ccgaccgcg cggatgcctt gcaggcgctg ctggatgatc gcagcgcgtt tgaagaattt | 1080 |
| | gatgtggatg cggcggcgc gcgcggcatg gcgtttgaac gcctggatca gctggcgatg | 1140 |
| | gatcatctgc tgggcgcgcg cggctaa | 1167 |
| 37 | atgcaggcgt attttgatca gctggatcgc gtgcgctatg aaggcagcaa aagcagcaac | 60 |
| | ccgctggcgt ttcgccatta taacccggat gaactggtgc tgggcaaacg catggaagaa | 120 |

TABLE 1-continued

DNA and amino acid sequences as exemplified herein. SEQ ID NO: 1-18 are xylose isomerases from a number of bacterial species, known in the art per se. SEQ ID NO: 19 and 20 are a COT A laccase from *Bacillus subtilis* and *Escherichia coli* respectively, SEQ ID NO: 21 is a pectate lyase (synonym: pectinase) from *Bacillus subtilis*. SEQ ID NO: 22 represents a PPIase from *Ecoli*. SEQ ID NO:s 23-44 are DNA sequences encoding the polypeptides with an amino acid sequence according to SEQ ID NO:s 1-22.

| SEQ ID NO: | Sequence | |
|---|---|---|
| | catctgcgct tgcggcgtg ctattggcat accttttgct ggaacggcgc ggatatgttt | 180 |
| | ggcgtgggcg cgtttaaccg cccgtggcag cagccgggcg aagcgctggc gctggcgaaa | 240 |
| | cgcaaagcgg atgtggcgtt tgaatttttt cataaactgc atgtgccgtt ttattgcttt | 300 |
| | catgatgtgg atgtgagccc ggaaggcgcg agcctgaaag aatatattaa caactttgcg | 360 |
| | cagatggtgg atgtgctggc gggcaaacag gaagaaagcg cgtgaaact gctgtggggc | 420 |
| | accgcgaact gctttaccaa cccgcgctat ggcgcgggcg cggcgaccaa cccggatccg | 480 |
| | gaagtgttta gctgggcggc gacccaggtg gtgaccgcga tggaagcgac ccataaactg | 540 |
| | ggcggcgaaa actatgtgct gtggggcggc cgcgaaggct atgaaaaccct gctgaacacc | 600 |
| | gatctgcgcc aggaacgcga acagctgggc cgctttatgc agatggtggt ggaacataaa | 660 |
| | cataaaattg gctttcaggg caccctgctg attgaaccga aaccgcagga accgaccaaa | 720 |
| | catcagtatg attatgatgc ggcgaccgtg tatggctttc tgaaacagtt tggcctggaa | 780 |
| | aaagaaatta aactgaacat tgaagcgaac catgcgaccc tggcgggcca tagctttcat | 840 |
| | catgaaattg cgaccgcgat tgcgctgggc ctgtttggca gcgtggatgc gaaccgcggc | 900 |
| | gatgcgcagc tgggctggga taccgatcag ttccgaaaca gcgtggaaga aaacgcgctg | 960 |
| | gtgatgtatg aaattctgaa agcgggcggc tttaccaccg gcggcctgaa ctttgatgcg | 1020 |
| | aaagtgcgcc gccagagcac cgataaatat gatctgtttt atggccatat tggcgcgatg | 1080 |
| | gataccatgg cgctggcgct gaaaattgcg gcgcgcatga ttgaagatgg cgaactggat | 1140 |
| | aaacgcattg cgcagcgcta tagcggctgg aacagcgaac tgggccagca gattctgaaa | 1200 |
| | ggccagatga gcctggcgga tctggcgaaa tatgcgcagg aacatcatct gagcccggtg | 1260 |
| | catcagagcg gccgccagga acagctggaa aacctggtga accattatct gtttgataaa | 1320 |
| | taa | 1323 |
| 38 | atgcgcgaat attttgcgaa cgtgccgaaa attaaatatg aaggcaaaga tagcaaaaac | 60 |
| | ccgctggcgt ttaaatatta taacccggat gaagtggtgg gcggcaaaac catgaaagaa | 120 |
| | catctgcgct ttaccctgag ctattggcat accctgaccg gcgcgggcag cgatccgttt | 180 |
| | ggcgtgggca ccatgctgcg cccgtgggat tgcgcggaag atgaaatgga actggcgaaa | 240 |
| | atgcgcatgg aagcgaactt tgaactgatg gataaactgg gcattgaata ttttgcgttt | 300 |
| | catgatcgcg atattgcgcc ggaaggcaaa accctggcgg ataccaacga aaaactggat | 360 |
| | gaaattgtgg cgtattgcaa agaactgatg cagaaacatg gcaaaaaact gctgtggggc | 420 |
| | accgcgaaca tgtttggcaa cccgcgcttt gtgcatggcg cggcgaccac ctgcaacgcg | 480 |
| | gatgtgtttg cgtatgcggc ggcgcagacc aaaaaagcga tggatgtgac caaagaactg | 540 |
| | ggcggcgaaa actatgtgtt tgggggcggc cgcgaaggct atgaaaccct gctgaacacc | 600 |
| | gatctgggcc tggaacagga taacctggcg cgctttttc agatggcggt ggattatgcg | 660 |
| | aaaaaattg ctttaccgg ccagttctg attgaaccga aaccgaaaga accgaccaaa | 720 |
| | catcagtatg attttgatgt ggcgaccgtg ctgggctttc tgcgcaaata aacctggaa | 780 |
| | aaatattta aaatgaacat tgaagcgaac catgcgaccc tggcgcagca tacctttcag | 840 |
| | catgaagtgg cggtggcgcg cgtgaacggc gtgctgggca cctggatgt gaaccaggggc | 900 |
| | gatccgaacc tgggctggga taccgatcag ttccgaccga acatttatga tgcgaccatg | 960 |
| | gtgatgtatg aagtgctgaa aaacggcggc attgcgccgg cggcctgaa ctttgatgcg | 1020 |
| | aaaacccgcc gcgcgagctt tgaaccggaa gatctgtttc tgagctatat tgcgggcatg | 1080 |
| | gataccatgg cgaaaggcct gcgcgtggcg tatagcctgc tggatgatgc ggtgctggaa | 1140 |
| | aacaacacca gcgaacgcta taaaaccttt agcgaaggca ttggcaaaga tattgtggaa | 1200 |
| | ggcaaagtgg attttgaaag cctggaaaaa tatgcgctgg aaaacagcgt gattagcaac | 1260 |
| | aaaagcggcc gccaggaata tctggaaagc gtggtgaacc agtatatttt taacgattaa | 1320 |
| 39 | atggcgcaga gccatagcag cagcgtgaac tattttggca gcgtgaacaa agtggtgttt | 60 |
| | gaaggcaaag cgagcaccaa cccgctggcg tttaaatatt ataacccgca ggaagtgatt | 120 |
| | ggcggcaaaa ccatgaaaga acatctgcgc tttagcattg cgtattggca taccttacc | 180 |
| | gcggatggca ccgatgtgtt tggcgcggcg accatgcagc gcccgtggga tcattataaa | 240 |
| | ggcatggatc tggcgcgcgc gcgcgtggaa gcggcgtttg aaatgtttga aaactggat | 300 |
| | gcgccgtttt ttgcgtttca tgatcgcgat attgcgccgg aaggcagcac cctgaaagaa | 360 |
| | accaaccaga acctggatat tattgtgggc atgattaaag attatatgcg cgatagcaac | 420 |
| | gtgaaactgc tgtggaacac cgcgaacatg tttaccaacc cgcgctttgt gcatggcgcg | 480 |
| | gcgaccagct gcaacgcgga tgtgttttcg tatgcggcgc aggtgaa aaaaggcctg | 540 |
| | gaaccgcgca aagaactggg cgcggaaaac tatgtgtttt ggggcggccg cgaaggctat | 600 |
| | gaaaccctgc tgaacaccga tctgaaattt gaactggata acctggcgcg ctttatgcat | 660 |
| | atggcggtgg attatgcgaa agaaattgaa tataccggcc agtttctgat tgaaccgaaa | 720 |
| | ccgaaagaac cgaccaccca tcagtatgat accgatggc cgaccaccat tgcgtttctg | 780 |
| | aaacagtatg gcctggataa ccattttaaa ctgaacctgg aagcagaacca tgcgaccctg | 840 |
| | gcgggccata cctttgaaca tgaactgcgc atggcgcgcg tgcatggcct gctgggcagc | 900 |
| | gtggatgcga accagggcca tccgctgctg ggctgggata ccgatgaatt tccgaccgat | 960 |
| | ctgtatagca ccaccctgcc gatgtataaa attctgcaga acgcggcct gggcagcggc | 1020 |
| | ggcctgaact ttgatgcgaa agtgcgccgc agcagctttg aaccggatga tctggtgtat | 1080 |
| | gcgcatattg cgggcatgga tgcgtttgcg cgcggcctga agtggcgca taaactgatt | 1140 |
| | gaagatcgcg tgtttgaaga tgtgattcag catcgctatc gcagctttac cgaaggcatt | 1200 |
| | ggcctggaa ttaccgaagg ccgcgcgaac tttcataccc tggaacagta tgcgctgaac | 1260 |
| | aacaaaacca ttaaaaacga aagcggccgc caggaacgcc tgaaagcgat tctgaaccag | 1320 |
| | tatattctgg aagtgtaa | 1338 |
| 40 | atgttttta aaaacgtggg catgattgaa tatgaaggcg cggatagcga aaacccgtat | 60 |
| | gcgtttaaat attataaccc ggatgaatat gtgggcggca aaaccatgaa agaacatctg | 120 |

TABLE 1-continued

DNA and amino acid sequences as exemplified herein. SEQ ID NO: 1-
18 are xylose isomerases from a number of bacterial species, known in the art per se. SEQ
ID NO: 19 and 20 are a COT A laccase from *Bacillus subtilis* and *Escherichia coli*
respectively, SEQ ID NO: 21 is a pectate lyase (synonym: pectinase) from *Bacillus subtilis*.
SEQ ID NO: 22 represents a PPlase from *Ecoli*. SEQ ID NO:s 23-44 are DNA sequences
encoding the polypeptides with an amino acid sequence according to SEQ ID NO:s 1-22.

| SEQ ID NO: | Sequence | |
|---|---|---|
| | cgctttgcgg tggcgtattg gcatacctttt gatgcggatg caaagatcc gtttggcgat | 180 |
| | ggcaccatgt ttcgcgcgtg gaaccgcctg acctatccgc tggataaagc gaaagcgcgc | 240 |
| | gcggaaagcg cgtttgaatt ttttgaaaaa ctgggcgtgc cgtatttttg ctttcatgat | 300 |
| | gtggatattg tggatgaagg cgcgaccctg cgcgaaacct ttgcgtatct ggatcagatg | 360 |
| | agcagctttc tgaaagaaat gatggaaacc agccgcgtgc agctgctgtg gaacaccgcg | 420 |
| | aacatgttta cccatccgc ctatgtgcat ggcgcggcga ccagctgcaa cgcggatgtg | 480 |
| | tatgcgtatg cggcggcgaa agtgaaaaaa ggcctggata ttgcgaaaga actgggcgcg | 540 |
| | gaaaactatg tgttttgggg cggccgcgaa ggctatgaaa ccctgctgaa caccgatatg | 600 |
| | aaactggaac tggaaaacct ggcgagcttt tatcgcatgg cggtggaata tgcgcgcgaa | 660 |
| | attggctttg atggccagtt tctgattgaa ccgaaaccga agaaccgac caaacatcag | 720 |
| | tatgattttg atgcggcgac caccattgcg tttctggaaa cctatggcct gaaagatcat | 780 |
| | tttaaactga acctggaagc gaaccatgcg accctggcgc gccataccttt tgaacatgaa | 840 |
| | ctgcgcgtgg cggcgctgca tgatatgctg ggcagcattg atgcgaacca gggcgatctg | 900 |
| | ctgctgggct gggataccga tgaatttccg accgatctgt atagcgcggt gctggcgatg | 960 |
| | tatgaaattc tgaaagcggg cggcttaaaa accggcggca ttaactttga tgcgaaagtg | 1020 |
| | cgccgcccga gctttgcgga tgaagatctg tttcatgcgc atattgcggg catggatacc | 1080 |
| | tatgcggtgg gcctgaaagt ggcgagccgc ctgctggaag ataaagcgct ggatcaggtg | 1140 |
| | attgaagaac gctatgaaag ctataccaaa ggcattggcc tggaaattaa agaaggccgc | 1200 |
| | accgatctga aaaaactggc ggcgtatgcg ctggaacatg atcatattga aaccagagc | 1260 |
| | ggccgccagg aacgcctgaa agcgaccgtg aaccgctatc tgctgaacgc gctgcgcgaa | 1320 |
| | gcgccgcgcg gcaaagaaac ccgctaa | 1347 |
| 41 | atgaccctgg aaaaatttgt ggatgcgctg ccgattccgg atacccctgaa accggtgcag | 60 |
| | cagaccaccg aaaaaaccta ttatgaagtg accatggaag aatgcgcgca tcagctgcat | 120 |
| | cgcgatctgc cgcgcacccg cctgtgggc tataacgcc tgtttccggg gccataccatt | 180 |
| | gaagtgaaac gcaacgaaaa cgtgtatgtg aaatggatga caacctgcc gagcgaacat | 240 |
| | tttctgccga ttgatcatac cattcatcat agcgatagcc agcatgaaga accggaagtg | 300 |
| | aaaaccgtgg tgcatctgca tggcggcgtg accccgccgg atagcgatgg ctatccggaa | 360 |
| | gcgtggttta gcaaagattt tgaacagacc ggcccgtatt ttaaacgcaa agtgatcat | 420 |
| | tatccgaacc agcagcgcgc cgcgaccctg tggtatcatg atcatgcgat ggcgctgacc | 480 |
| | cgcctgaacg tgtatgcggg cctggtgggc gcgtatatta ttcatgatcc gaaagaaaaa | 540 |
| | cgcctgaaac tgccgagcgg cgaatatgat gtgccgctgc tgattaccga tcgcaccatt | 600 |
| | aacgaagatg gcagcctgtt ttatccgagc ggcccggaaa acccgagccc gagcctgccg | 660 |
| | aaaccgagca ttgtgccggc gttttgcggc gataccattc tggtgaacgg caaagtgtgg | 720 |
| | ccgtatctgg aagtggaacc gcgcaaatat cgctttcgcg tgattaacgc gagcaacgcg | 780 |
| | cgcacctata acctgagcct ggataacggc ggcgaattta ttcagattgg cagcgatggc | 840 |
| | ggcctgctgc cgcgcagcgt gaaactgaac gcttttagcc tggcgccggc ggaacgctat | 900 |
| | gatattatta ttgatttac cgcgtatgaa ggcgaaagca ttattctggc gaacagcgaa | 960 |
| | ggctgcggcg gcgatgcgaa cccggaaacc gatgcgaaca ttatgcagtt tcgcgtgacc | 1020 |
| | aaaccgctgg cgcagaaaga tgaaagccgc aaaccgaaat atctggcgag ctatccgagc | 1080 |
| | gtgcagaacg aacgcattca gaacattcgc accctgaaac tggcgggcac ccaggatgaa | 1140 |
| | tatggccgcg tggtgcagct gctgaacaac aaaacgctgg catgatccggt gaccgaagcg | 1200 |
| | ccgaaagcgg gcaccaccga atttggagc attgtgaacc cgacccaggg cacccatccg | 1260 |
| | attcatctgc atctggtgag ctttcgcgtg ctggatcgcc gcccgtttga tattgcgcgc | 1320 |
| | tatcaggaac gcggcgaact gagctatacc ggcccggcgg tgccgccgcc gccgagcgaa | 1380 |
| | aaaggctgga agataccat tcaggcgcat gcgggcgaag tgctgcgcat tgcggtgacc | 1440 |
| | tttggcccgt atagcggccg ctatgtgtgg cattgccata ttctggaaca tgaagattat | 1500 |
| | gatatgatgc gcccgatgga tattaccgat ccgcataaat aa | 1542 |
| 42 | atgcagcgcc gcgattttct gaaatatagc gtggcgctgg gcgtggcgag cgcgctgccg | 60 |
| | ctgtggaacc gcgcggtgtt tgcggcggaa cgcccgaccc tgccgattcc ggatctgctg | 120 |
| | accaccgatg cgcgcaaccg cattcagctg accattggcg cgggccagag cacctttggc | 180 |
| | ggcaaaaccg cgaccacctg gggctataac ggcaacctgc tgggcccggc ggtgaaactg | 240 |
| | cagcgcggca aagcggtgac cgtggatatt tataaccgaa tgaccgaaga aaccaccctg | 300 |
| | cattggcatg gcctggaagt gccgggcgaa gtggatggcg gcccgcaggg cattattccg | 360 |
| | ccgggcggca aacgcagcgt gaccctgaac gtggatcagc cggcggcgac ctgctggttt | 420 |
| | catccgcatc agcatggcaa aaccggccgc caggtggcga tgggcctggc gggcctggtg | 480 |
| | gtgattgaag atgatgaaat tctgaaactg atgtgccga aacagtgggc cattgatgat | 540 |
| | gtgccggtga ttgtgcagga taaaaatttt agcgcggatg gccagattga ttatcagctg | 600 |
| | gatgtgatga ccgcggcggt gggctggttt ggcgataccc tgctgaccaa cggcgcgatt | 660 |
| | tatccgcagc atgcggcgcc gcgcggctgc ctgcgcctgc gctgctgaa cggctgcaac | 720 |
| | gcgcgcagcc tgaactttgc gaccagcgat aaccgcccgc tgtatgtgat tgcgagcgat | 780 |
| | ggcggcctgc tgccggaacc ggtgaaagtg agcgaactgc cggtgctgat gggcgaacgc | 840 |
| | tttgaagtgc tggtggaagt gaacgataac aaaaccgttg atctggtgac cctgccggtg | 900 |
| | agccagatgg gcatggcgat tgcgccgttt gataaaccgc atccggtgat gcgcattcag | 960 |
| | ccgattgcga ttaggccgac cggcgcgctg accgagcgct gcggcaccgt gccgagcctg | 1020 |
| | ccgagccttg aagcctgac cgtgcgcaaa ctgcagcgtga gcatgagacc gatgctgctg | 1080 |
| | atgatgggca tgcagatgct gatggaaaaa tatgcgatcc aggcgatggc gggcatggat | 1140 |
| | catagccaga tgatgggcca tatgggccat ggcaacatga accatatgaa ccatgcggcc | 1200 |
| | aaatttgatt tcatcatgc gaacaaaatt aacggccagg cgtttgatat gaacaaaccg | 1260 |
| | atgtttgcgg cggcgaaagg ccagtatgaa cgctgggtga ttagcggcgt gggcgatatg | 1320 |

TABLE 1-continued

DNA and amino acid sequences as exemplified herein. SEQ ID NO: 1-18 are xylose isomerases from a number of bacterial species, known in the art per se. SEQ ID NO: 19 and 20 are a COT A laccase from *Bacillus subtilis* and *Escherichia coli* respectively, SEQ ID NO: 21 is a pectate lyase (synonym: pectinase) from *Bacillus subtilis*. SEQ ID NO: 22 represents a PPIase from *Ecoli*. SEQ ID NO:s 23-44 are DNA sequences encoding the polypeptides with an amino acid sequence according to SEQ ID NO:s 1-22.

| SEQ ID NO: | Sequence | |
|---|---|---|
| | atgctgcatc cgtttcatat tcatggcacc cagtttcgca ttctgagcga aaacggcaaa | 1380 |
| | ccgccggcgg cgcatcgcgc gggctggaaa gataccgtga agtggaagg caacgtgagc | 1440 |
| | gaagtgctgg tgaaatttaa ccatgatgcg ccgaaagaac atgcgtatat ggcgcattgc | 1500 |
| | catctgctgg aacatgaaga taccggcatg atgctgggct ttaccgtgag cgatccgtaa | 1560 |
| 43 | atgaaagaac tgggccatga agtgctgaaa ccgtatgatg gctgggcggc gtatggcgaa | 60 |
| | ggcaccaccg gcggcgcgat ggcgagcccg cagaacgtgt ttgtggtgac caaccgcacc | 120 |
| | gaactgattc aggcgctggg cggcaacaac cataccaacc agtataacag cgtgccgaaa | 180 |
| | attatttatg tgaaaggcac cattgatctg aacgtggatg ataacaacca gccggtgggc | 240 |
| | ccggattttt ataaagatcc gcattttgat tttgaagcgt atctgcgcga atatgatccg | 300 |
| | gcgacctggg gcaaaaaaga agtggaaggc ccgctggaag aagcgcgcgt gcgcagccag | 360 |
| | aaaaaacaga aagatcgcat tatggtgtat gtgggcagca acaccagcat tattgcgtg | 420 |
| | ggcaaagatg cgaaaattaa aggcggcggc tttctgatta aaaacgtgga taacgtgatt | 480 |
| | attcgcaaca ttgaatttga agcgccgctg gattatttc cggaatggga tccgaccgat | 540 |
| | ggcaccctgg cgaatgaaa cagcgaatat gatagcatta gcattgaagg cagcagccat | 600 |
| | atttggattg atcataacac ctttaccgat ggcgatcatc cggatcgcag cctgggcacc | 660 |
| | tattttggcc gcccgtttca gcagcatgat ggcgcgctgg atattaaaaa cagcagcgat | 720 |
| | tttattacca ttagctataa cgtgtttacc aaccatgata aagtgaccct gattggcgcg | 780 |
| | agcgatagcc gcatggcgga tagcggccat ctgcgcgtga ccctgcatca taactattat | 840 |
| | aaaaacgtga cccagcgcct gccgcgcgtg cgctttggcc aggtgcatat ttataacaac | 900 |
| | tattatgaat ttagcaacct ggcggattat gattttcagt atgcgtgggg cgtgggcgtg | 960 |
| | tttagccaga tttatgcgca gaacaactat tttagctttg attgggatat tgatccgagc | 1020 |
| | ctgattatta agtgtggag caaaaacgaa gaaagcatgt atgaaaccgg caccattgtg | 1080 |
| | gatctgccga acggccgccg ctatattgat ctggtggcga gctataacga aagcaacacc | 1140 |
| | ctgcagctga aaaaagaagt gacctggaaa ccgatgtttt atcatgtgat tcatccgacc | 1200 |
| | ccgagcgtgc cggcgctggt gaaagcgaaa gcggggcgcgg gcaacctgca ttaa | 1254 |
| 44 | atggttacgt ttcacactaa tcacggcgac attgttatca agaccttcga cgacaaagca | 60 |
| | ccggaaacgg tgaagaattt cctggattat tgtcgcgagg ttttttacaa caataccatt | 120 |
| | ttccatcgtg tcattaatgg ttttatgatc cagggtggcg gtttcgagcc gggcatgaag | 180 |
| | cagaaagcca ccaaagaacc gattaagaac gaagcgaata atggcctgaa gaacacccgt | 240 |
| | ggcacgctgg cgatggcgcg tacccaggca ccacatagcg cgaccgctca attctttatc | 300 |
| | aacgttgttg ataacgattt cctgaacttt tccggtgaga gcttgcaagg ctggggttac | 360 |
| | tgcgttttcg ccgaggttgt ggacggtatg gacgtggtcg acaaaatcaa aggtgtcgcg | 420 |
| | acgggtcgca gcggtatgca ccaagatgtg ccgaaagaag atgtgattat cgagtctgtc | 480 |
| | accgtgagcg agggcacatc tgaaaacttg tatttccagg cgcc | 525 |

---

The invention claimed is:

1. A method for obtaining an active insoluble xylose isomerase, the method comprising:
    expressing, in *E. coli*, a recombinant gene encoding a fusion protein;
    wherein the fusion protein comprises a xylose isomerase linked to SEQ ID NO: 22,
    thereby obtaining the active insoluble xylose isomerase.

2. The method according to claim 1 wherein SEQ ID NO: 22 is linked to the N-terminus of the xylose isomerase.

3. The method according to claim 1, wherein SEQ ID NO: 22 is linked to the C-terminus of the xylose isomerase.

4. The method according to claim 1, further comprising lysing the host organism after expression of the recombinant gene.

5. The method according to claim 1, further comprising heat treating the expressed fusion protein.

6. The method according to claim 1, wherein the xylose isomerase comprises an amino acid sequence of any one of SEQ ID NOs: 1-18, or an amino acid sequence that is at least 90% identical to an amino acid sequence of any one of SEQ ID NOs: 1-18.

7. The method according to claim 1, wherein the xylose isomerase also has glucose isomerase activity.

8. A recombinant active insoluble xylose isomerase fusion protein, the fusion protein comprising a xylose isomerase linked to SEQ ID NO: 22 produced by the method according to claim 1.

9. The recombinant fusion protein of claim 8, wherein the xylose isomerase also has glucose isomerase activity produced by the method according to claim 1.

10. A method of converting xylose into xylulose, the method comprising:
    contacting xylose with the recombinant fusion protein of claim 8.

11. A method of converting glucose into fructose, the method comprising:
    contacting glucose with the recombinant fusion protein of claim 9.

* * * * *